(12) United States Patent
Milliman et al.

(10) Patent No.: US 7,168,604 B2
(45) Date of Patent: Jan. 30, 2007

(54) SURGICAL STAPLING DEVICE

(75) Inventors: Keith L. Milliman, Bethel, CT (US); Russell Heinrich, Madison, CT (US)

(73) Assignee: Tyco Healthcare Group LP, North Haven, CT (US)

( * ) Notice: Subject to any disclaimer, the term of this patent is extended or adjusted under 35 U.S.C. 154(b) by 56 days.

(21) Appl. No.: 10/872,747

(22) Filed: Jun. 21, 2004

(65) Prior Publication Data

US 2005/0006433 A1 Jan. 13, 2005

Related U.S. Application Data

(60) Provisional application No. 60/480,074, filed on Jun. 20, 2003.

(51) Int. Cl.
*A61B 17/10* (2006.01)
(52) U.S. Cl. .................. 227/176.1; 227/175.1
(58) Field of Classification Search ............ 227/175.1, 227/175.2, 175.3, 175.4, 176.1, 177.1, 178.1, 227/179.1, 180.1, 181.1, 182.1
See application file for complete search history.

(56) References Cited

U.S. PATENT DOCUMENTS

| | | | |
|---|---|---|---|
| 3,388,847 | A | 6/1968 | Kasulin et al. |
| 3,552,626 | A | 1/1971 | Astafiev |
| 3,638,652 | A | 2/1972 | Kelley |
| 4,198,982 | A | 4/1980 | Fortner et al. |
| 4,207,898 | A | 6/1980 | Becht |
| 4,289,133 | A | 9/1981 | Rothfuss |
| 4,304,236 | A | 12/1981 | Conta et al. |
| 4,319,576 | A | 3/1982 | Rothfuss |
| 4,350,160 | A | 9/1982 | Kolesov et al. |
| 4,351,466 | A | 9/1982 | Noiles |
| 4,379,457 | A | 4/1983 | Gravener et al. |
| 4,473,077 | A | 9/1984 | Noiles et al. |

(Continued)

FOREIGN PATENT DOCUMENTS

CA 908529 8/1972

(Continued)

OTHER PUBLICATIONS

The International Search Report dated Feb. 2, 2005 (5 pages).

*Primary Examiner*—Stephen F. Gerrity
*Assistant Examiner*—Paul Durand

(57) ABSTRACT

A surgical stapling device is disclosed for the treatment of internal hemorrhoids. The surgical stapling device includes a handle portion, an elongated body portion and a head portion including an anvil assembly and a shell assembly. The head portion includes an anvil assembly including a tiltable anvil which will tilt automatically after the device has been fired and unapproximated. The tiltable anvil provides a reduced anvil profile to reduce trauma during removal of the device after the anastomoses procedure has been performed. The anvil assembly of the stapling device may include an approximation mechanism having an anvil retainer including an elongated distal extension dimensioned to be telescopingly received within a longitudinal bore of an anvil center rod of the anvil assembly. The elongated distal extension is of a length to provide telescopic engagement with the anvil center rod without obstructing visualization of the surgical site. A kit including a surgical instrument having a removable anvil assembly and an anvil assembly insertion handle is also disclosed. The kit may also include a speculum, an anal dialator and/or an obturator.

7 Claims, 45 Drawing Sheets

U.S. PATENT DOCUMENTS

| | | | |
|---|---|---|---|
| 4,476,863 A | 10/1984 | Kanshin et al. | |
| 4,485,817 A | 12/1984 | Swiggett | |
| 4,488,523 A | 12/1984 | Shichman | |
| 4,505,272 A | 3/1985 | Utyamyshev et al. | |
| 4,505,414 A | 3/1985 | Filipi | |
| 4,550,870 A | 11/1985 | Krumme et al. | |
| 4,573,468 A | 3/1986 | Conta et al. | |
| 4,576,167 A | 3/1986 | Noiles | |
| 4,592,354 A | 6/1986 | Rothfuss | |
| 4,603,693 A | 8/1986 | Conta et al. | |
| 4,606,343 A | 8/1986 | Conta et al. | |
| 4,646,745 A | 3/1987 | Noiles | |
| 4,667,673 A | 5/1987 | Li | |
| 4,671,445 A | 6/1987 | Barker et al. | |
| 4,700,703 A | 10/1987 | Resnick et al. | |
| 4,703,887 A | 11/1987 | Clanton et al. | |
| 4,708,141 A | 11/1987 | Inoue et al. | |
| 4,754,909 A | 7/1988 | Barker et al. | |
| 4,817,847 A | 4/1989 | Redtenbacher et al. | |
| 4,873,977 A | 10/1989 | Avant et al. | |
| 4,893,622 A | 1/1990 | Green et al. | |
| 4,903,697 A | 2/1990 | Resnick et al. | |
| 4,907,591 A | 3/1990 | Vasconcellos et al. | |
| 4,917,114 A | 4/1990 | Green et al. | |
| 4,957,499 A | 9/1990 | Lipatov et al. | |
| 5,005,749 A | 4/1991 | Aranyi | |
| 5,042,707 A | 8/1991 | Taheri | |
| 5,047,039 A | 9/1991 | Avant et al. | |
| 5,104,025 A * | 4/1992 | Main et al. | 227/175.1 |
| 5,119,983 A | 6/1992 | Green et al. | |
| 5,122,156 A | 6/1992 | Granger et al. | |
| 5,139,513 A | 8/1992 | Segato | |
| 5,158,222 A | 10/1992 | Green et al. | |
| 5,188,638 A | 2/1993 | Tzakis | |
| 5,193,731 A | 3/1993 | Aranyi | |
| 5,197,648 A * | 3/1993 | Gingold | 227/179.1 |
| 5,197,649 A | 3/1993 | Bessler et al. | |
| 5,205,459 A | 4/1993 | Brinkerhoff et al. | |
| 5,221,036 A | 6/1993 | Takase | |
| 5,222,963 A | 6/1993 | Brinkerhoff et al. | |
| 5,253,793 A | 10/1993 | Green et al. | |
| 5,261,920 A | 11/1993 | Main et al. | |
| 5,271,543 A | 12/1993 | Grant et al. | |
| 5,271,544 A | 12/1993 | Fox et al. | |
| 5,275,322 A | 1/1994 | Brinkerhoff et al. | |
| 5,282,810 A | 2/1994 | Allen et al. | |
| 5,285,944 A | 2/1994 | Green et al. | |
| 5,285,945 A | 2/1994 | Brinkerhoff et al. | |
| 5,292,053 A | 3/1994 | Bilotti et al. | |
| 5,309,927 A | 5/1994 | Welch | |
| 5,312,024 A | 5/1994 | Grant et al. | |
| 5,314,435 A | 5/1994 | Green et al. | |
| 5,314,436 A | 5/1994 | Wilk | |
| 5,330,486 A | 7/1994 | Wilk | |
| 5,333,773 A | 8/1994 | Main et al. | |
| 5,344,059 A | 9/1994 | Green et al. | |
| 5,346,115 A | 9/1994 | Perouse et al. | |
| 5,348,259 A | 9/1994 | Bianco et al. | |
| 5,350,104 A | 9/1994 | Main et al. | |
| 5,355,897 A | 10/1994 | Pietrafitta et al. | |
| 5,360,154 A | 11/1994 | Green | |
| 5,368,215 A | 11/1994 | Green et al. | |
| 5,392,979 A | 2/1995 | Green et al. | |
| 5,395,030 A | 3/1995 | Kuramoto et al. | |
| 5,403,333 A | 4/1995 | Kaster et al. | |
| 5,404,870 A | 4/1995 | Brinkerhoff et al. | |
| 5,411,508 A | 5/1995 | Bessler et al. | |
| 5,433,721 A | 7/1995 | Hooven et al. | |
| 5,437,684 A | 8/1995 | Calabrese et al. | |
| 5,439,156 A | 8/1995 | Grant et al. | |
| 5,443,198 A | 8/1995 | Viola et al. | |
| 5,445,644 A | 8/1995 | Pietrafitta et al. | |
| 5,447,514 A | 9/1995 | Gerry et al. | |
| 5,454,825 A | 10/1995 | Van Leeuwen et al. | |
| 5,470,006 A | 11/1995 | Rodak | |
| 5,474,223 A | 12/1995 | Viola et al. | |
| 5,497,934 A | 3/1996 | Brady et al. | |
| 5,522,534 A | 6/1996 | Viola et al. | |
| 5,533,661 A | 7/1996 | Main et al. | |
| 5,588,579 A | 12/1996 | Schnut et al. | |
| 5,609,285 A | 3/1997 | Grant et al. | |
| 5,632,433 A | 5/1997 | Grant et al. | |
| 5,639,008 A | 6/1997 | Gallagher et al. | |
| 5,658,300 A | 8/1997 | Bito et al. | |
| 5,669,918 A | 9/1997 | Balazs et al. | |
| 5,685,474 A | 11/1997 | Seeber | |
| 5,709,335 A | 1/1998 | Heck | |
| 5,715,987 A | 2/1998 | Kelley et al. | |
| 5,718,360 A | 2/1998 | Green et al. | |
| 5,720,755 A | 2/1998 | Dakov | |
| 5,732,872 A | 3/1998 | Bolduc et al. | |
| 5,758,814 A | 6/1998 | Gallagher et al. | |
| 5,799,857 A | 9/1998 | Robertson et al. | |
| 5,836,503 A | 11/1998 | Ehrenfels et al. | |
| 5,839,639 A | 11/1998 | Sauer et al. | |
| 5,855,312 A | 1/1999 | Toledano | |
| 5,860,581 A | 1/1999 | Robertson et al. | |
| 5,868,760 A | 2/1999 | McGuckin, Jr. | |
| 5,881,943 A | 3/1999 | Heck et al. | |
| 5,915,616 A | 6/1999 | Viola et al. | |
| 5,947,363 A | 9/1999 | Bolduc et al. | |
| 5,951,576 A | 9/1999 | Wakabayashi | |
| 5,957,363 A | 9/1999 | Heck | |
| 5,993,468 A | 11/1999 | Rygaard | |
| 6,050,472 A | 4/2000 | Shibata | |
| 6,053,390 A | 4/2000 | Green et al. | |
| 6,068,636 A | 5/2000 | Chen | |
| 6,083,241 A | 7/2000 | Longo et al. | |
| 6,102,271 A | 8/2000 | Longo et al. | |
| 6,117,148 A | 9/2000 | Ravo et al. | |
| 6,119,913 A | 9/2000 | Adams et al. | |
| 6,126,058 A | 10/2000 | Adams et al. | |
| 6,149,667 A | 11/2000 | Hovland et al. | |
| 6,176,413 B1 | 1/2001 | Heck et al. | |
| 6,179,195 B1 | 1/2001 | Adams et al. | |
| 6,193,129 B1 | 2/2001 | Bittner et al. | |
| 6,203,553 B1 | 3/2001 | Robertson et al. | |
| 6,209,773 B1 | 4/2001 | Bolduc et al. | |
| 6,241,140 B1 | 6/2001 | Adams et al. | |
| 6,253,984 B1 | 7/2001 | Heck et al. | |
| 6,258,107 B1 | 7/2001 | Balázs et al. | |
| 6,264,086 B1 | 7/2001 | McGuckin, Jr. | |
| 6,269,997 B1 | 8/2001 | Balázs et al. | |
| 6,279,809 B1 | 8/2001 | Nicolo | |
| 6,302,311 B1 | 10/2001 | Adams et al. | |
| 6,338,737 B1 | 1/2002 | Toledano | |
| 6,343,731 B1 | 2/2002 | Adams et al. | |
| 6,387,105 B1 | 5/2002 | Gifford, III et al. | |
| 6,398,795 B1 | 6/2002 | McAlister et al. | |
| 6,402,008 B1 | 6/2002 | Lucas | |
| 6,450,390 B2 | 9/2002 | Heck et al. | |
| 6,478,210 B2 | 11/2002 | Adams et al. | |
| 6,488,197 B1 | 12/2002 | Whitman | |
| 6,491,201 B1 | 12/2002 | Whitman | |
| 6,494,877 B2 | 12/2002 | Odell et al. | |
| 6,503,259 B2 | 1/2003 | Huxel et al. | |
| 6,517,566 B1 | 2/2003 | Hovland et al. | |
| 6,520,398 B2 | 2/2003 | Nicolo | |
| 6,533,157 B1 | 3/2003 | Whitman | |
| 6,578,751 B2 | 6/2003 | Hartwick | |
| 6,585,144 B2 | 7/2003 | Adams et al. | |
| 6,588,643 B2 | 7/2003 | Bolduc et al. | |
| 6,592,596 B1 | 7/2003 | Geitz | |
| 6,595,887 B2 | 7/2003 | Thoma | |

| | | | | | |
|---|---|---|---|---|---|
| 6,601,749 B2 | 8/2003 | Sullivan et al. | DE | 1057729 | 5/1959 |
| 6,605,078 B2 | 8/2003 | Adams | DE | 1835500 | 4/1961 |
| 6,623,227 B2 | 9/2003 | Scott et al. | DE | 3301713 | 11/1989 |
| 6,626,921 B2 | 9/2003 | Blatter et al. | EP | 0152382 | 8/1985 |
| 6,629,630 B2 | 10/2003 | Adams | EP | 0173451 | 3/1986 |
| 6,631,837 B1 | 10/2003 | Heck | EP | 0190022 | 8/1986 |
| 6,632,227 B2 | 10/2003 | Adams | EP | 282157 | 9/1988 |
| 6,632,237 B2 | 10/2003 | Ben-David et al. | EP | 0503689 | 9/1992 |
| 6,659,327 B2 | 12/2003 | Heck et al. | FR | 1461464 | 12/1966 |
| 6,676,671 B2 | 1/2004 | Robertson et al. | FR | 1588250 | 4/1970 |
| 6,681,979 B2 | 1/2004 | Whitman | FR | 1136020 | 12/1979 |
| 6,685,079 B2 | 2/2004 | Sharma et al. | FR | 2443239 | 12/1979 |
| 6,695,198 B2 | 2/2004 | Adams et al. | GB | 1185292 | 3/1970 |
| 6,695,199 B2 | 2/2004 | Whitman | GB | 2016991 | 9/1979 |
| 6,716,222 B2 | 4/2004 | McAlister et al. | GB | 2070499 | 9/1981 |
| 6,716,233 B1 | 4/2004 | Whitman | NL | 7711347 | 10/1977 |
| 6,742,692 B2 | 6/2004 | Hartwick | WO | 8706448 | 11/1987 |
| 6,763,993 B2 | 7/2004 | Bolduc et al. | WO | 8900406 | 1/1989 |
| 6,769,590 B2 | 8/2004 | Vresh et al. | WO | 9006085 | 6/1990 |

FOREIGN PATENT DOCUMENTS

CA    1136020    1/1982

\* cited by examiner

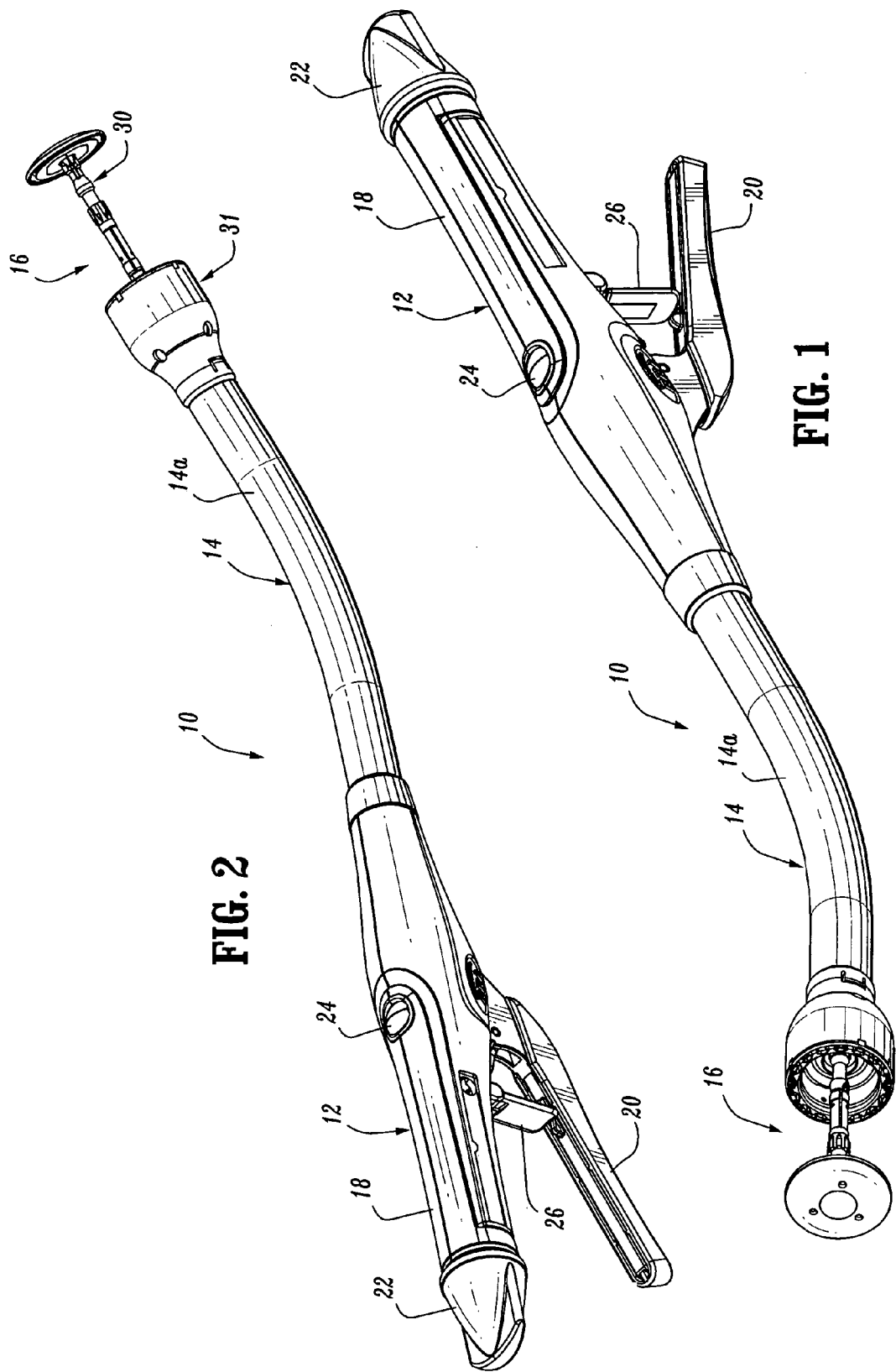

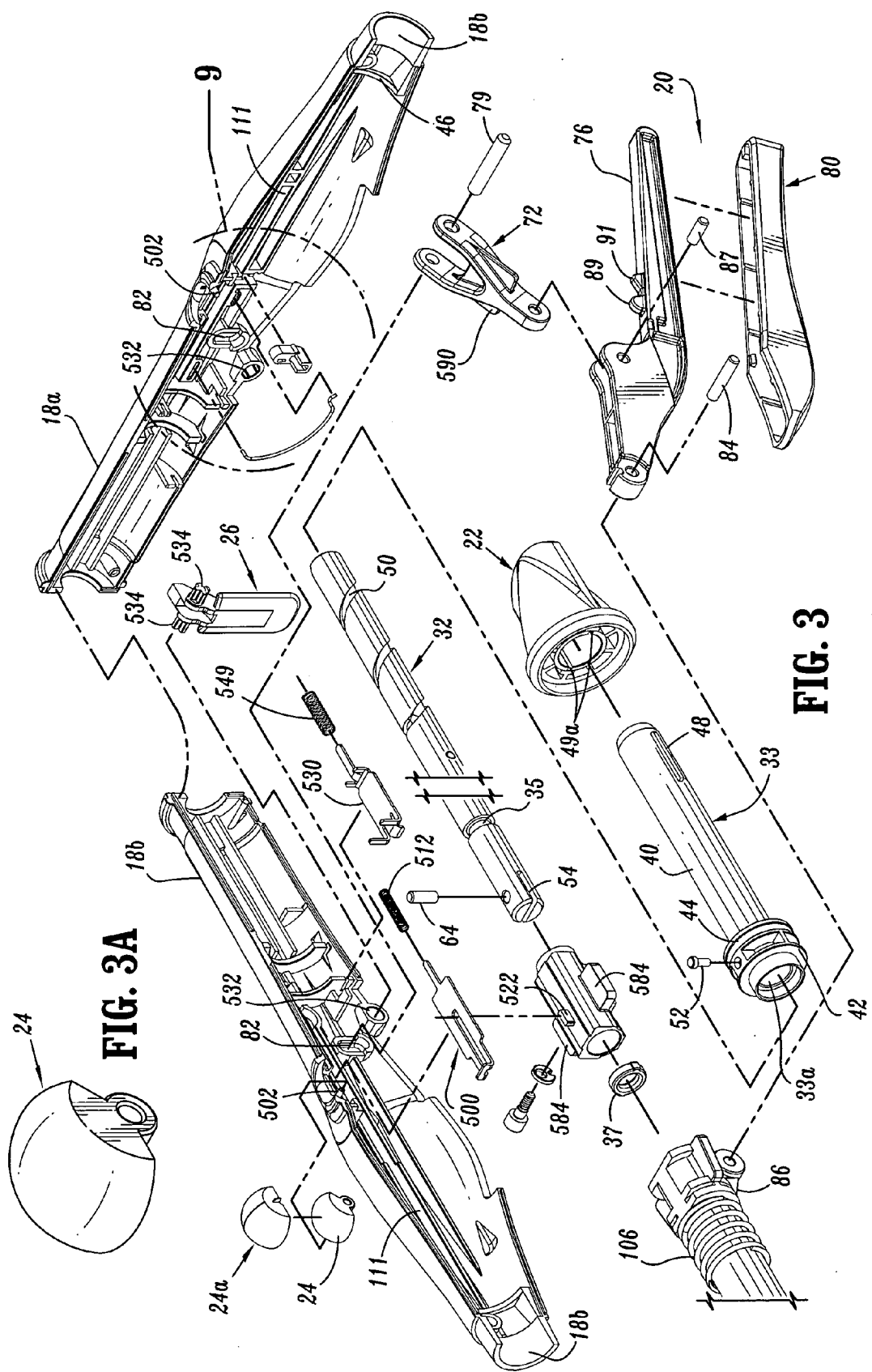

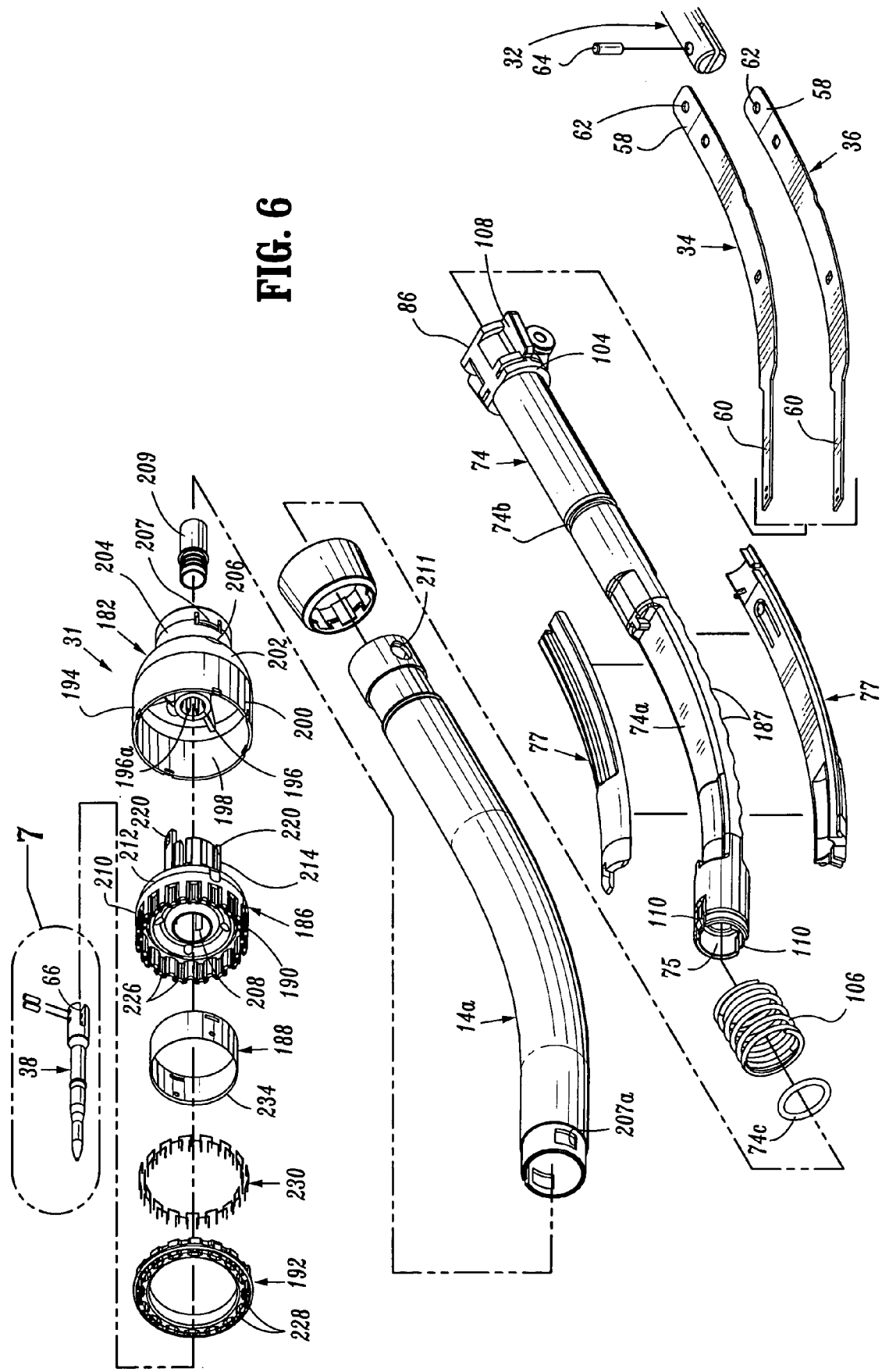

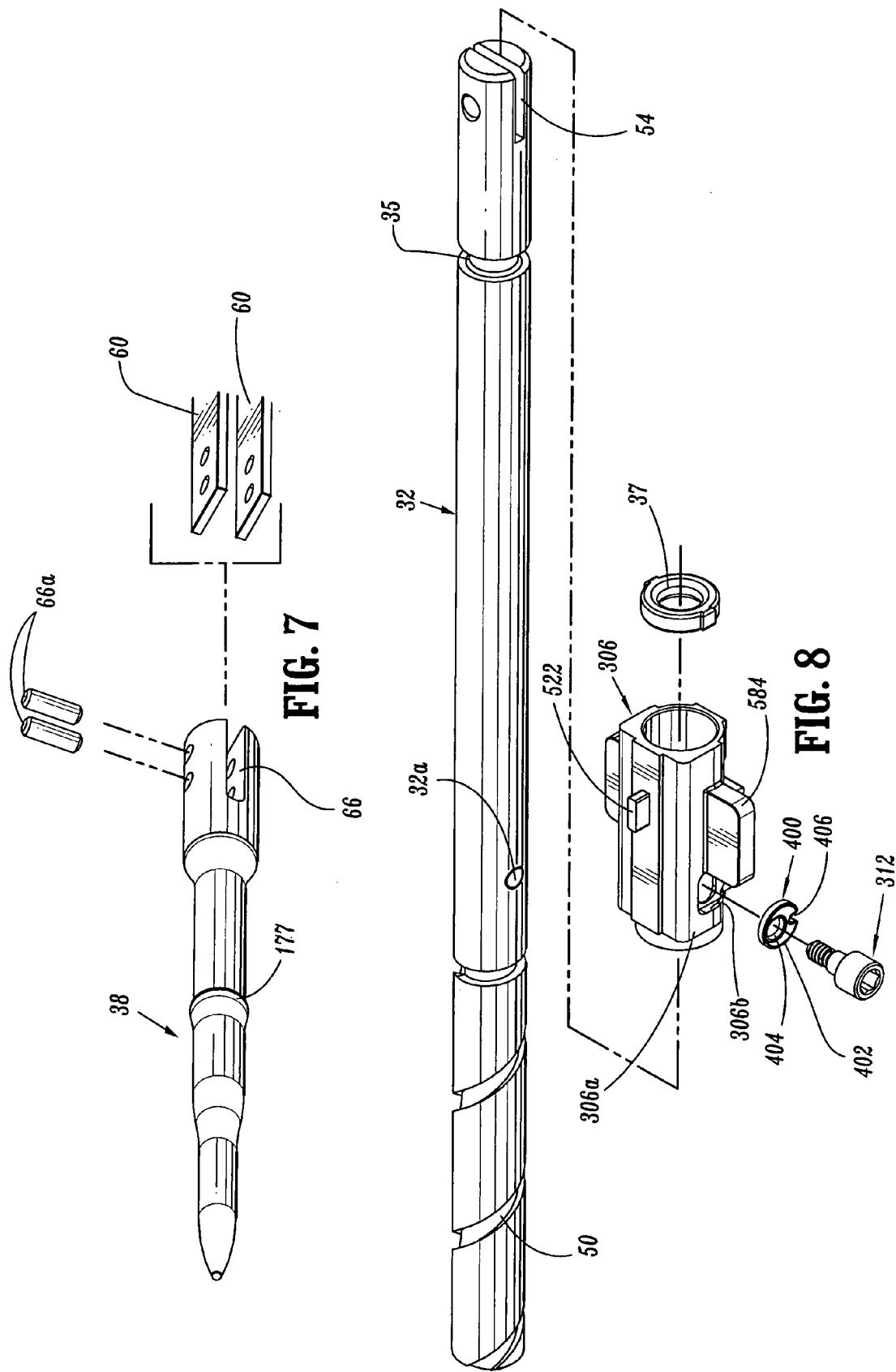

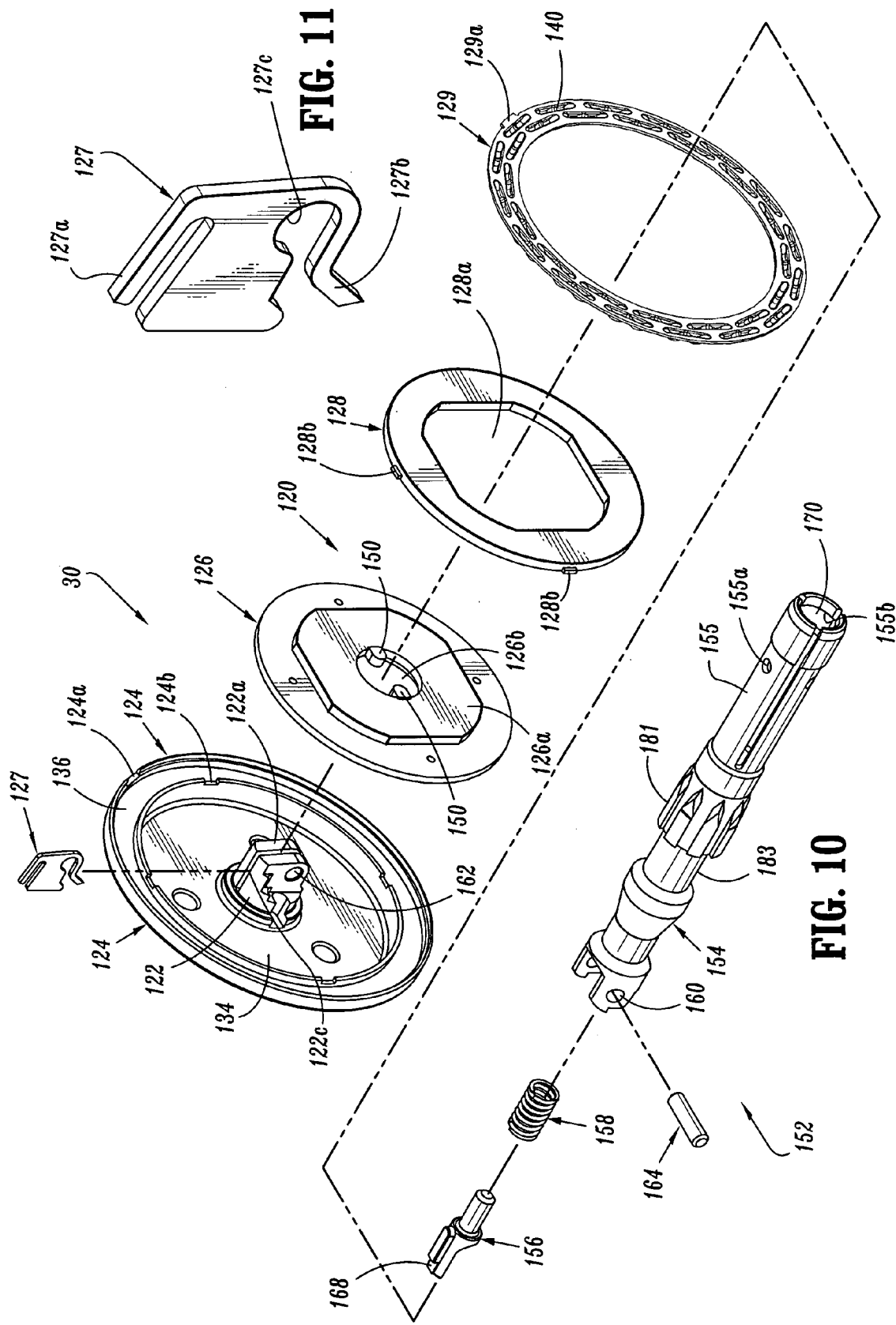

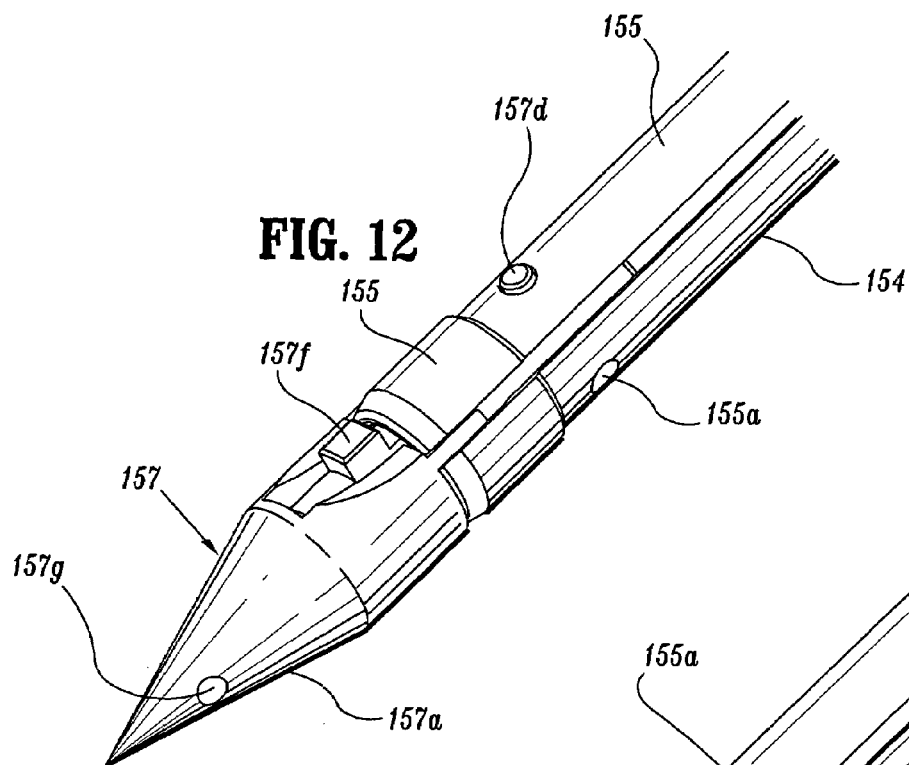
FIG. 12
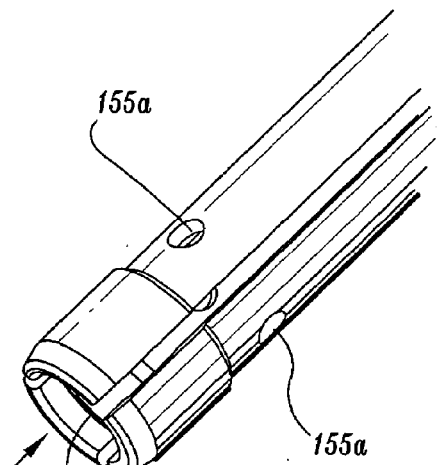
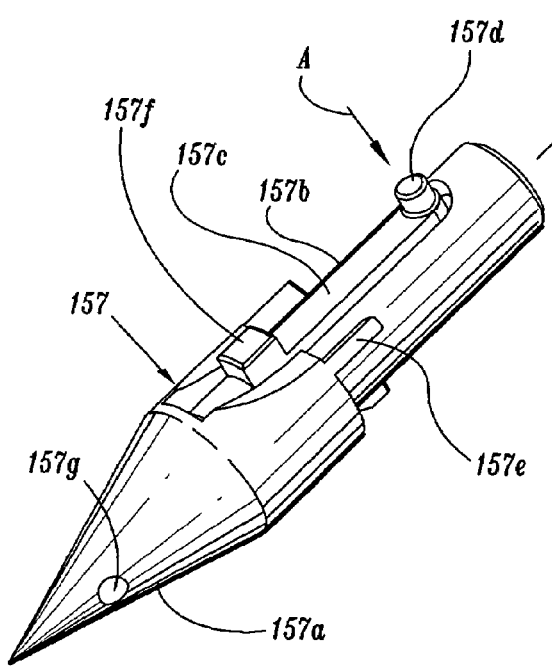
FIG. 13

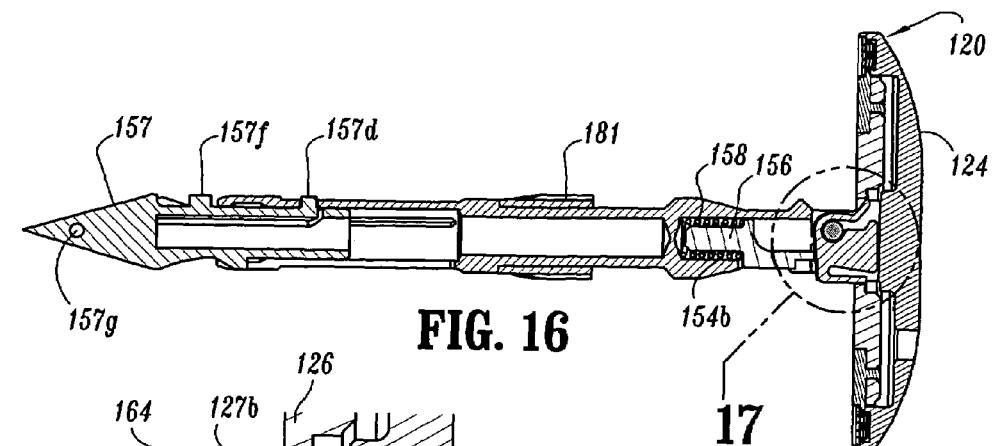
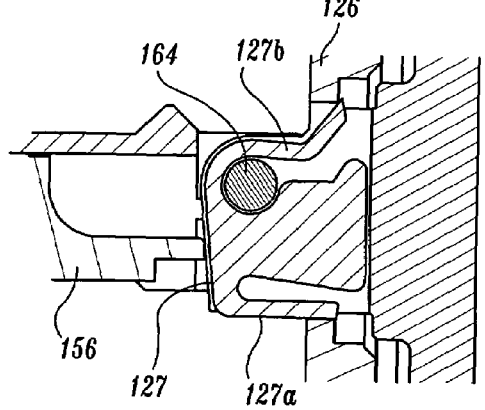
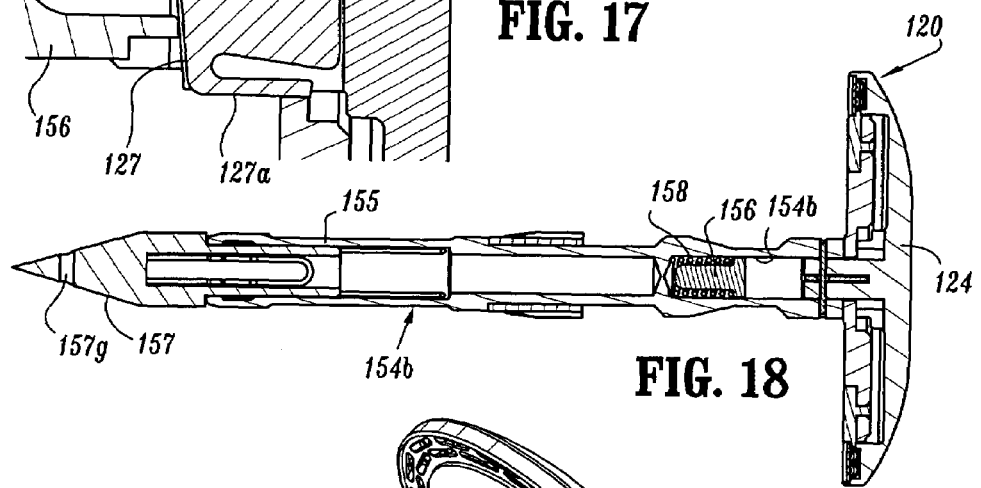
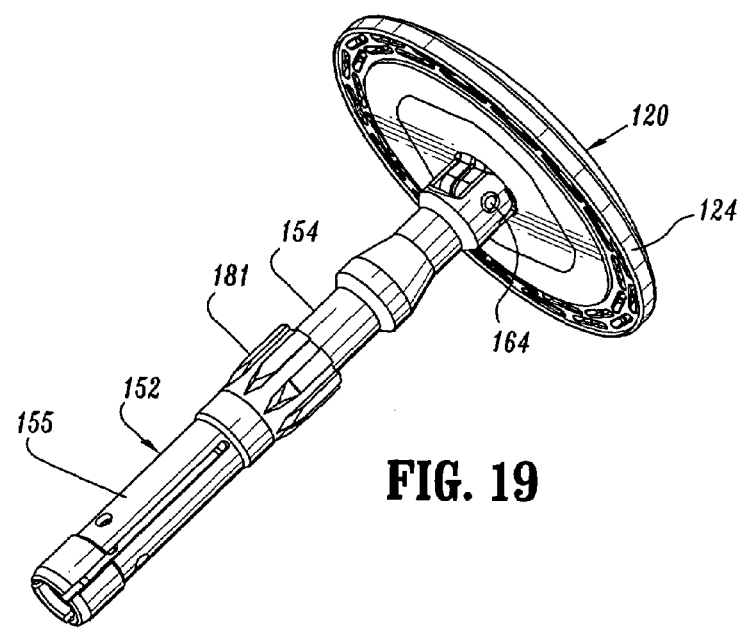

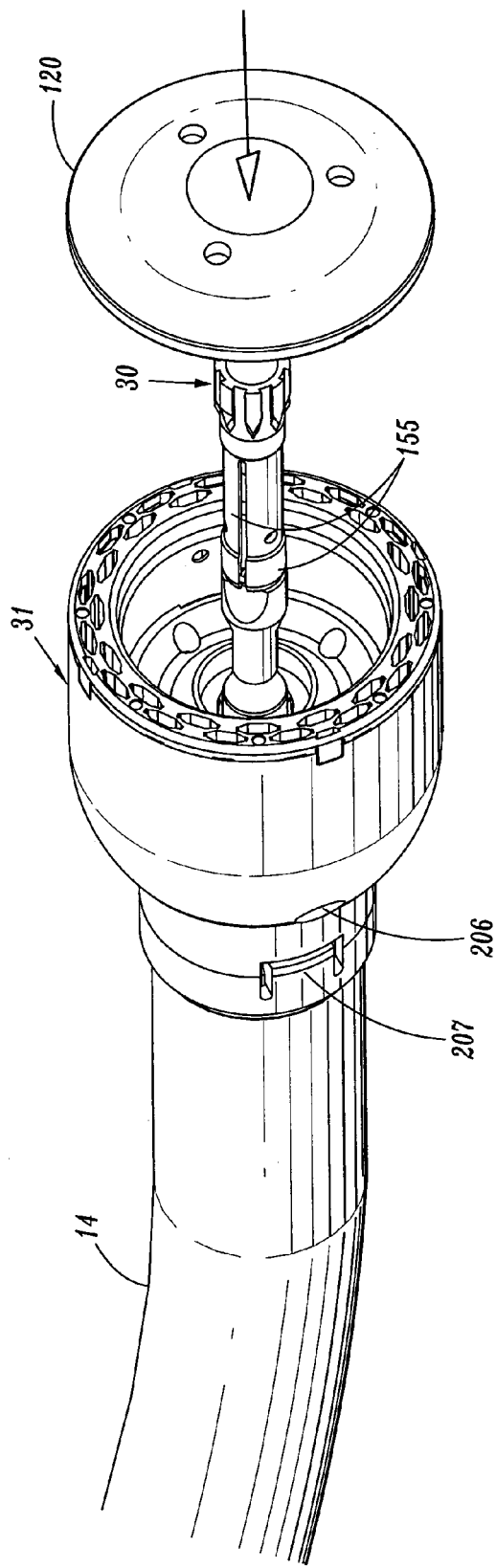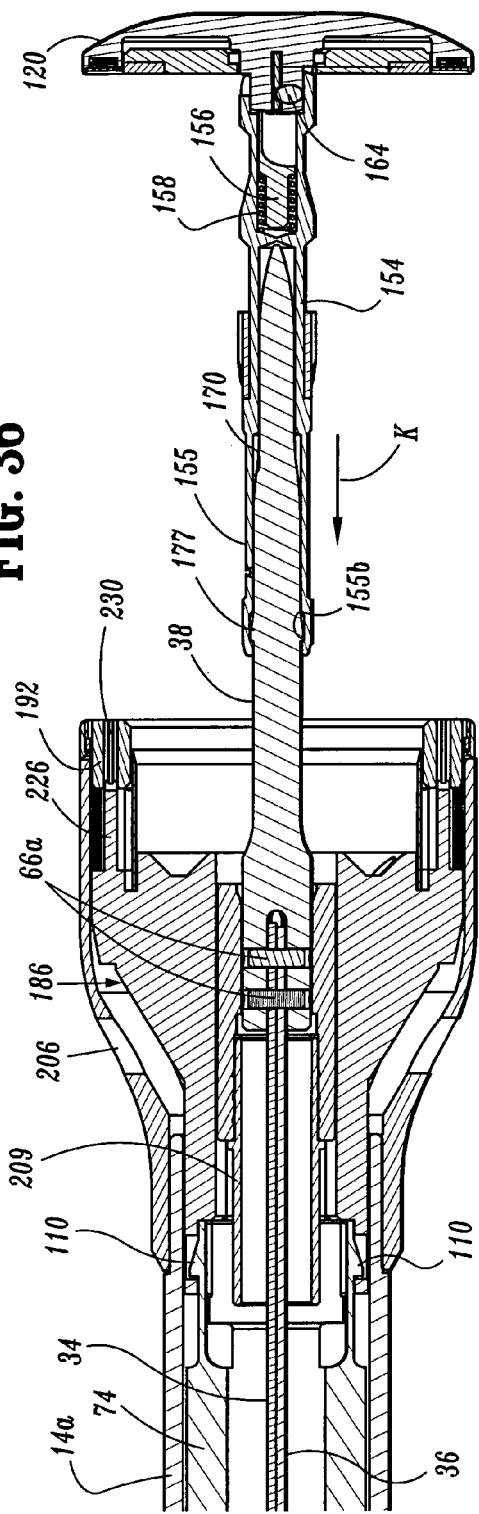
FIG. 36
FIG. 37

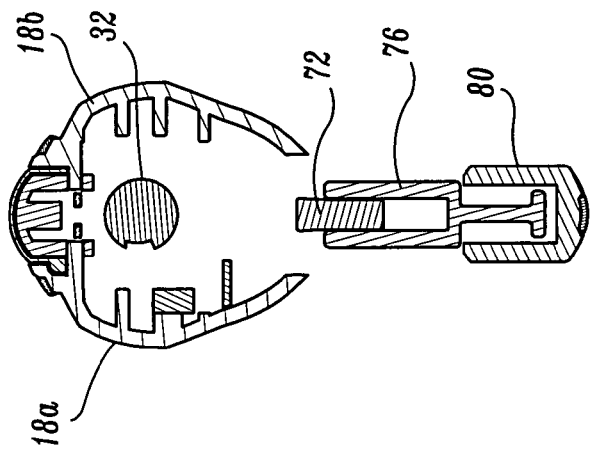
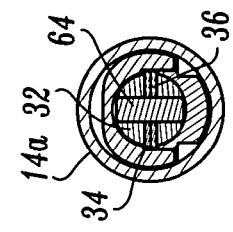
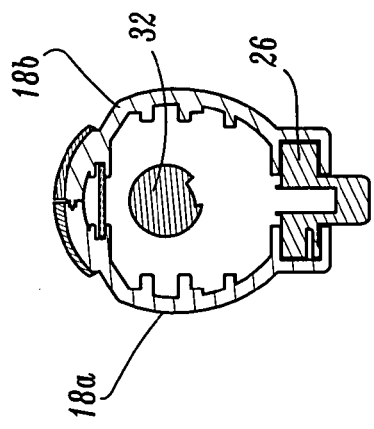
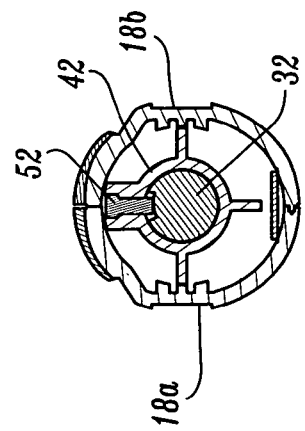
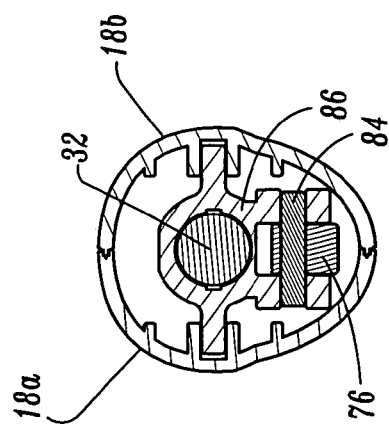

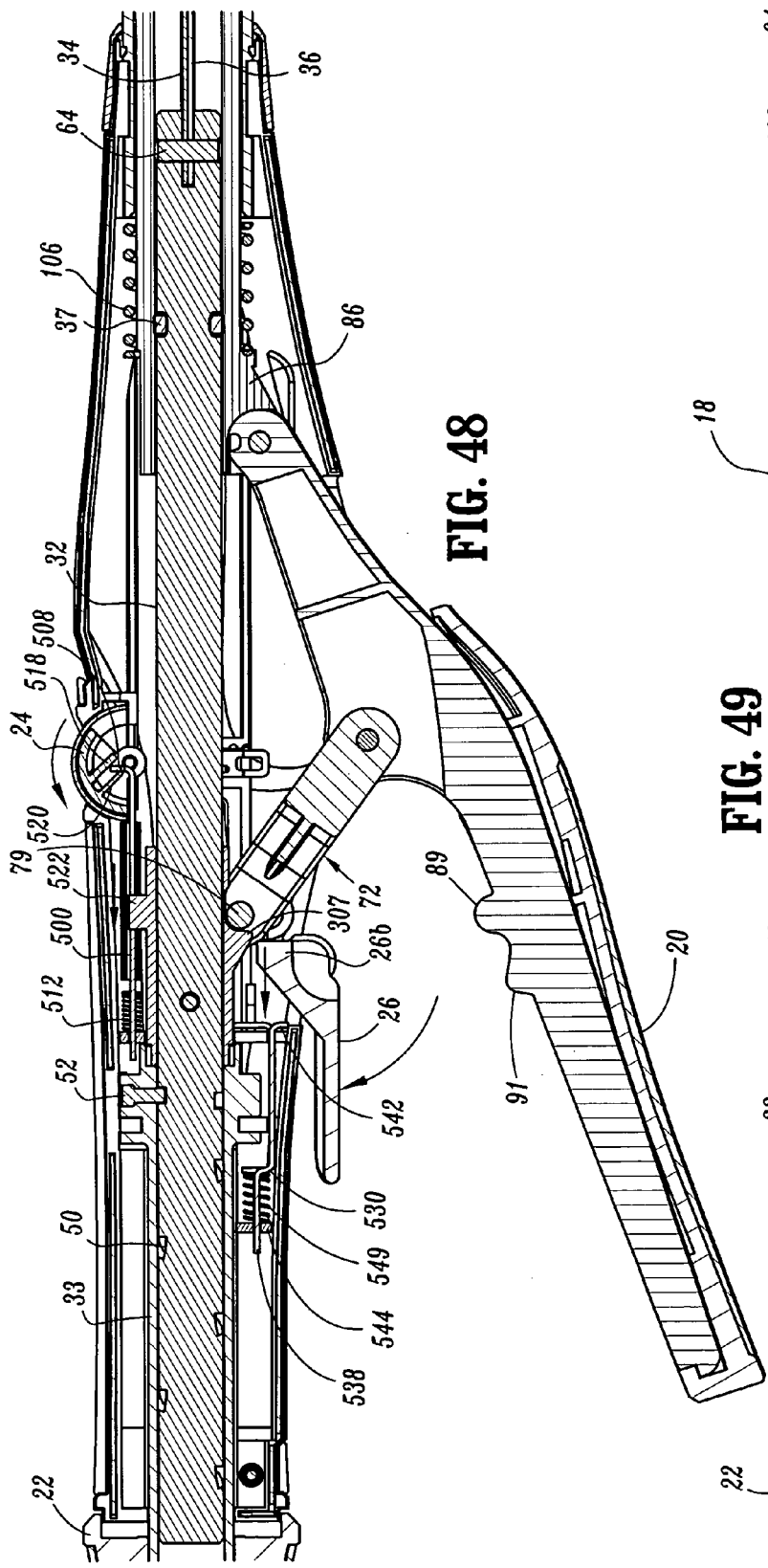
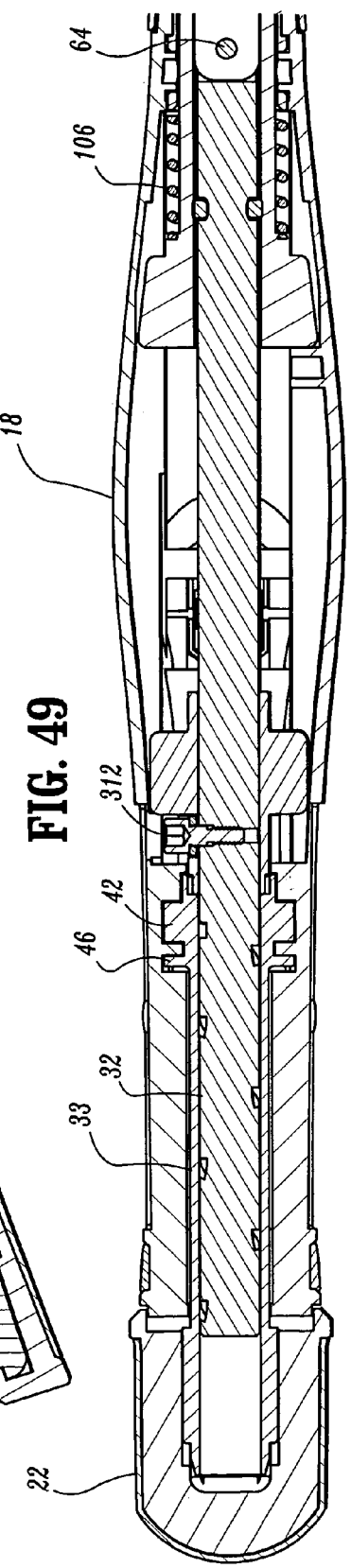
FIG. 48
FIG. 49

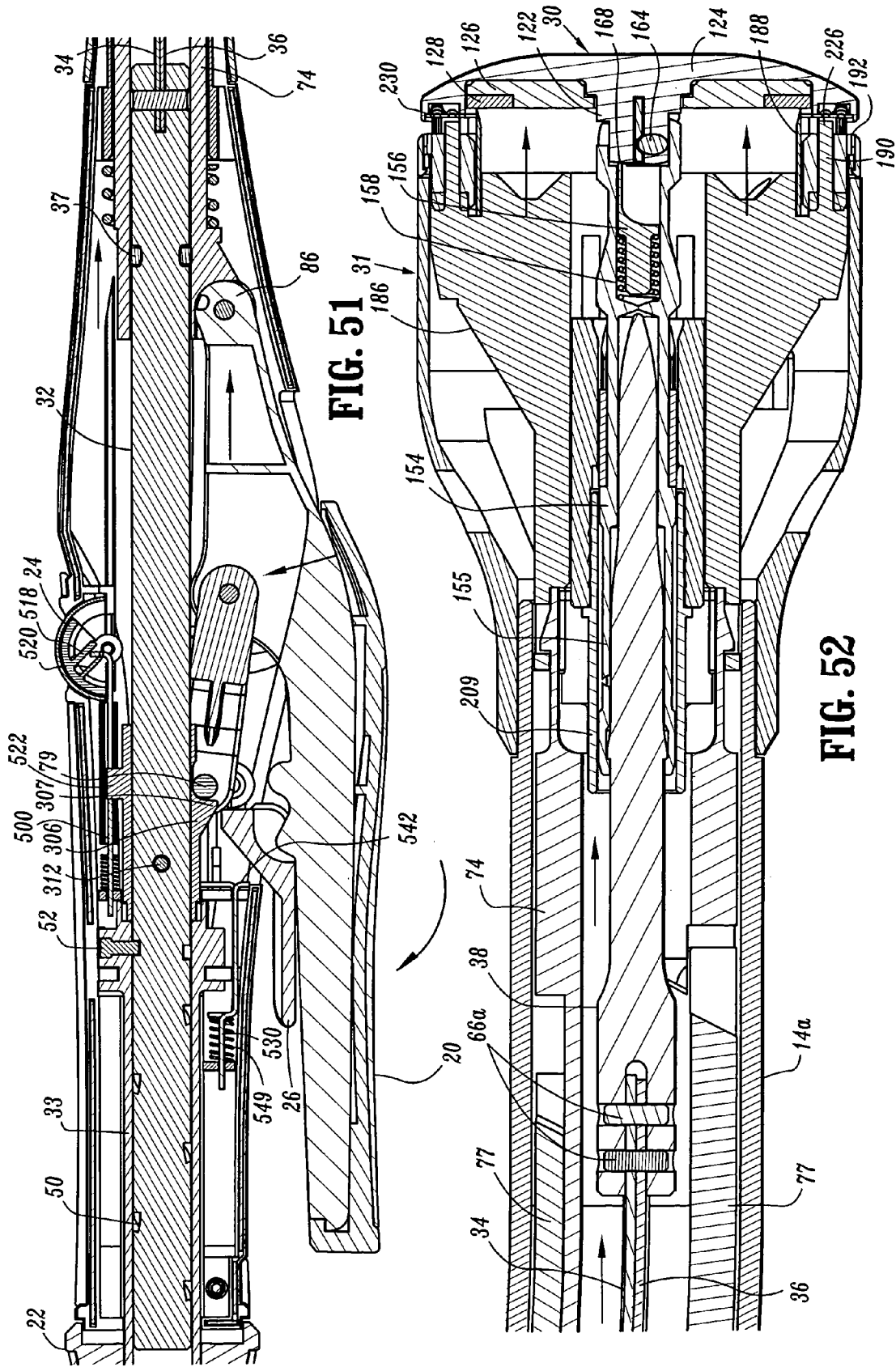

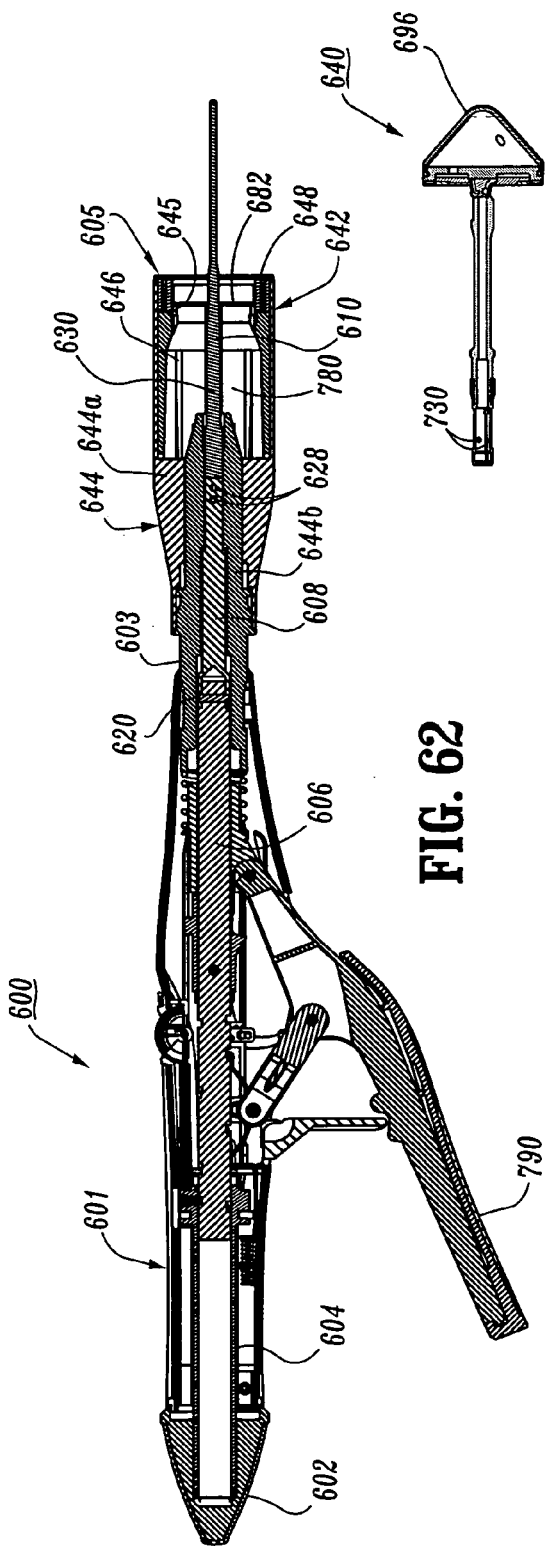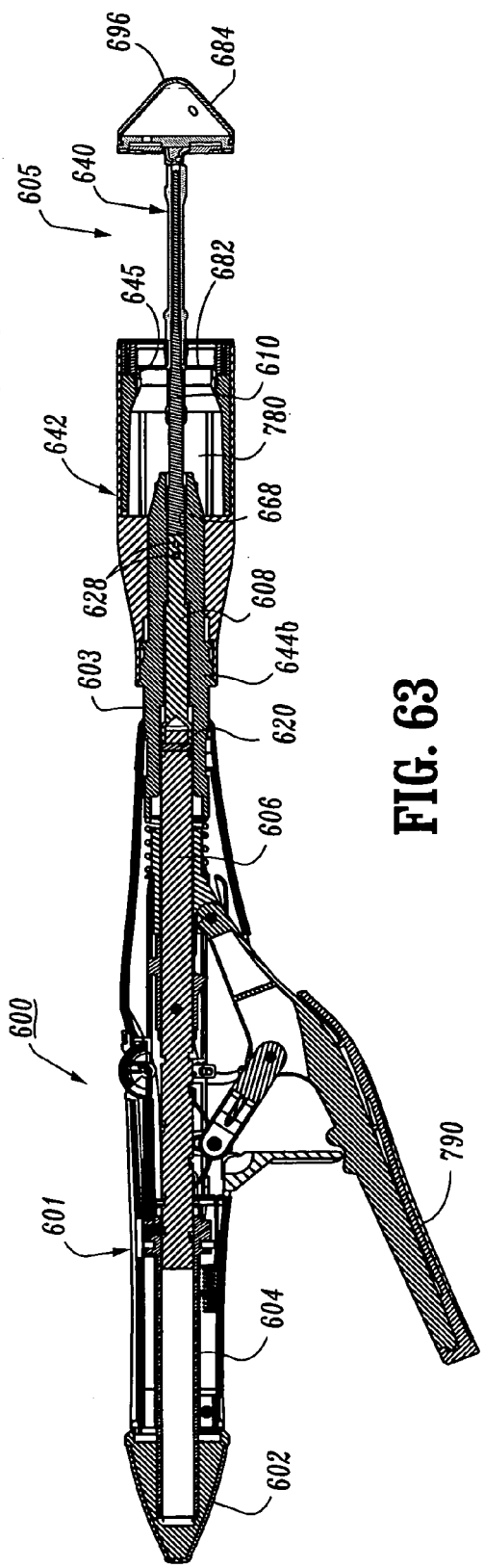

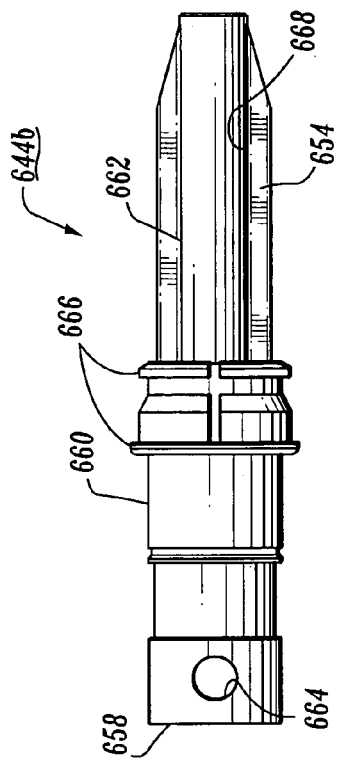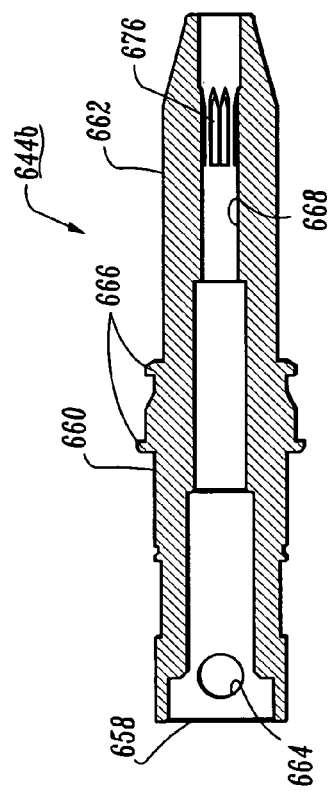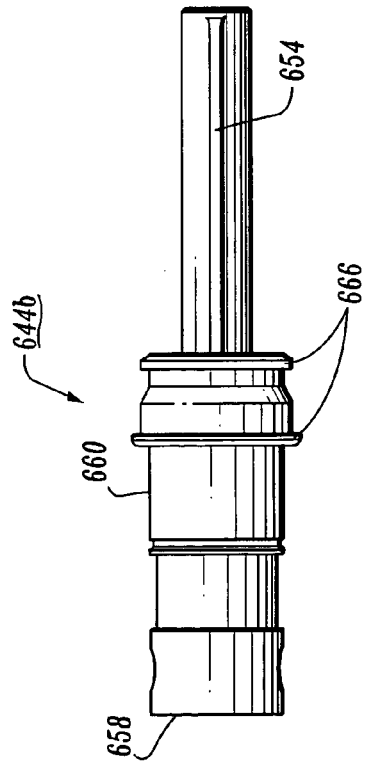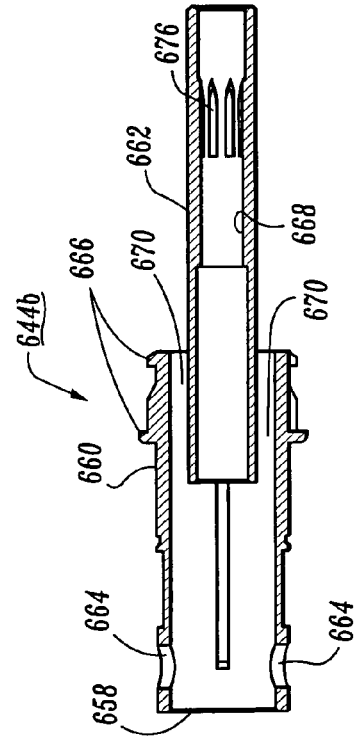
FIG. 76
FIG. 77
FIG. 78
FIG. 79

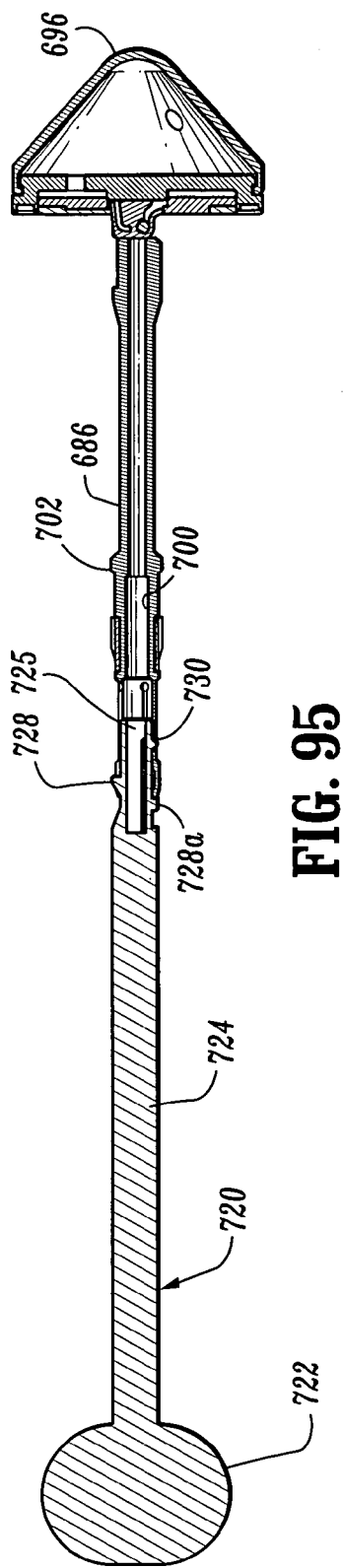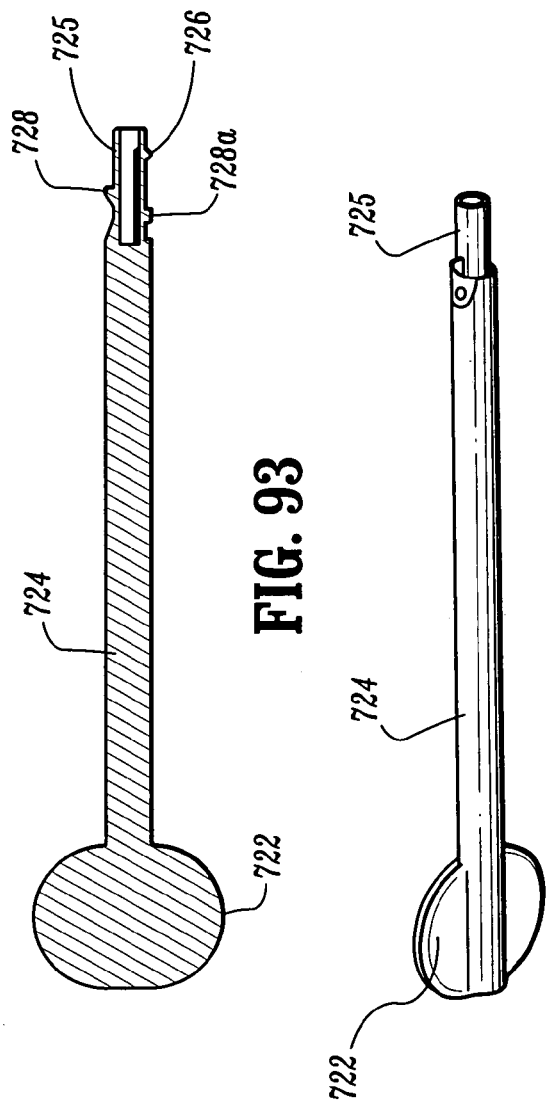
FIG. 95
FIG. 93
FIG. 94

SURGICAL STAPLING DEVICE

This application claims priority from U.S. provisional application Ser. No. 60/480,074, filed Jun. 20, 2003, the contents of which are incorporated by reference in their entirety.

BACKGROUND

1. Technical Field

The present disclosure relates generally to a surgical stapling device for applying surgical staples to body tissue. More particularly, the present disclosure relates to a surgical stapling device suitable for performing circular anastomosis and/or treatment to internal walls of hollow tissue organs.

2. Background of Related Art

Anastomosis is the surgical joining of separate hollow organ sections. Typically, an anastomosis procedure follows surgery in which a diseased or defective section of hollow tissue is removed and the remaining end sections are to be joined. Depending on the desired anastomosis procedure, the end sections may be joined by either circular, end-to-end or side-to-side organ reconstruction methods.

In a circular anastomosis procedure, the two ends of the organ sections are joined by means of a stapling instrument which drives a circular array of staples through the end section of each organ section and simultaneously cores any tissue interior of the driven circular array of staples to free the tubular passage. Examples of instruments for performing circular anastomsis of hollow organs are described in U.S. Pat. Nos. 6,053,390, 5,588,579, 5,119,983, 5,005,749, 4,646,745, 4,576,167, and 4,473,077, each of which is incorporated herein in its entirety by reference. Typically, these instruments include an elongated shaft having a handle portion at a proximal end to actuate the instrument and a staple holding component disposed at a distal end. An anvil assembly including an anvil rod with attached anvil head is mounted to the distal end of the instrument adjacent the staple holding component. Opposed end portions of tissue of the hollow organ(s) to be stapled are clamped between the anvil head and the staple holding component. The clamped tissue is stapled by driving one or more staples from the staple holding component so that the ends of the staples pass through the tissue and are deformed by the anvil head. An annular knife is concurrently advanced to core tissue with the hollow organ to free a tubular passage within the organ.

Besides anastomosis of hollow organs, surgical stapling devices for performing circular anastomosis have been used to treat internal hemorrhoids in the rectum. Typically, during use of a circular stapling device for hemorrhoid treatment, the anvil head and the staple holding component of the surgical stapling device are inserted through the anus and into the rectum with the anvil head and the staple holding component in an open or unapproximated position. Thereafter, a pursestring suture is used to pull the internal hemorrhoidal tissue towards the anvil rod. Next, the anvil head and the staple holding component are approximated to clamp the hemorrhoid tissue between the anvil head and the staple holding component. The stapling device is fired to remove the hemorrhoidal tissue and staple the cut tissue.

Using conventional circular anastomosis staplers to treat hemorrhoids has some difficulties. More specifically, because of the close proximity of the anvil head and staple holding component of the stapling device, visibility at the surgical site such as during placement of the pursestring suture is greatly impaired. Further, access to the surgical site is greatly restricted. As a result, it is difficult for a surgeon to effect proper placement of a pursestring suture into or adjacent hemorrhoidal tissue and also to verify that the pursestring suture has been properly placed and that the desired hemorrhoidal tissue is properly positioned for removal.

Accordingly, a continuing need exists in the art for a circular stapling device suitable for treatment of hemorrhoids or the like which provides improved visibility and access to the surgical site.

SUMMARY

In accordance with the present disclosure, a circular surgical stapling device for performing circular anastomosis and/or treating internal hemorrhoids is disclosed. The surgical stapling device includes a handle portion or assembly, a body portion and a head portion including an anvil assembly and a shell assembly. The handle portion can include a rotatable approximation knob for approximating the anvil and shell assemblies and a firing trigger for actuating a firing mechanism for ejecting staples positioned within the shell assembly. In one embodiment, the firing trigger forms one link of a two bar linkage provided to actuate the firing mechanism. The two bar linkage provides the device with an improved mechanical advantage to reduce the firing forces required to fire the device.

In one embodiment, the head portion includes an anvil assembly including a tiltable anvil which will tilt automatically when the device has been fired and unapproximated. The tiltable anvil provides a reduced anvil profile to reduce trauma during removal of the device after the anastomosis procedure has been performed.

The surgical stapling device may also include a firing lockout mechanism which prevents actuation of the firing trigger until the device has been approximated. In one embodiment, the firing lockout mechanism includes a trigger lock and a lockout member which is movably positioned in the handle assembly. The lockout member prevents movement of the trigger lock from a locked to an unlocked position until the device has been approximated.

In one embodiment, the surgical stapling device includes tactile indication mechanism. The tactile indication mechanism indicates to a surgeon that the anvil head has been unapproximated a distance sufficient to permit the anvil head to tilt, thus, indicating that the device can be removed from the patient.

In another embodiment, the stapling device includes a bulbous indicator which extends above a top surface of the handle assembly of the device. The indicator includes indicia to identify to a surgeon that the device has been approximated and is in a fire-ready position. The indicator may include a cover which is formed of a magnification material to prominently display the indicia. The presently disclosed indicator provides improved visualization of the indicator to a surgeon from both the top and sides of the instrument.

In another embodiment, the anvil assembly of the stapling device includes a retainer clip positioned on the anvil head. The retainer clip includes at least one resilient arm which is positioned to engage a cutting ring in its unbiased position to prevent the cutting ring from sticking to a knife blade during unapproximation of the stapling device. The retainer clip may include a pair of resilient arms which are positioned in a transverse slot in an anvil post of the anvil assembly. The cutting ring is positioned about the anvil post to urge the resilient arms into the transverse slot. The cutting ring is movable about the anvil post when the device is fired to allow the resilient arms of the retainer clip to flex outwardly to a position obstructing proximal movement of the cutting ring.

In yet another embodiment, the surgical stapling device includes an approximation mechanism including an anvil retainer having an elongated distal extension which is telescopingly received within a longitudinal bore formed in the anvil center rod of the anvil assembly. The elongated distal extension may have a reduced diameter as compared to the proximal portion of the anvil retainer. The elongated distal extension should be of a length to facilitate telescopic engagement of the anvil retainer and anvil center rod without obstructing visualization of a surgical site. In one embodiment, the anvil retainer includes an engagement surface or shoulder for releasably engaging the anvil center rod. The shoulder is positioned proximally of the elongated distal extension. The approximation mechanism may also include a retainer extension member positioned between an approximation screw and the anvil retainer.

In another embodiment, the surgical stapling device is included in a surgical kit suitable for treating internal hemorrhoids. The kit includes a surgical stapling device and a removable anvil assembly. In one embodiment, the surgical stapling device includes an anvil retainer having an elongated distal extension. The kit may also include an insertion handle which is adapted to releasably engage the anvil assembly to position the anvil assembly at a surgical site. The kit may also include a speculum, an anal dialator and/or an obturator.

BRIEF DESCRIPTION OF THE DRAWINGS

Various embodiment of the presently disclosed surgical stapling device are disclosed herein with reference to the drawings, wherein:

FIG. 1 is a top side perspective view from the proximal end of the presently disclosed surgical stapling device in the unapproximated position;

FIG. 2 is a top side perspective view from the distal end of the surgical stapling device shown in FIG. 1;

FIG. 3 is a side perspective exploded view of the handle assembly of the surgical stapling device shown in FIG. 1;

FIG. 3A is a top perspective view of the indicator of the handle assembly shown in FIG. 3;

FIG. 6 is a side perspective exploded view of the central body portion and distal head portion of the surgical stapling device shown in FIG. 1;

FIG. 7 is an enlarged side perspective of the anvil retainer and band portions of the central body portion shown in FIG. 6;

FIG. 8 is a side perspective view of the screw and screw stop of the approximation mechanism of the handle assembly shown in FIG. 5;

FIG. 10 is a side perspective exploded view from the proximal end of the anvil assembly of the surgical stapling device shown in FIG. 1;

FIG. 11 is a side perspective view of the retaining clip of the anvil assembly shown in FIG. 10;

FIG. 12 is a side perspective view of the distal end of the center rod of the anvil assembly shown in FIG. 10 with a removable trocar fastened thereto;

FIG. 13 is a side perspective view of the center rod and removable trocar shown in FIG. 11 separated one from the other;

FIG. 16 is a side cross-sectional view taken through the retaining clip of the anvil assembly and removable trocar of the anvil assembly shown in FIG. 15;

FIG. 17 is an enlarged view of the indicated area of detail shown in FIG. 16;

FIG. 18 is a side cross-sectional view taken through the pivot member of the anvil head assembly of the anvil assembly shown in FIG. 15;

FIG. 19 is a side perspective view from the proximal end of the anvil assembly shown in FIG. 18 with the removable trocar removed;

FIG. 36 is a perspective view from the front of the distal end of the surgical stapling device shown in FIG. 35 with an anvil assembly attached thereto;

FIG. 37 is a side cross-sectional view of the distal end of the surgical stapling device shown in FIG. 36;

FIG. 39 is a cross-sectional view taken along section lines 39—39 of FIG. 38;

FIG. 40 is a cross-sectional view taken along section lines 40—40 of FIG. 38;

FIG. 41 is a cross-sectional view taken along section lines 41—41 of FIG. 38;

FIG. 42 is a cross-sectional view taken along section lines 42—42 of FIG. 38;

FIG. 43 is a cross-sectional view taken along section lines 43—43 of FIG. 38;

FIG. 44 is a cross-sectional view taken along section lines 44—44 of FIG. 38;

FIG. 48 is a side cross-sectional view of the handle assembly of the surgical stapling device shown in FIG. 45;

FIG. 49 is a top horizontal cross-sectional view of a portion of the handle assembly of the surgical stapling device shown in FIG. 45;

FIG. 51 is a side cross-sectional view of a portion of the handle assembly of the surgical stapling device shown in FIG. 45 after the firing trigger has been actuated;

FIG. 52 is a side cross-sectional view of the distal end of the surgical stapling device shown in FIG. 45 after the firing trigger has been actuated;

FIG. 62 is a side cross-sectional view of another embodiment of the presently disclosed surgical stapling device with the anvil assembly removed from the anvil retainer;

FIG. 63 is a side cross-sectional view of the surgical stapling device shown in FIG. 62 with the anvil assembly attached to the anvil retainer in the open position;

FIG. 64 is a side cross-sectional view of the anvil assembly of the surgical stapling device shown in FIG. 63;

FIG. 76 is a side view of the inner guide portion of the shell assembly of the surgical stapling device shown in FIG. 65;

FIG. 77 is a top view of the inner guide portion of the shell assembly shown in FIG. 76;

FIG. 78 is a side cross-sectional view of the inner guide portion of the shell assembly shown in FIG. 77;

FIG. 79 is a top cross-sectional view of the inner guide portion of the shell assembly shown in FIG. 77;

FIG. 93 is a side cross-sectional view of an anvil assembly insertion handle;

FIG. 94 is a side perspective view of the anvil assembly insertion handle shown in FIG. 93;

FIG. 95 is a side cross-sectional view of the anvil assembly insertion handle attached to the anvil assembly shown in FIG. 84;

DETAILED DESCRIPTION OF EMBODIMENTS

Figure 4:
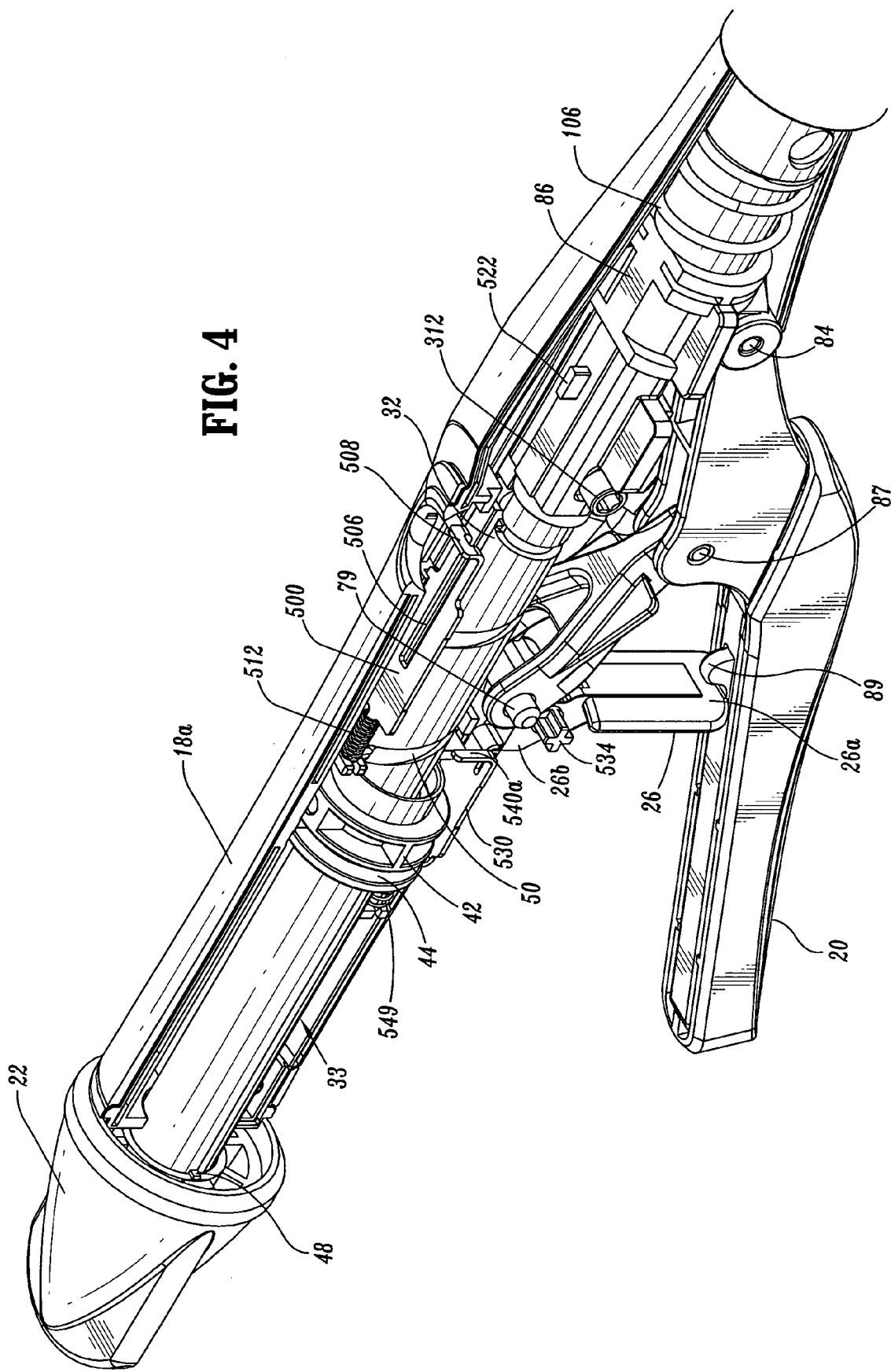
FIG. 4 is a side perspective view from the top of the handle assembly of the surgical stapling device shown in FIG. 1 with a handle section removed.

Embodiments of the presently disclosed surgical stapling device will now be described in detail with reference to the drawings in which like reference numerals designate identical or corresponding elements in each of the several views.

Throughout this description, the term "proximal" will refer to the portion of the instrument closest to the operator and the term "distal" will refer to the portion of the instrument furthest from the operator.

FIGS. 1 and 2 illustrate one embodiment of the presently disclosed surgical stapling device shown generally as 10. Briefly, surgical stapling device 10 includes a proximal handle assembly 12, an elongated central body portion 14 including a curved elongated outer tube 14a, and a distal head portion 16. Alternately, in some surgical procedures, e.g., the treatment of hemorrhoids, it is desirable to have a substantially straight central body portion. The length, shape and/or the diameter of body portion 14 and head portion 16 may also be varied to suit a particular surgical procedure.

Handle assembly 12 includes a stationary handle 18, a firing trigger 20, a rotatable approximation knob 22 and an indicator 24. Stationary handle 18 may be formed from thermoplastic handle sections 18a and 18b, e.g., polycarbonate, (FIG. 3) which together define a housing for the internal components of handle assembly 12. Handle sections 18a and 18b may be secured together by sonic welding. Alternately, other known securement techniques may be employed including screws, adhesives, snap-fit connectors, etc. The internal components of handle portion 12 will be discussed in detail below. In one embodiment, cushioned and/or resilient slip resistant portions such as a grip (not shown) can be fastened to or included as part of handle sections 18a and 18b and firing trigger 20. The slip resistant grip may be formed over handle sections 18a and 18b and firing trigger 20 using an overmolding procedure and may be formed from Neoprene polychloroprene or rubber. Alternately, other suitable, e.g., elastomeric, materials and joining techniques may be employed. A pivotally mounted trigger lock 26 is fastened to handle assembly 12 and is manually positioned to prevent inadvertent firing of stapling device 10. Indicator 24 is positioned on the stationary handle 18 and includes indicia, e.g., color coding, alpha-numeric labeling, etc., to identify to a surgeon whether the device has been fired and/or when the device is ready to be fired.

Head portion 16 includes an anvil assembly 30 and a shell assembly 31. Each of these assemblies will be discussed in detail below. Except where otherwise noted, the components of surgical device 10 are formed from thermoplastics including polycarbonates, and metals including stainless steel and aluminum. The particular material selected to form a particular component will depend upon the strength requirements of the particular component. For example, the anvil may be formed from a metal, such as stainless steel, and the stationary handle may be formed from a thermoplastic such as polycarbonate. Alternately, other materials not listed above, which can withstand sterilization procedures, may be used to form components of stapling device 10 provided the materials are suitable for surgical use and meet the strength requirements of the particular component.

Figure 5:
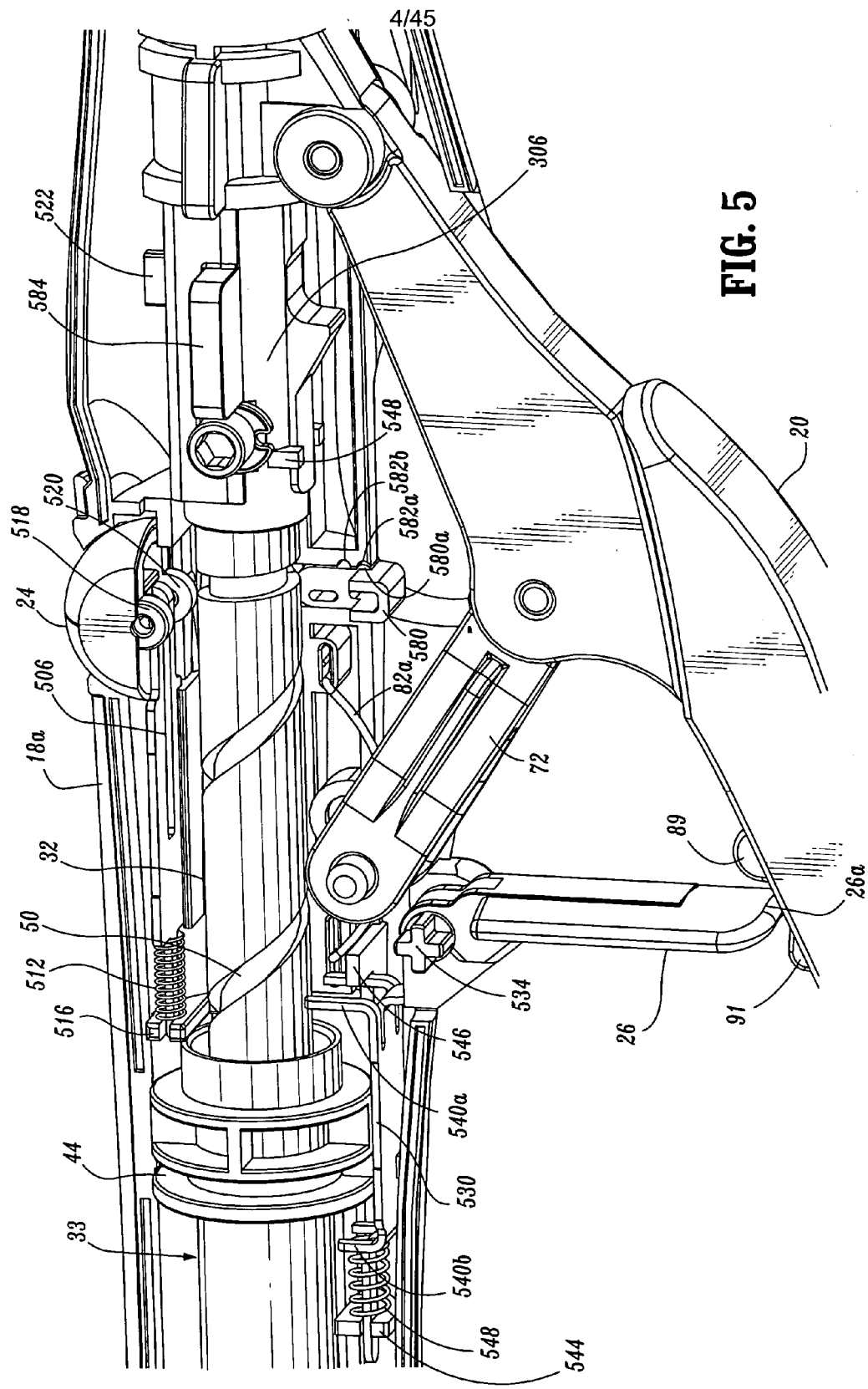
FIG. 5 is a side perspective view from the bottom of the handle assembly of the surgical stapling device shown in FIG. 4.
Figure 9A:
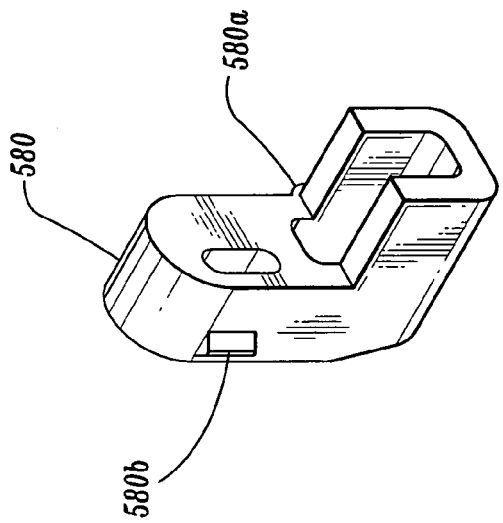
FIG. 9A is a side perspective view from the top of the abutment member of the handle assembly shown in FIG. 3.
Figure 9:
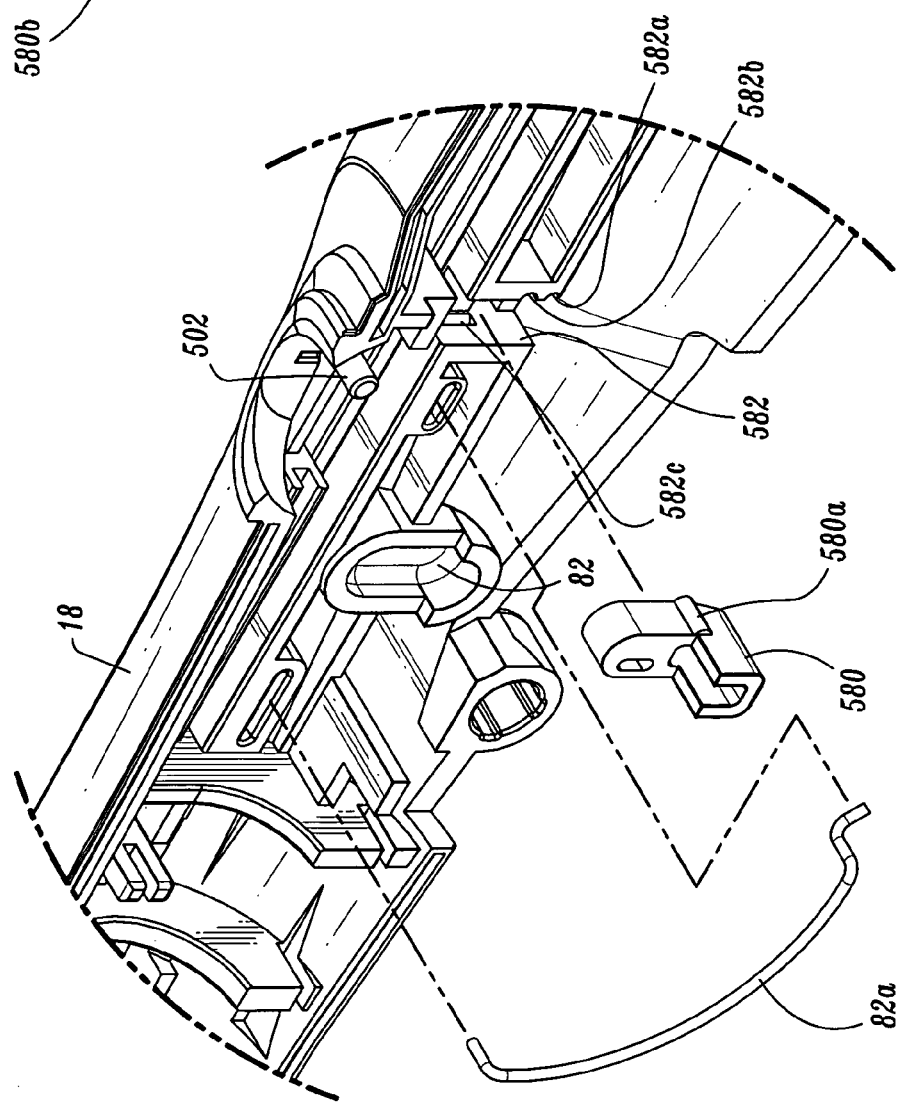
FIG. 9 is an enlarged view of the indicated area of detail shown in FIG. 3.
Figure 14:
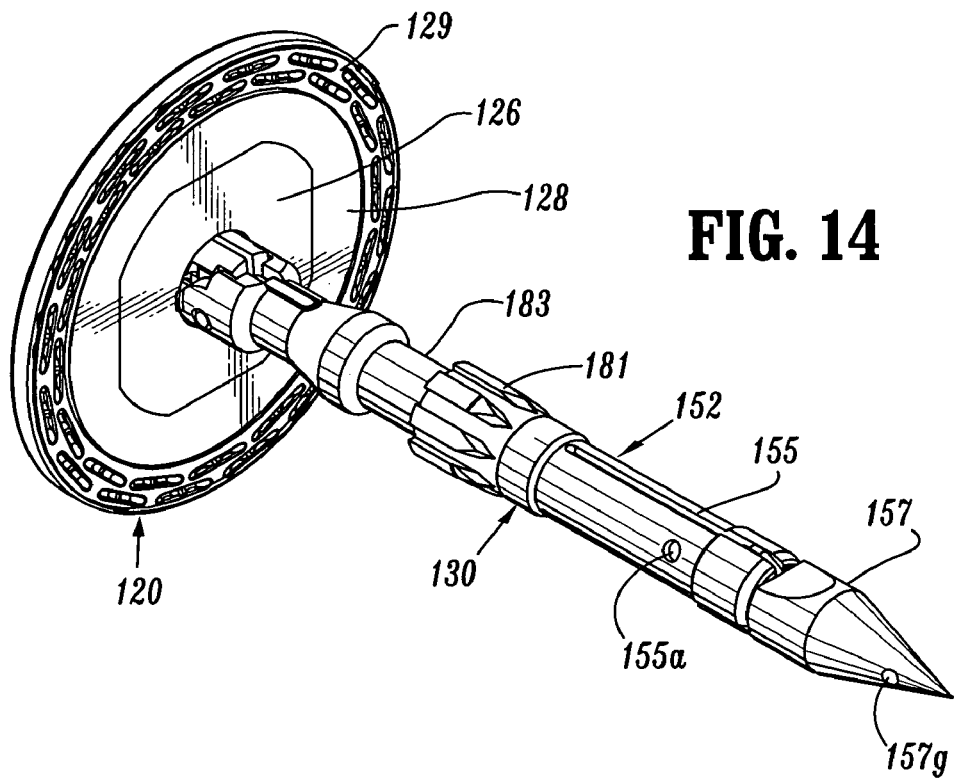
FIG. 14 is a side perspective view from the proximal end of the anvil assembly shown in FIG. 10 with the removable trocar attached thereto.
Figure 15:
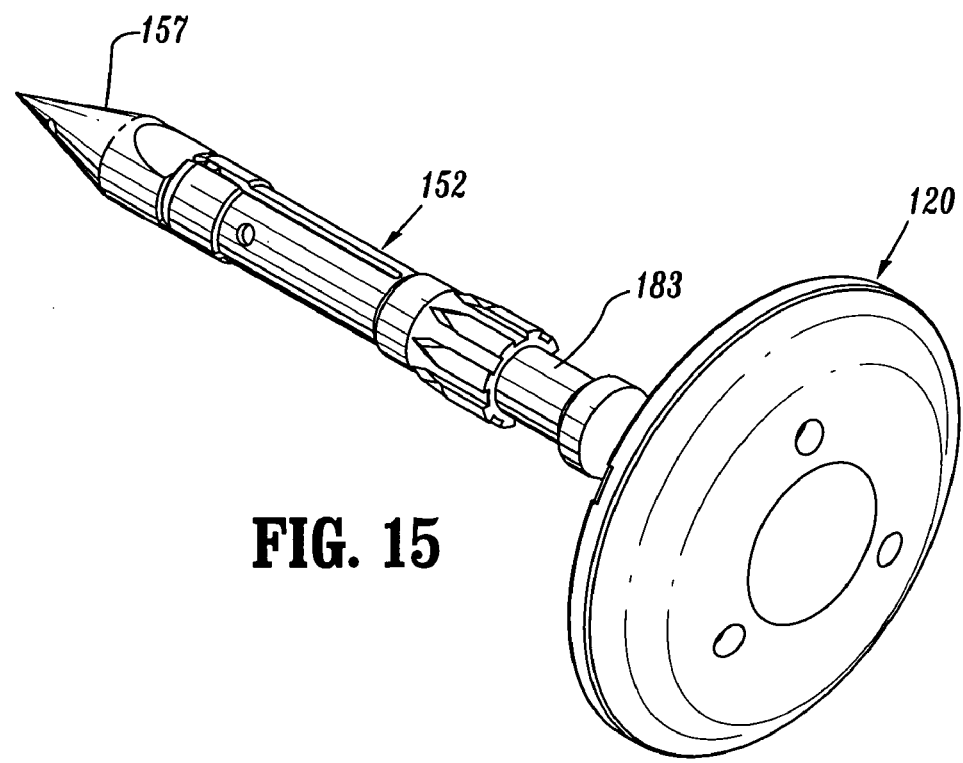
FIG. 15 is a side perspective view from the distal end of the anvil assembly shown in FIG. 14.
Figure 21:
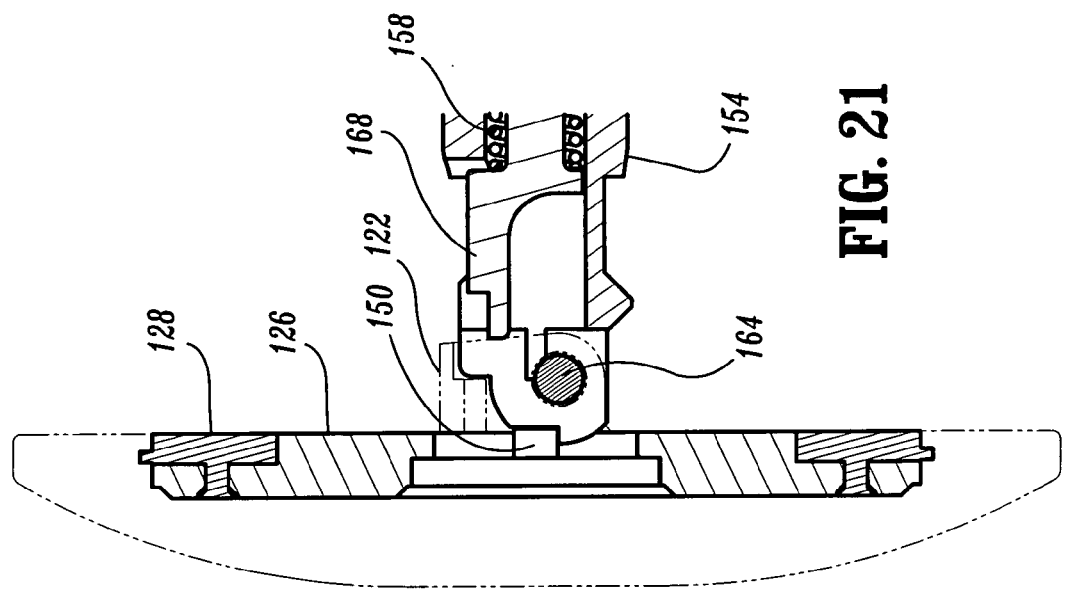
FIG. 21 is a side cross-sectional partial cutaway view of the distal portion of the anvil assembly shown in FIG. 19, with the anvil head in phantom.
Figure 20:
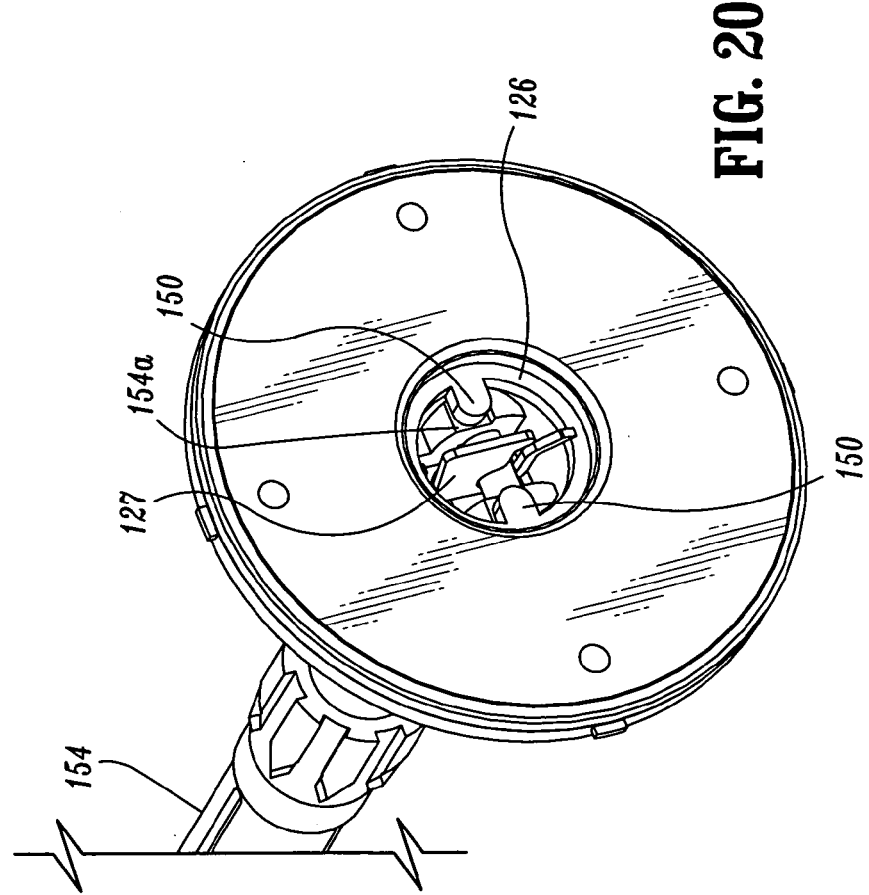
FIG. 20 is a perspective, partial cutaway view from the distal end of the anvil assembly shown in FIG. 19, with the anvil head removed.
Figure 22:
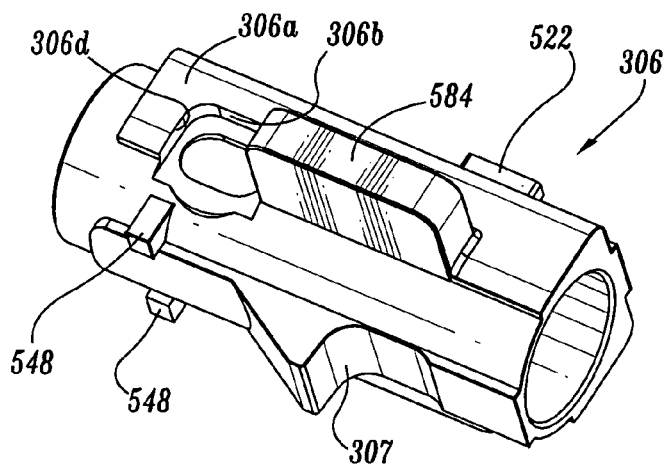
FIG. 22 is a side perspective view from the bottom of the screw stop of the handle assembly shown in FIG. 3.
Figure 23:
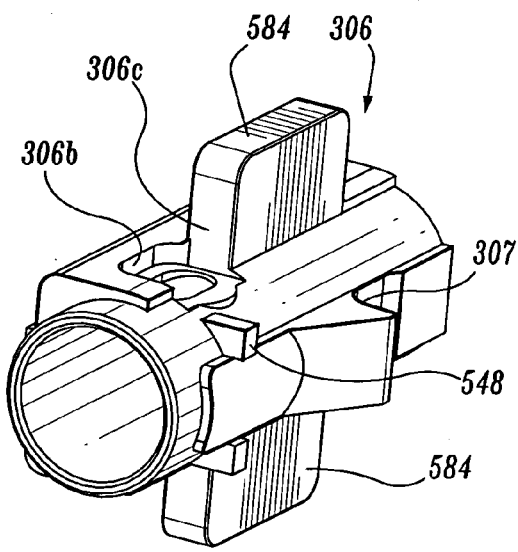
FIG. 23 is a bottom perspective view from the proximal end of the screw stop shown in FIG. 22.
Figure 24:
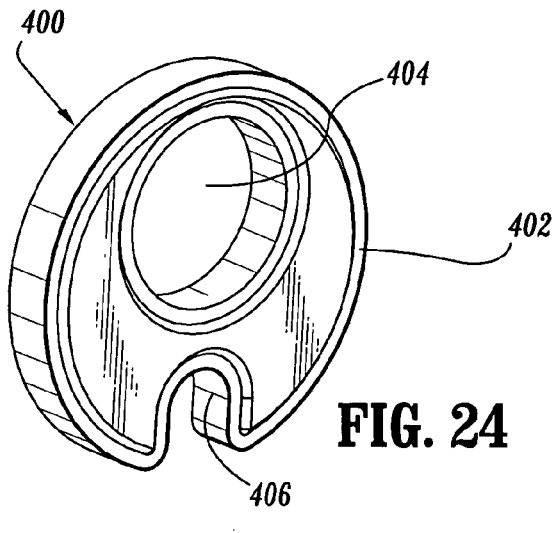
FIG. 24 is a top perspective view of the cam adjustment member of the handle assembly shown in FIG. 3.

FIGS. 3–5 illustrate the internal components of handle assembly 12. The internal components include the proximal components of approximation and firing mechanisms, a firing lockout mechanism and an indicator drive mechanism. FIGS. 6 and 7 illustrate the internal components of elongated body portion 14. These components include the distal components of the approximation and firing mechanisms. Each of these mechanisms will be disclosed in detail hereinbelow.

Approximation Mechanism

Referring to FIGS. 3–8, the approximation mechanism includes approximation knob 22, a rotatable sleeve 33, a drive screw 32, first and second screw extensions 34 and 36 (FIG. 6), and an anvil retainer 38. Rotatable sleeve 33 includes a substantially cylindrical hollow body portion 40 and a substantially cylindrical collar 42 which together define a central bore 33a. Collar 42 has an annular groove 44 formed thereabout and is dimensioned to receive an inwardly extending flange 46 formed on an inner wall of stationary handle 18. Engagement between groove 44 and flange 46 axially fixes sleeve 33 within handle 18 while permitting rotation of sleeve 33 in relation to stationary handle 18. The proximal end of body portion 40 of rotatable sleeve 33 extends through an opening 18b in the proximal end of stationary handle 18. A pair of diametrically opposed elongated ribs 48 are positioned on the outer surface of body portion 40. Approximation knob 22 includes a pair of internal slots 49a positioned to receive ribs 48 of sleeve 33 to rotatably fix sleeve 33 to knob 22, such that rotation of knob 22 causes concurrent rotation of sleeve 33.

The proximal half of screw 32 includes a helical channel 50 and is dimensioned to be slidably positioned within central bore 33a of rotatable sleeve 33. The distal end of screw 32 includes an annular recess 35 dimensioned to receive a seal member 37 (FIG. 3) for providing a fluid tight seal between the outer surface of screw 32 and the inner surface of pusher link 74 (FIG. 6). A pin 52 (FIG. 3) extends radially through body portion 42 of sleeve 33 into helical channel 50. Since sleeve 33 is axially fixed with respect to stationary handle 18, rotation of sleeve 33 about screw 32 causes pin 52 to move along channel 50 of screw 32 to effect axial movement of screw 32 within stationary handle 18.

The distal end of screw 32 includes a transverse slot 54. Top and bottom screw extensions 34 and 36 (FIG. 6) each include a proximally located flexible flat band portion 58 and a distally located flat band portion 60. Alternately, it is envisioned that screw extensions 34 and 36 may have other than a band configuration. For example, screw extensions 34 and 36 may be semi-circular or circular in cross-section. The flexibility of top and bottom screw extensions 34 and 36 permits movement of screw extensions 34 and 36 through curved elongated body portion 14. The proximal end of each band portion 58 includes a hole 62 dimensioned to receive a pin 64 for securing the proximal end of screw extensions 34 and 36 within transverse slot 54 of screw 32. Alternately, other fastening techniques may be used to secure each band portion 58 to screw 32, e.g., welding, crimping, etc. Distally located band portion 60 of each screw extension 34 and 36 is dimensioned to be received within a transverse slot 66 formed in a proximal end of anvil retainer 38 (FIG. 7) to fasten anvil retainer 38 to the distal end of screw extensions 34 and 36. In one embodiment, a pair of pins 66*a* which extend through the proximal end of anvil retainer 38 and band portions 60 are used to secure screw extensions 34 and 36 to anvil retainer 38. Alternately, band portions 60 can be brazed or welded within slot 66 or other fastening techniques may be used to secure band portions 60 of screw extensions 34 and 36 to anvil retainer 38, e.g., screws, crimping, etc. Anvil retainer 38 includes an annular protrusion 177 (FIG. 7) which is configured to engage the anvil assembly in a manner to be discussed in detail below. Alternately, protrusion 177 need not be annular or may include different attachment structure, e.g., recesses, grooves, etc.

In operation, when approximation knob 22 is manually rotated, rotatable sleeve 33 is rotated about the proximal end of screw 32 to move pin 52 along helical channel 50 of screw 32. Since sleeve 33 is axially fixed to stationary handle 18, as pin 52 is moved through channel 50, screw 32 is advanced or retracted within stationary handle 18. As a result, top and bottom screw extensions 34 and 36, which are fastened to the distal end of screw 32, and anvil retainer 38, which is fastened to the distal end of screw extensions 34 and 36, are moved axially within elongated body portion 14. Since anvil assembly 30 is secured to the distal end of anvil retainer 38, rotation of approximation knob 22 will effect movement of anvil assembly 30 in relation to shell assembly 31 between spaced and approximated positions.

Firing Mechanism

Referring to FIGS. 3–6 and 9, the firing mechanism includes firing trigger 20, a firing link 72 and an elongated pusher link 74 (FIG. 6). Firing trigger 20 includes a body portion 76 and a trigger cover 80. A cushioned gripping surface (not shown) which may be formed of Neoprene polychloroprene or rubber is provided on trigger cover 80. The cushioned gripping surface provides a non-slip cushioned surface to make actuation of device 10 more comfortable and less traumatic to a surgeon. Body portion 76 of trigger 20 is pivotally connected to a coupling member 86 (which is secured to the proximal end of pusher link 74), by a pivot member 84. Coupling member 86 may be formed integrally with pusher link 74 or as a separate element fastened thereto. Firing link 72 has a first end pivotally secured to body portion 76 of trigger 20 by a pivot member 87 and a second end pivotally secured within a vertical slot 82 formed between stationary handle half-sections 18*a* and 18*b* of stationary handle 18 by pivot member 79. Pivot member 79 is free to move vertically within slot 82. A spring 82*a* (FIG. 9) is supported within handle 18 to urge pivot member 79 downwardly towards the bottom of slot 82. Body portion 76 further includes a pair of abutments including an abutment 89 and an abutment 91 which are positioned to engage the distal end 26*a* (FIG. 4) of trigger lock 26 in a manner to be described in greater detail below to prevent actuation of trigger 20 prior to approximation of device 10.

Coupling member 86 which is supported on the proximal end of elongated pusher link 74 includes a flange 104 (FIG. 6). A spring 106, positioned between an inner wall or abutment within stationary handle 18 and flange 104, biases pusher link 74 proximally to a retracted, non-fired position. A pair of wings 108 extend radially outwardly from coupling member 86. Wings 108 are dimensioned to slide along channel 111 (FIG. 3) formed along the internal walls of stationary handle 18 to maintain proper alignment of pusher link 74 within stationary handle 18 during firing of device 10.

The distal end of pusher link 74 includes a pair of engagement fingers 110 which are dimensioned to lockingly engage with members 220 formed in the proximal end of pusher back 186. Pusher back 186 forms part of shell assembly 31 and will be discussed in greater detail below. Pusher link 74 may be formed from a flexible plastic material and includes a plurality of notches 187 which allow the pusher link to bend more easily as it moves through body 14. Pusher link 74 defines a hollow channel 75 for slidably receiving the approximation mechanism. A flat surface or cutout 74*a* formed in pusher link 74 slidably supports screw extensions 34 and 36 which are positioned in juxtaposed alignment one on top of the other. Spacers 77 are positioned within outer tube 14*a* adjacent cutout 74*a* to provide additional support for screw extensions 34 and 36 and pusher link 74 and prevent each component from buckling during actuation. An annular channel 74*b* is formed about pusher link 74 to receive an O-ring seal 74*c*. Pusher link 74 is slidably positioned within body portion 14 such that O-ring 74*c* seals the space between pusher link 74 and an internal wall of outer tube 14*a*. Operation of the firing mechanism of the device will be described in detail below.

Figure 25:
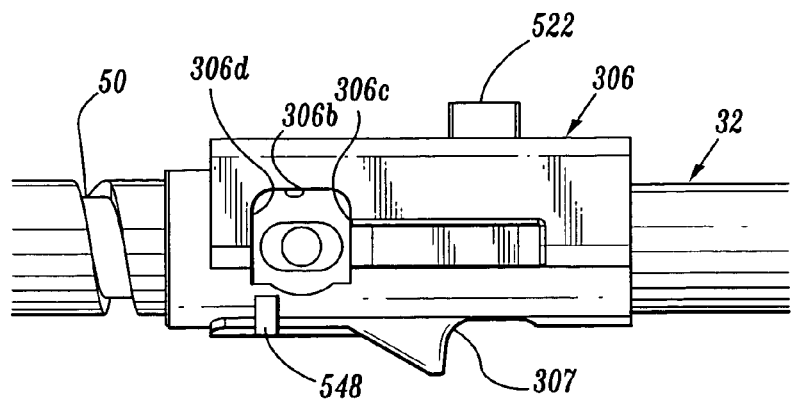
FIG. 25 is a side view of the screw and screw stop of the handle assembly shown in FIG. 3 with the set screw and the cam adjustment member removed.
Figure 26:
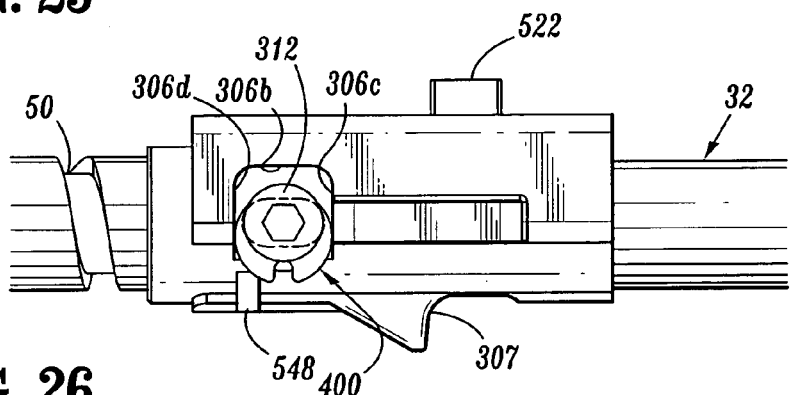
FIG. 26 is a side view of the screw and screw stop shown in FIG. 25 with the set screw and cam adjustment member attached thereto.
Figure 27:
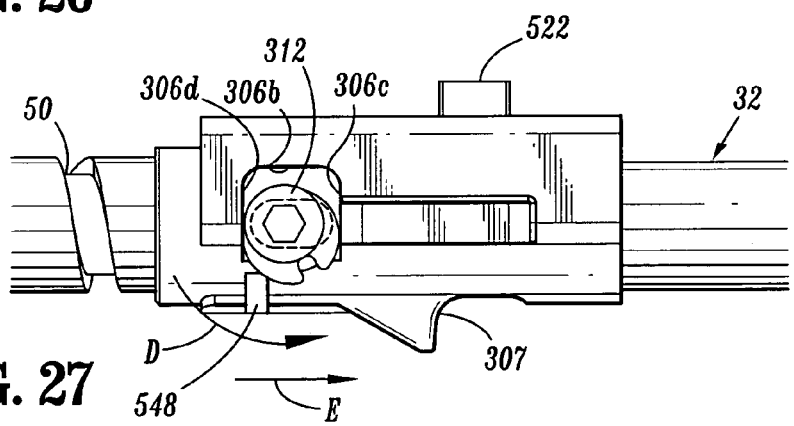
FIG. 27 is a side view of the screw and screw stop shown in FIG. 26 with the cam adjustment screw adjusted to increase the tissue gap.
Figure 28:
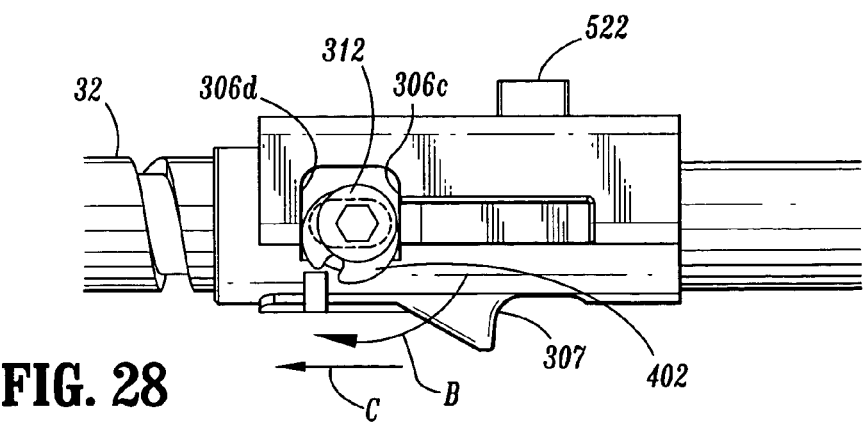
FIG. 28 is a side view of the screw and screw stop shown in FIG. 26 with the cam adjustment screw adjusted to decrease the tissue gap.
Figure 29:
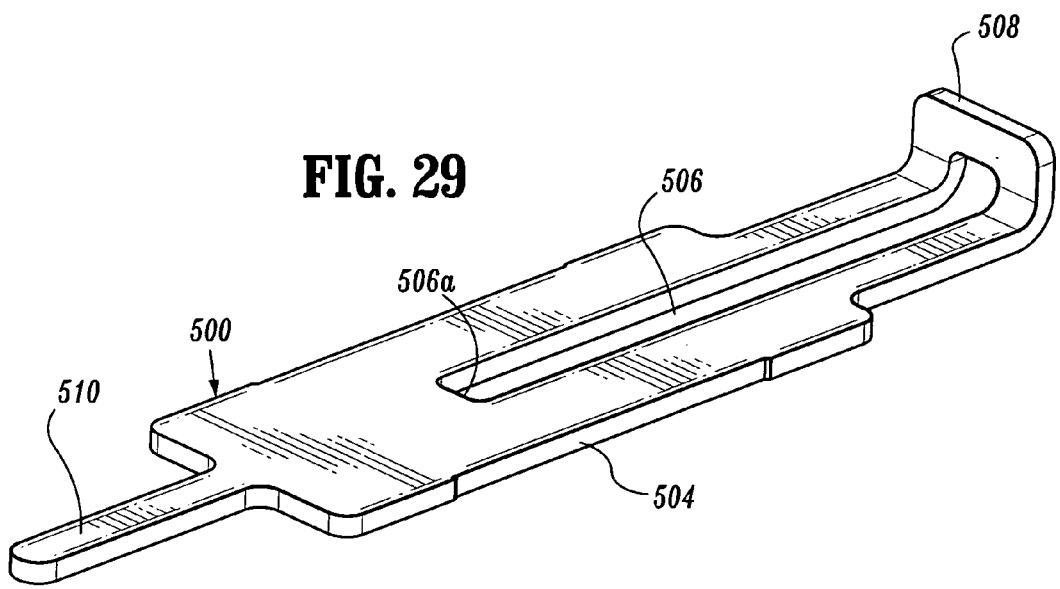
FIG. 29 is a top perspective view from the proximal end of the slide member of the indicator mechanism of the handle assembly shown in FIG. 3.
Figure 30:
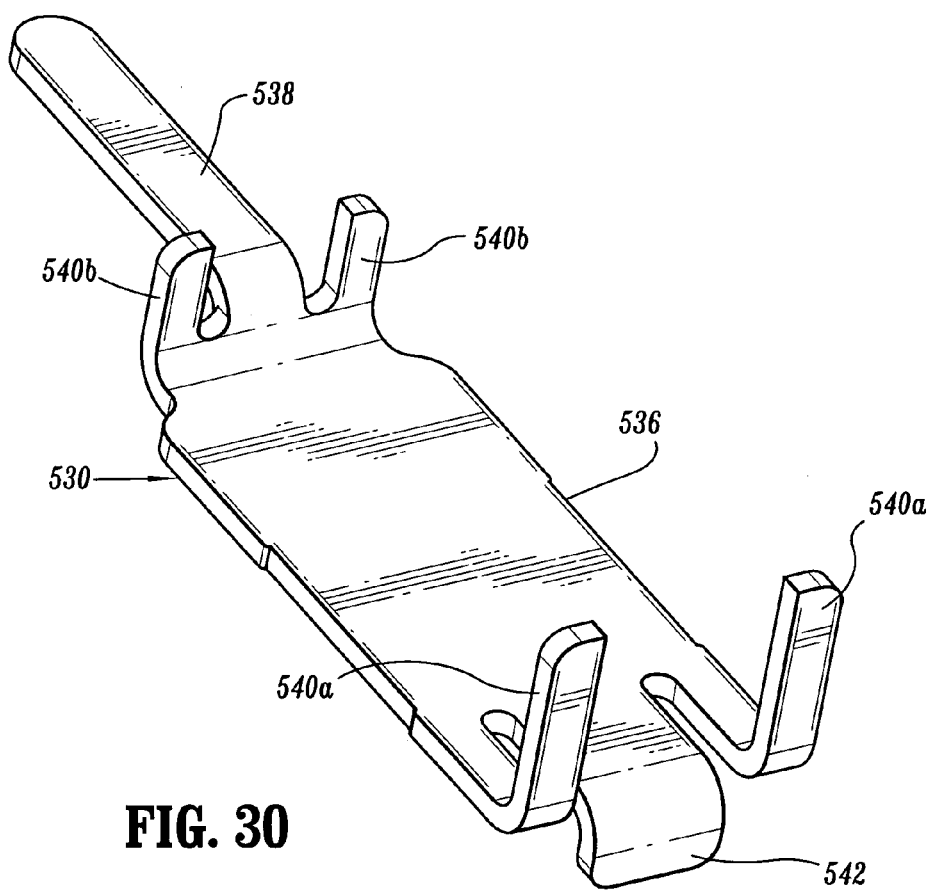
FIG. 30 is a bottom perspective view of the lockout member of the fire lockout mechanism of the handle assembly shown in FIG. 3.
Figure 31:
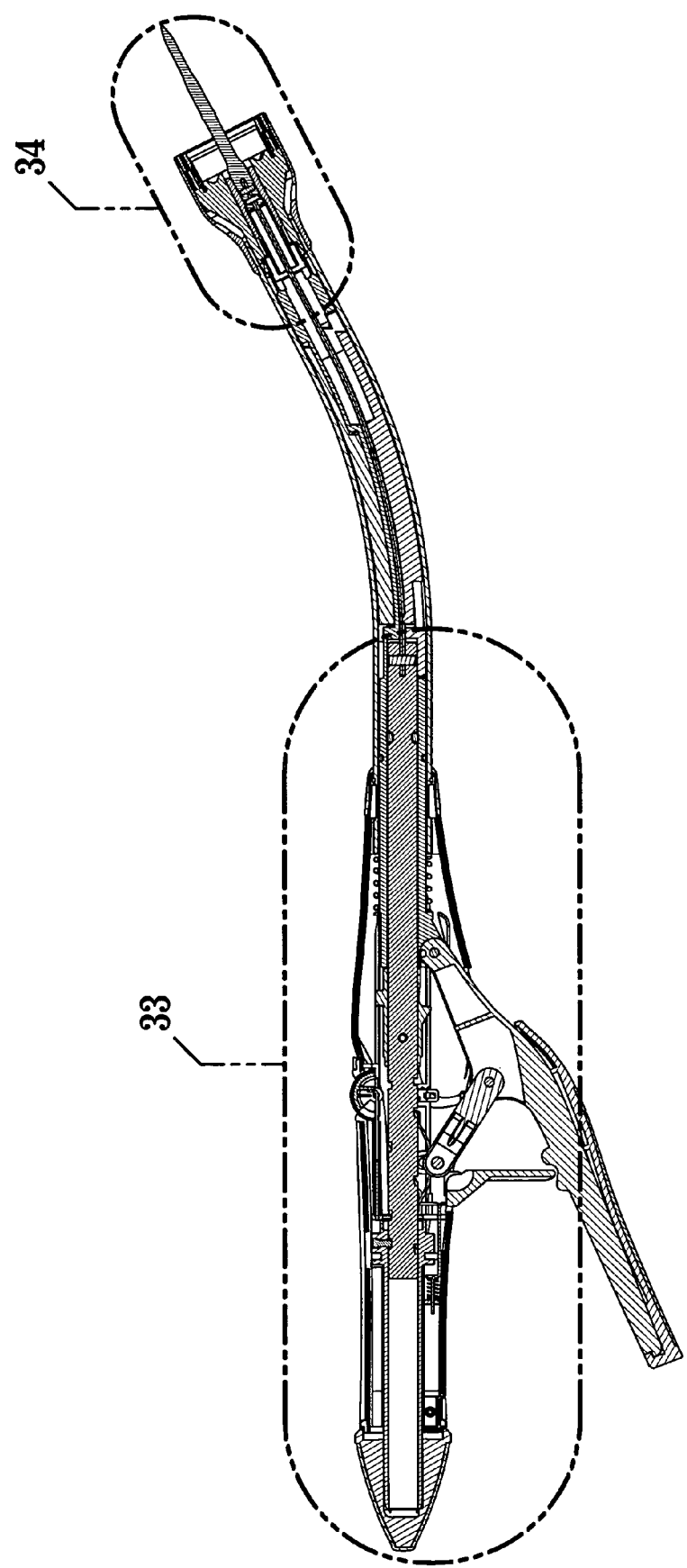
FIG. 31 is a side cross-sectional view of the surgical stapling device shown in FIG. 1 with the anvil assembly removed.
Figure 32:
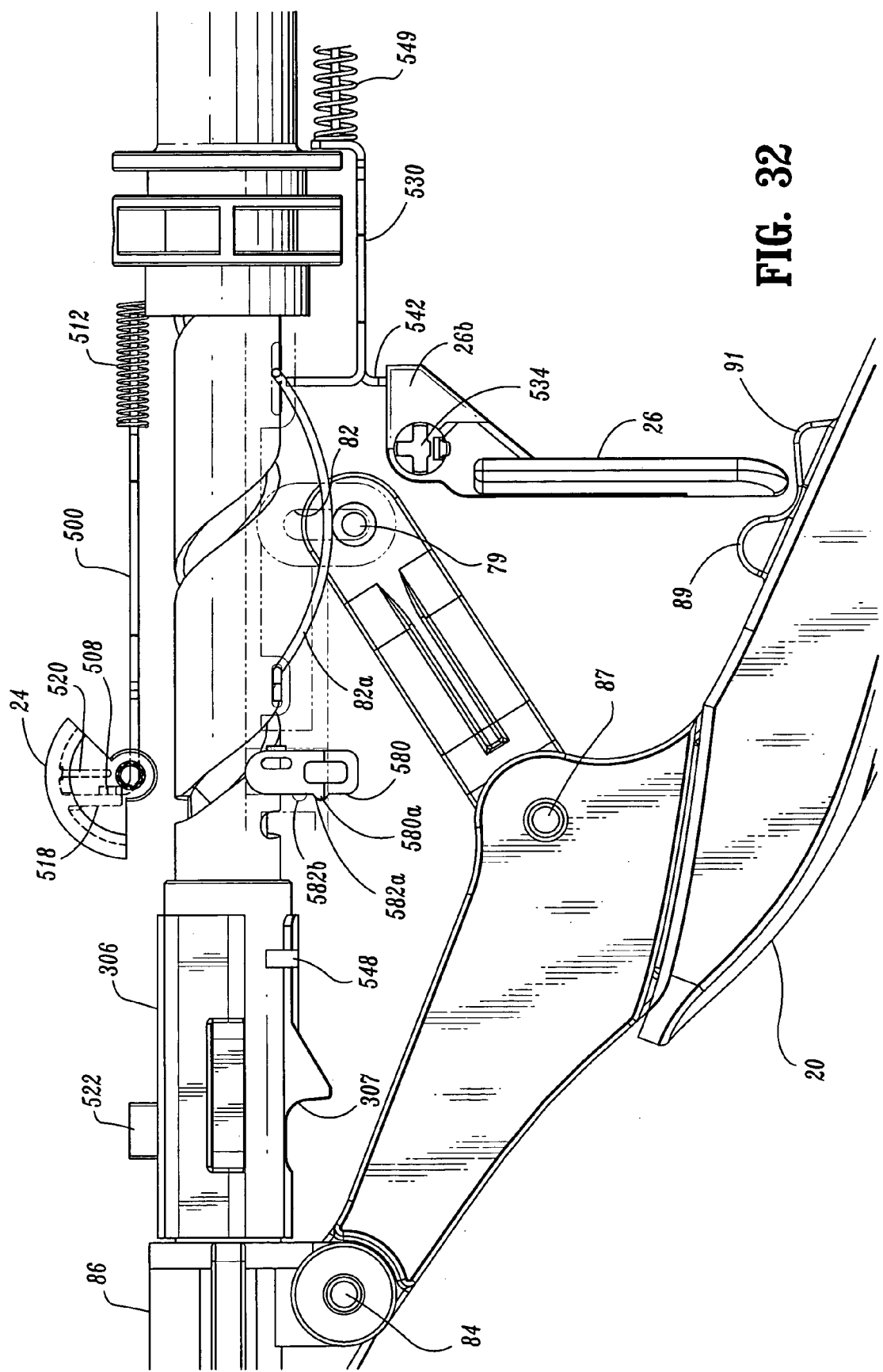
FIG. 32 is a side enlarged view of the handle assembly of the surgical stapling device shown in FIG. 31 with the handle sections removed.
Figure 33:
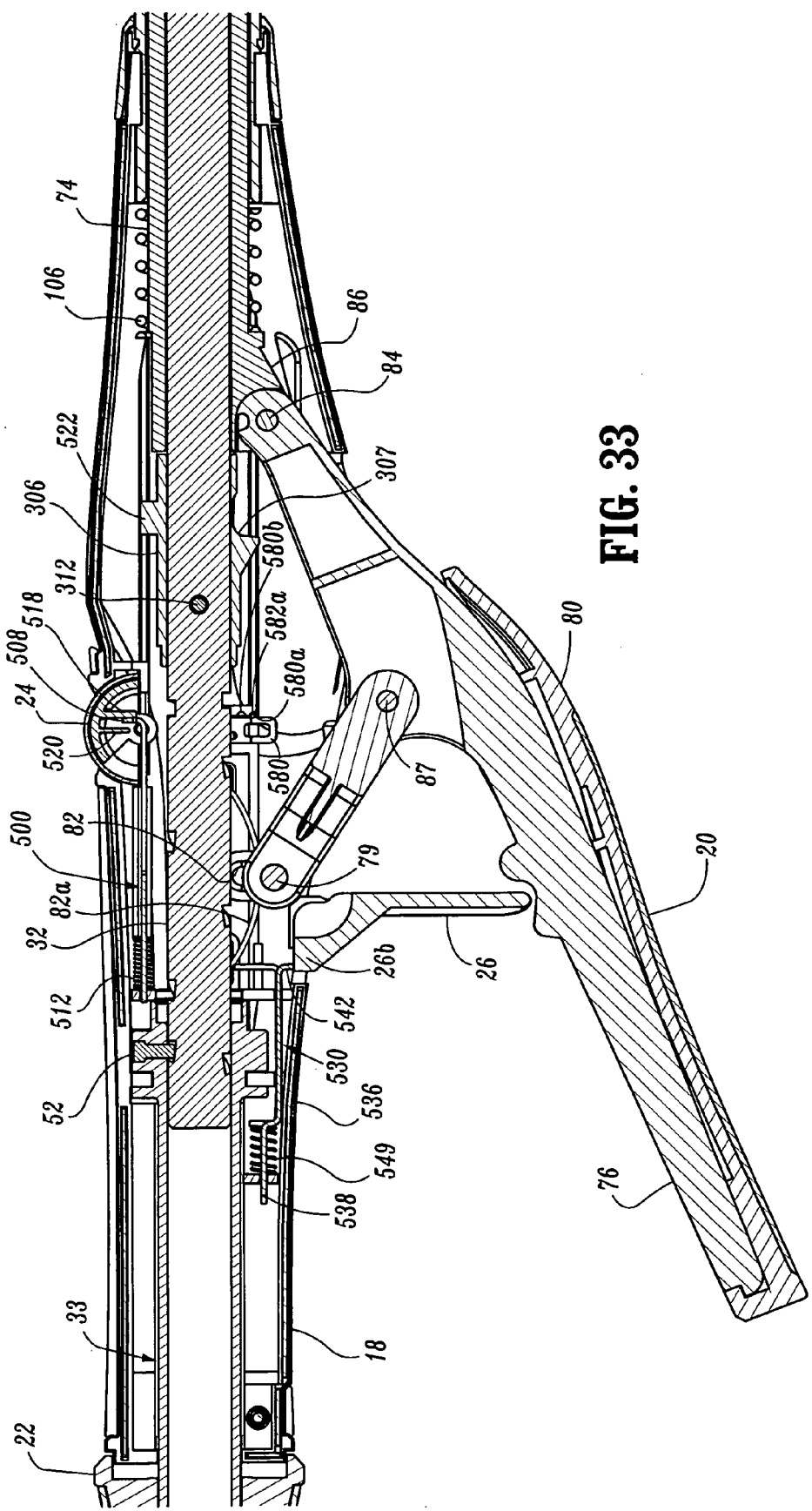
FIG. 33 is an enlarged view of the indicated area of detail shown in FIG. 31.
Figure 34:
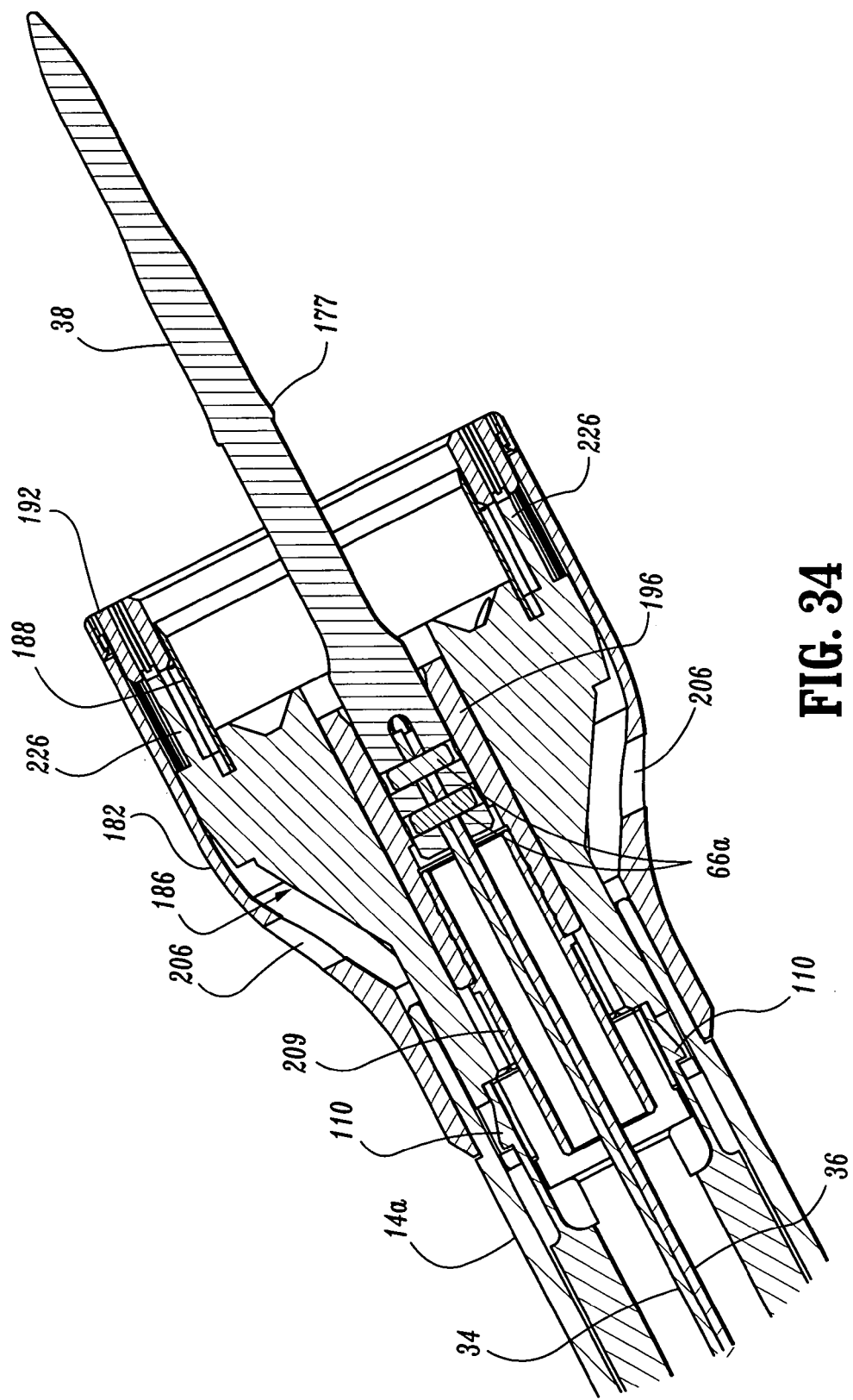
FIG. 34 is an enlarged view of the indicated area of detail shown in FIG. 31.
Figure 35:
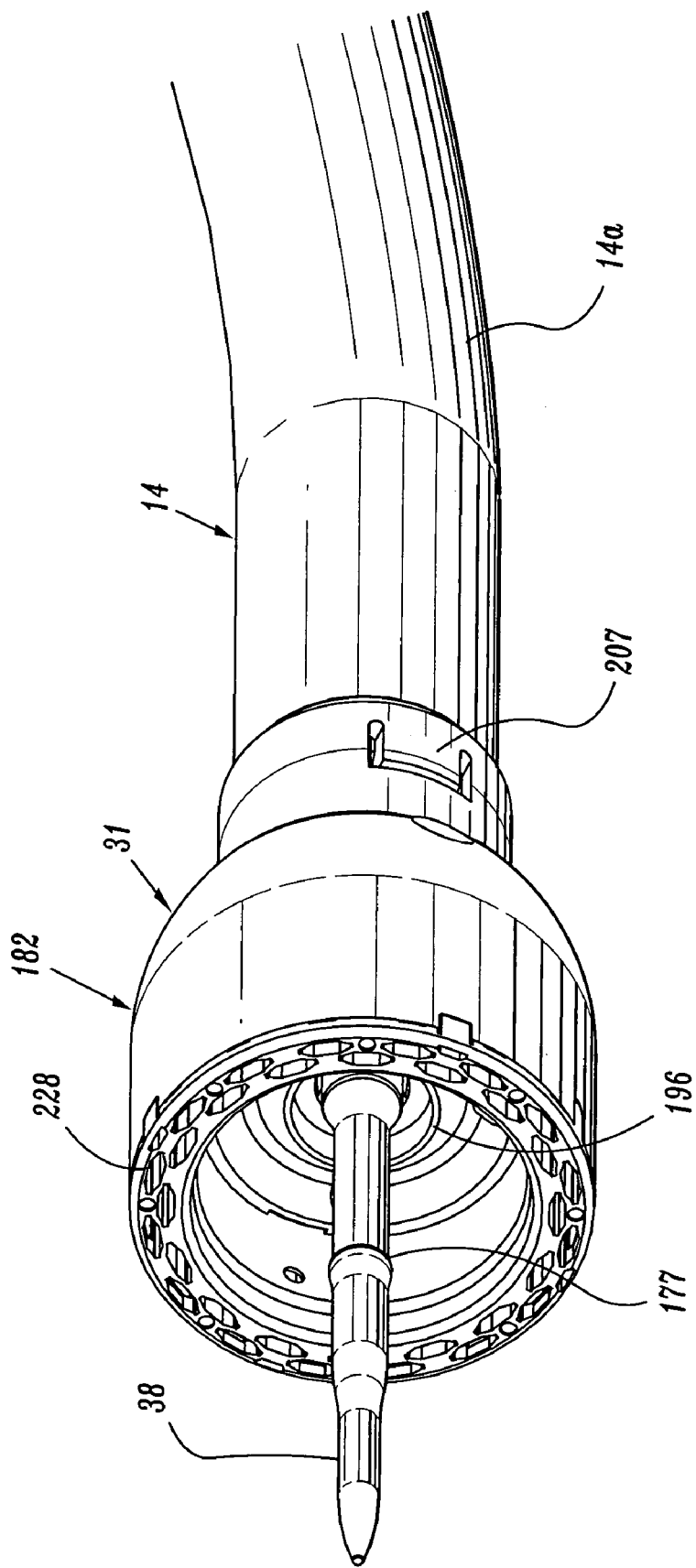
FIG. 35 is a perspective view from the front of the distal end of the surgical stapling device shown in FIG. 31 with the anvil assembly removed.

When firing trigger 20 is actuated, i.e., pivoted about pivot member 84, firing link 72 is moved proximally until pivot member 79 engages an abutment surface 307 (FIGS. 25, 28 and 48) formed on screw stop 306. Screw stop 306 is axially fixed to screw 32. When firing trigger 20 is pushed distally, pusher link 74 is advanced distally against the bias of spring 106. Turning again to FIG. 6, since the distal end of pusher link 74 is connected to pusher back 186, actuation of firing trigger 20 effects advancement of pusher back 186 within shell assembly 31 to eject staples from shell assembly 31 in a manner to be described below.

Anvil Assembly

Referring to FIGS. 10–21, anvil assembly 30 includes an anvil head assembly 120 and an anvil center rod assembly 152. Anvil head assembly 120 includes a post 122, an anvil head 124, a backup plate 126, a cutting ring 128, an anvil 129 and a retaining clip 127. Post 122 is centrally positioned through a bore in anvil head 124. Anvil 129 is supported on anvil head 124 in an outer annular recess 136 and includes a plurality of pockets 140 for receiving and deforming staples. At least one tab 129*a* extends radially outwardly from anvil 129 and is dimensioned to be received within a cutout 124*a* formed in anvil head 124. Tab 129*a* and cutout 124*a* function to align anvil 129 within annular recess 136. Backup plate 126 includes a central opening 126*b* which is positioned about post 122 within an inner recess 134 of anvil head 124 between post 122 and annular recess 136. Backup ring 126 includes a raised platform 126*a*. Cutting ring 128 includes an opening 128*a* having a configuration substantially the same as platform 126*a*. Opening 128*a* is positioned about platform 126a to rotatably fix cutting ring 128a on backup ring 126. In one embodiment, cutting ring 128 is formed from polyethylene and is fixedly secured to backup plate 126 using, for example, an adhesive. Backup ring 126 may be formed from a harder material such as a metal. Alternately other materials of construction may be used to construct plate 126 and ring 128. Cutting ring 128 and backup plate 126 are slidably mounted about post 122. Backup plate 126 includes a pair of inwardly extending tabs 150 which will be described in further detail below. Cutting ring 128 includes tabs 128b which are received within cutouts 124b formed in anvil head 124 to properly align backup ring 126 and cutting ring 128 within anvil head 124.

Anvil center rod assembly 152 includes anvil center rod 154, a plunger 156 and plunger spring 158. A first end of center rod 154 includes a transverse throughbore 160 which is offset from the central longitudinal axis of center rod 154. Post 122 of anvil head assembly 120 also includes a transverse throughbore 162. A pivot member 164 pivotably secures post 122 to center rod 154 such that anvil head assembly 120 is pivotably mounted to anvil center rod assembly 152. Plunger 156 is slidably positioned in a bore 154b (FIG. 16) formed in the first end of center rod 154. Plunger 156 includes an engagement finger 168 which is offset from the pivot axis of anvil head assembly 120 and biased into engagement with the base 122a of post 122 by plunger spring 158 to urge anvil head assembly 120 to a pivoted position orthogonal to center rod 154. In a prefired position, tabs 150 formed on backup plate 126 engage a top surface 154a (FIG. 20) of center rod 154 to prevent anvil head assembly 120 from pivoting about pivot member 164. As device 10 is fired, backup plate 126 and cutting ring 128 are moved deeper into anvil recess 134 of anvil head 124 about post 122 (FIG. 21) by knife 188 (FIG. 6) in a manner to be described in further detail below. Movement of backup plate 126 and cutting ring 128 into anvil recess 134 moves tabs 150 out of engagement with top surface 154a of center rod 154 to permit plunger 156 to pivot anvil head assembly 120 about pivot member 164.

A retainer clip 127 is positioned in a transverse slot 122c formed in post 122 and includes a pair of outwardly biased flexible arms 127a and 127b. Arm 127b includes a recess 127c dimensioned to receive pivot pin 164 (FIG. 17). Prior to firing device 10, arms 127a and 127b are deformed inwardly by backup plate 126 (FIG. 17). After device 10 has been fired and backup plate 126 has been pushed deeper into anvil head 124 by knife 188, flexible arms 127a and 127b spring outwardly to a position in front of backup plate 126. In this position, arms 127a and 127b prevent cutting ring 128 and backup plate 126 from sticking to knife 188 when anvil assembly 30 is unapproximated.

A second end of center rod 154 includes a bore 170 defined by a plurality of flexible arms 155. Bore 170 is dimensioned to receive a removable trocar 157 (FIG. 12). Flexible arms 155 each include an opening 155a dimensioned to receive a projection 157d formed on removable trocar 157 to releasably secure trocar 157 to center rod 154 (FIG. 13). The distal ends of each of flexible arms 155 include an internal shoulder 155b dimensioned to releasably engage anvil retainer 38 (FIG. 6) in a manner to be discussed in detail below. A plurality of splines 181 (FIG. 10) are formed about center rod 154 and are dimensioned to be received within grooves 196a (FIG. 6) in shell assembly 31 to align anvil assembly 30 with shell assembly 31 during approximation of the anvil and shell assemblies. Center rod 154 also includes an annular recessed portion 183 to facilitate grasping of anvil assembly 30 by a surgeon with a grasper.

Turning again to FIG. 12–15, Removable trocar 157 includes a trocar tip 157a, a body portion 157b and a cantilevered arm 157c. Projection 157d is positioned on the end of cantilevered arm 157c. Arm 157c is deflectable downwardly, i.e., radially inwardly, in the direction indicated by arrow "A" in FIG. 13 to facilitate insertion of body portion 157b into bore 170 of center rod 154. Splines 157e are provided on body portion 157b to properly align trocar 157 within bore 170 of center rod 154. Arm 157c biases projection 157d outwardly such that when projection 157d passes beneath opening 155a in center rod 154, projection 157d snaps into opening 155a to releasably secure removable trocar 157 to center rod 154. A tab 157f is positioned on arm 157c and can be depressed to facilitate removal of trocar 157 from center rod 154. Trocar tip 157a includes a throughbore 157g dimensioned to receive a suture (not shown) to facilitate locating and removal of trocar 157 within and from the human body. Although illustrated as having a sharpened tip, other trocar tip configurations are envisioned, e.g., blunt.

Shell Assembly

Referring to FIG. 6, shell assembly 31 includes a shell 182, a pusher back 186, a cylindrical knife 188, and a staple guide 192. Shell 182 includes an outer housing portion 194 and an inner guide portion 196 having grooves 196a for mating with splines 181 on anvil center rod 154 (FIG. 10). Outer housing portion 194 defines a throughbore 198 having a distal cylindrical section 200, a central conical section 202 and a proximal smaller diameter cylindrical section 204. A plurality of openings 206 may be formed in conical section 202. Openings 206 are dimensioned to permit fluid and tissue passage during operation of the device. A pair of diametrically opposed flexible engagement members 207 are formed on proximal cylindrical section 204 of shell 182. Engagement members 207 are positioned to be received in openings 207a formed on the distal end of outer tube 14a to secure shell 182 to elongated body 14. A pair of openings 211 formed in the proximal end of outer tube 14a are dimensioned to receive protrusions (not shown) formed on the internal wall of stationary handle 18 (FIG. 1) to facilitate attachment of tube 14a to handle portion 12.

Turning again to FIG. 6 Pusher back 186 includes a central throughbore 208 which is slidably positioned about inner guide portion 196 of shell 182. Pusher back 186 includes a distal cylindrical section 210 which is slidably positioned within distal cylindrical section 200 of shell 182, a central conical section 212 and a proximal smaller diameter cylindrical section 214. The proximal end of pusher back 186 includes members 220 which are configured to lockingly engage with resilient fingers 110 of pusher link 74 to fasten pusher link 74 to pusher back 186 such that a distal face of pusher link 74 abuts a proximal face of pusher back 186.

The distal end of pusher back 186 includes a pusher 190. Pusher 190 includes a multiplicity of distally extending fingers 226 dimensioned to be slidably received within slots 228 formed in staple guide 192 to eject staples 230 therefrom. Cylindrical knife 188 is frictionally retained within the central throughbore of pusher back 186 to fixedly secure knife 188 in relation to pusher 190. Alternately, knife 188 may be retained within pusher back 186 using adhesives, crimping, pins, etc. The distal end of knife 188 includes a circular cutting edge 234.

In operation, when pusher link 74 is advanced distally in response to actuation of firing trigger 20, as will be described below, pusher back 186 is advanced distally within shell 182. Advancement of pusher back 186 advances fingers 226 through slots 228 of staple guide 192 to advance staples 230 positioned within slots 228 and eject staples 230 from staple guide 192 into staple deforming pockets 140 of anvil 129 (FIG. 11). Since knife 188 is secured to pusher back 186, knife 188 is also advanced distally to core tissue as will be described in more detail below.

A rigid bushing 209 is supported in the proximal end of inner guide portion 196 of shell 182. Bushing 209 defines a throughbore dimensioned to slidably receive anvil retainer 38 and center rod 154 (FIG. 10) of anvil assembly 30. Bushing 209 provides lateral support for flexible arms 155 of center rod 154 when the anvil assembly 30 has been approximated to prevent disengagement of anvil assembly 30 from anvil retainer 38. In the unapproximated position, flexible arms 155 of center rod 154 are positioned externally of bushing 209 to permit removal of anvil assembly 30 from retainer 38.

Cam Adjustment Mechanism

Referring to FIGS. 8 and 22–28, a cam adjustment member 400 is secured by set screw 312 onto a sidewall 306a of screw stop 306 within a recess 306b formed in sidewall 306a. Cam adjustment member 400 includes a circular disc 402 having a throughbore 404. Throughbore 404 is eccentrically formed through disc 402 and is dimensioned to receive set screw 312. A smaller notch or hole 406 is also formed in disc 402 and is dimensioned to receive the tip of an adjustment tool (not shown). Recess 306b (FIG. 22) includes a forward abutment shoulder or surface 306c (FIG. 23) and a rear abutment surface 306d and is dimensioned to receive disc 402 such that the outer edge of disc 402 abuts forward and rear abutment surfaces 306c and 306d.

Set screw 312 extends through disc 402 and screw stop 306 and is received in a threaded bore 32a in screw 32 to secure screw stop 306 in position on screw 32. Cam adjustment member 400 functions to adjust the axial position of screw stop 306 on screw 32. More specifically, set screw 312 can be loosened to allow disc 402 to rotate within recess 306b of screw stop 306 while still remaining fixed to screw 32. Since disc 402 is eccentrically mounted about screw 32 and engages forward and rear abutment surfaces 306c and 306d of recess 306b, rotation of disc 402 about fixed set screw 312 will urge screw stop 306 axially along screw 32 to adjust the axial position of screw stop 306 on screw 32. For example, when disc 402 is rotated in a clockwise direction (as viewed in FIG. 28) identified by arrow "B", screw stop 306 will be moved axially in relation to screw 32 in the direction indicated by arrow "C" in response to engagement between the outer edge of disc 402 and rear shoulder 306d of recess 306b. Conversely, when disc 402 is rotated in a counter-clockwise direction (as viewed in FIG. 27), identified by arrow "D", screw stop 306 will be moved axially in relation to screw 32 in the direction indicated by arrow "E" in response to engagement between the outer edge of disc 402 and forward shoulder 306c of recess 306b.

When stapling device 10 is in a fully approximated position (as can be seen for instance in FIG. 65), i.e., anvil assembly 30, 640 and shell assembly 31, 605 are brought into juxtaposed alignment to define a tissue receiving clearance, screw stop 306 (FIG. 47) abuts against body portion 42 of the rotatable sleeve 33, i.e., sleeve 33 functions as a stop for the approximation mechanism. In this position, anvil assembly 30 and shell assembly 31 are spaced slightly to define a tissue receiving clearance. By providing cam adjustment member 400, the tissue receiving clearance can be selectively adjusted to be within a desired range by adjusting the position of screw stop 306 on screw 32. In one embodiment, cam adjustment member 400 permits adjustment of the tissue receiving clearance of ±0.045 inches, although greater or lesser adjustment capabilities are also envisioned. Typically, adjustments to the tissue receiving clearance will be made by the device manufacturer. Alternately, a hole or opening (not shown) may be provided in handle portion 12 (FIG. 1) to provide direct access to adjustment member 400 to allow for adjustment of the tissue receiving clearance at the surgical site.

Indicator Mechanism

Referring to FIGS. 3–5, 9, 22, 29 and 33, the indicator mechanism includes indicator 24, lens cover 24a and slide member 500. Indicator 24 is pivotally supported about a pivot member 502 which may be formed monolithically with handle sections 18a and 18b. Lens cover 24a is positioned above indicator 24 and may be formed of magnification material to facilitate easy visualization of indicator 24. Slide member 500 (FIG. 29) includes a body portion 504 having a elongated slot 506 formed therein, a distal abutment member or upturned lip portion 508, and a proximal extension 510. Slide member 500 is slidably positioned between handle sections 18a and 18b. Proximal extension 510 is slidably supported within stationary handle 18 by support structure 516 (FIG. 5). A biasing member 512, e.g., a coil spring, is positioned in compression about proximal extension 510 between support structure 516 and body portion 504 of slide member 500 to urge slide member 500 distally within stationary handle 18. Indicator 24 includes a pair of downwardly extending projections 518 and 520 positioned about pivot member 502. Upturned lip portion 508 of slide member 500 is positioned between projections 518 and 520 and is positioned to engage projections 518 and 520 as it moves within stationary handle 18. In the unfired position of device 10, biasing member 512 urges slide member 500 distally to move lip portion 508 into engagement with projection 518 to pivot indicator to a first position, which provides indication to a surgeon that the device has not been approximated and is not in a fire-ready condition.

As discussed above, screw stop 306 is fixedly attached to screw 32. Screw stop 306 includes a first engagement member 522 which is positioned to travel through slot 506 and engage the proximal end 506a of slot 506 during approximation of the device. When engagement member 522 abuts proximal end 506a (FIG. 29) of slot 506, further approximation of device 10 moves slide plate 500 proximally within stationary handle 18 against the bias of spring 512 such that upturned lip 508 of slide member 500 engages projections 518 & 520 of indicator 24. (See FIG. 48). Engagement between projections 518 & 520 and lip 508 causes indicator 24 to pivot about pivot member 502 to a second position. In the second position, indicator 24 provides indication to a surgeon that the device has been approximated and is now in a fire-ready position.

Fire-Lockout Mechanism

Referring to FIGS. 3–5, 22, 30, 33, and 47, the firing-lockout mechanism includes trigger lock 26 and lockout member 530. Trigger lock 26 is pivotally supported within bores 532 in handle sections 18a and 18b about pivot member 534. In one embodiment, pivot member 534 extends from an upper edge of trigger lock 26 and is T-shaped and frictionally engages the inner wall of bores 532 to prevent free rotation of trigger lock 26. Tip 26a (FIG. 5) of trigger lock 26 is positioned between abutments 89 and 91 on body portion 76 of firing trigger 20 to prevent actuation of trigger 20 when trigger lock 26 is in the locked position. Trigger lock 26 also includes a proximal extension 26b (FIG. 4) which will be discussed in further detail below.

Lockout member 530 (FIG. 30) includes a body portion 536, a proximal extension 538, a pair of front legs 540a, a pair of rear legs 540b, and an abutment member or downturned lip portion 542. Lockout member 530 is slidably positioned between first and second stops 544 and 546 (FIG. 5) formed on an internal wall of handle sections 18a and 18b. Stop 544 is positioned to engage rear legs 540b and stop 546 is positioned to engage front legs 540a. It is also envisioned that a single abutment member may be substituted for each pair of legs. A biasing member 548, e.g., a coil spring, is positioned between stop 544 and body 536 about proximal extension 538 to urge lockout 530 to its distal-most position with legs 540a abutting stop 546. In this position, extension 26b of trigger lock 26 is positioned beneath lip portion 542 of lockout member 530 to prevent pivotal movement of trigger lock 26, and thus prevent actuation of stapling device 10.

As discussed above and as shown in FIG. 47, screw stop 306 is secured to screw 32. A second engagement member or members 548 extend downwardly from screw stop 306. (See FIG. 22). When stapling device 10 is approximated and screw 32 is moved proximally within stationary handle 18, engagement member 548 abuts front legs 540a of lockout member 530 to move lockout member 530 proximally against the bias of member 548 to a position in which lip portion 542 is spaced proximally of extension 26b of trigger lock 26. In this position of lockout member 530, trigger lock 526 can be pivoted to permit firing of stapling device 10.

Tactile Indicator Mechanism

Referring to FIGS. 3, 5, 9 and 9A, a tactile indicator mechanism provided in stationary handle 18 includes an abutment member 580 which is slidably positioned in a vertical slot 582 defined within handle sections 18a and 18b. Abutment member 580 includes a protuberance 580a and a guide rib 580b. Protuberance 580a is dimensioned to be received within one of two detents 582a and 582b formed along a wall of slot 582. Abutment member 580 is movable from a retracted (downward) position, wherein protuberance 580a is positioned within detent 582a, to an extended (upward) position, wherein protuberance 580a is positioned within detent 582b. Engagement between protuberance 580a and detents 582a and 582b retains abutment member 580 in the respective position. Detent 582c, formed in vertical slot 582, is sized to slidably receive guide rib 580b and thereby maintain member 580 in contact with slot 582.

Prior to firing of stapling device 10, abutment member 580 is located in the retracted (downward) position (FIG. 5). When device 10 is fired, an extension 590 of firing link 72 engages abutment member 580 and moves abutment member 580 from its retracted to its extended position. In the extended position, abutment member 580 extends into channel 111 of stationary handle 18.

Figure 57:
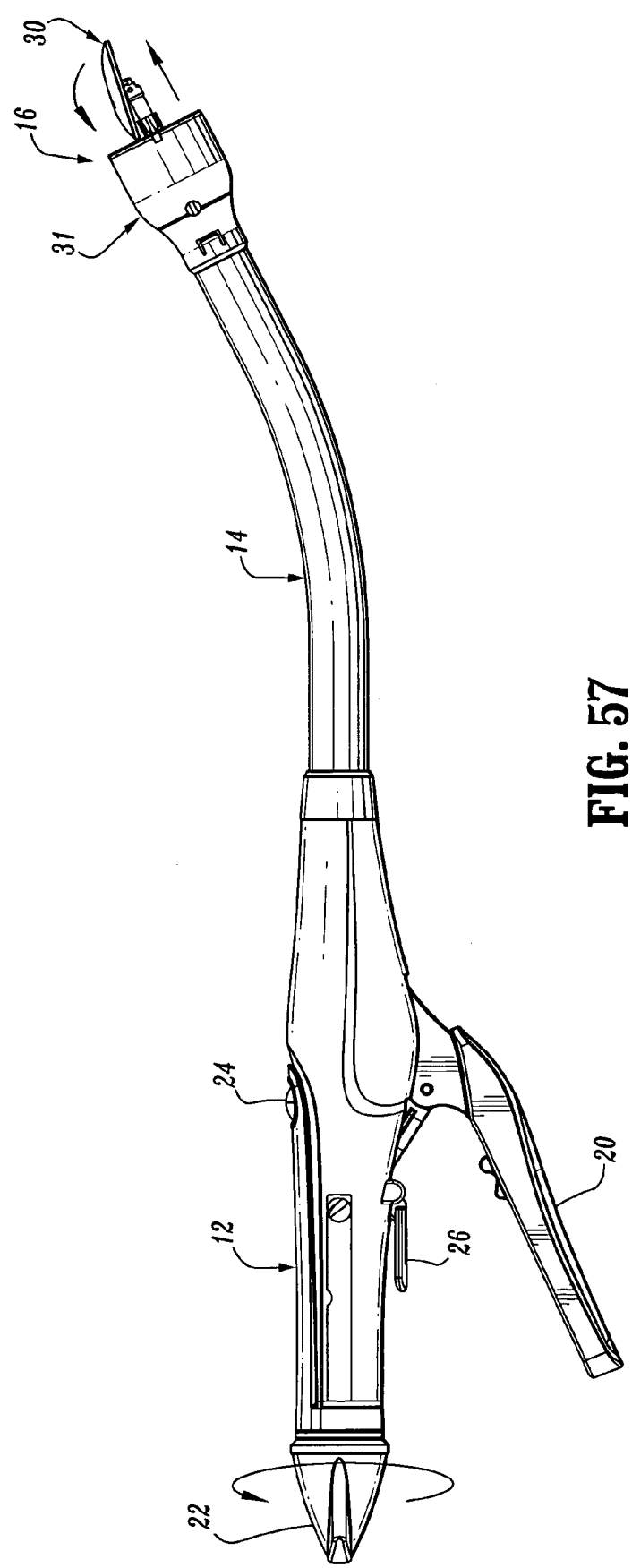
FIG. 57 is a side view of the surgical stapling device shown in FIG. 45 after the anvil assembly and cartridge assembly have been unapproximated a distance sufficient to permit the anvil head assembly to pivot on the anvil center rod.
Figure 59:
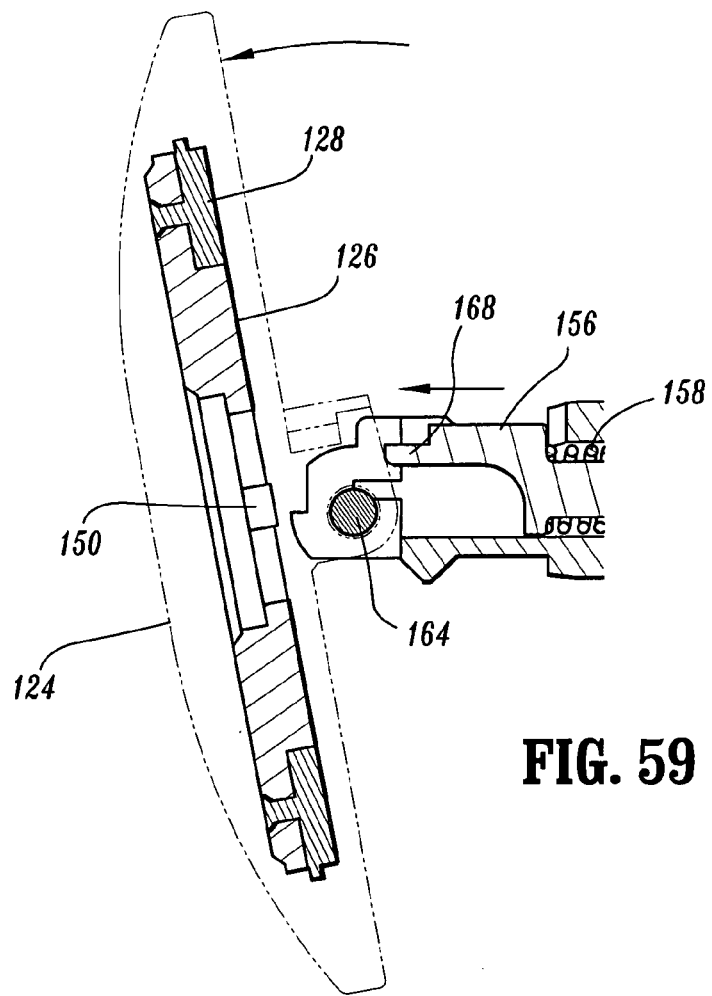
FIG. 59 is a side cross-sectional view of the anvil assembly shown in FIG. 56 as the anvil head assembly begins to tilt.
Figure 60:
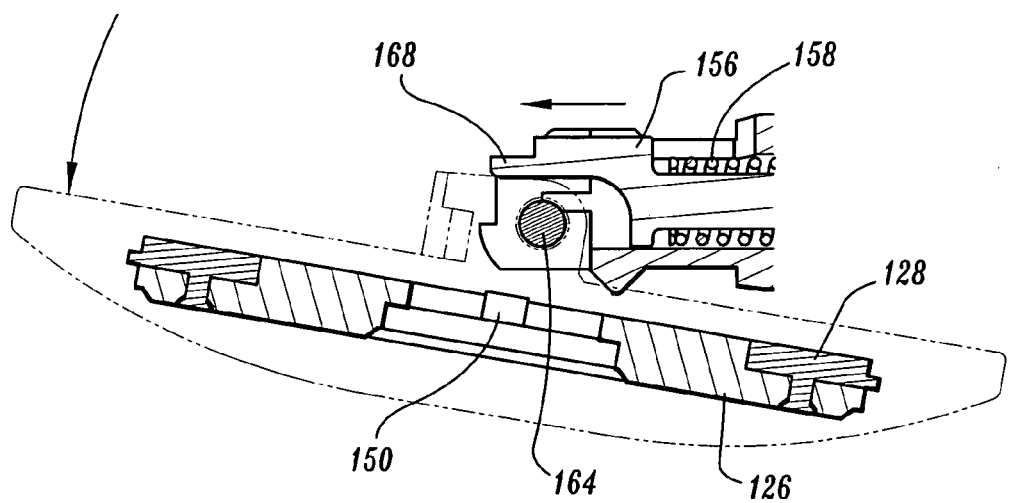
FIG. 60 is a side cross-sectional view of the anvil assembly shown in FIG. 59 with the anvil assembly tilted.
Figure 61:
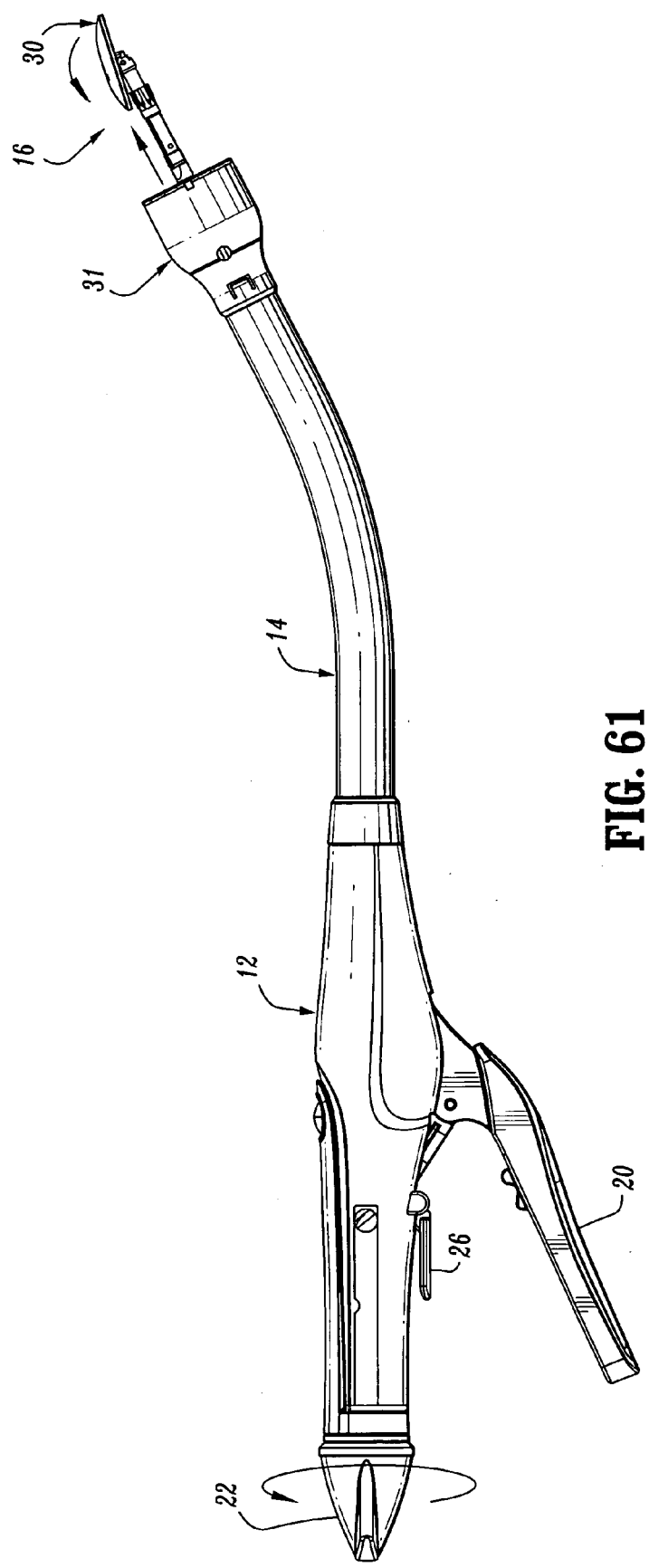
FIG. 61 is a side view of the surgical stapling device shown in FIG. 45 with the anvil head assembly unapproximated and tilted.

Screw stop 306 includes a pair of wings 584 which are slidably positioned in channel 111 of stationary handle 18. After stapling device 10 has been fired, abutment member 580 is positioned within channel 111. During unapproximation of anvil assembly 150 and cartridge assembly 31, one of the wings 584 of screw stop 306 engage abutment member 580 when the device has been unapproximated a sufficient distance to allow anvil assembly 30 to pivot to its reduced profile position (as will be discussed in mere detail below and as can be seen in FIG. 57). Engagement between abutment member 580 and wing 584 of screw stop 306 provides a tactile and/or an audible indication to the surgeon that the anvil assembly 120 has tilted and stapling device 10 can be removed from a patient. If the surgical stapling device is unapproximated further, wing 584 will force abutment member 580 from the extended position back to the retracted position.

Operation

Operation of surgical stapling device 10 will now be described in detail with reference to FIGS. 31–61.

FIGS. 31–35 illustrate surgical stapling device 10 in the unapproximated or open position prior to attachment of anvil assembly 30 to anvil retainer 38. In this position, biasing member 106 is engaged with coupling 86 to urge pusher link 74 to its proximal-most position in which coupling 86 abuts screw-stop 306. Biasing member 512 is engaged with slide member 500 of the indicator mechanism to position slide member 500 in engagement with projection 518 of indicator 24 to pivot indicator 24 in a clockwise direction, as viewed in FIG. 33. Biasing member 549 is engaged with body 536 of lockout member 530 to urge lockout member 530 to its distal-most position, wherein lip portion 542 of lockout member 530 is positioned above extension 26b of trigger lock 26 to prevent movement of trigger lock 26 to the unlocked position. Biasing member 82a engages pivot member 79 to urge pivot member 79 to the base of vertical slot 82. Tactile indicator 580 is in the retracted or downward position with protrusion 580a positioned with detent 582a.

Figure 38:
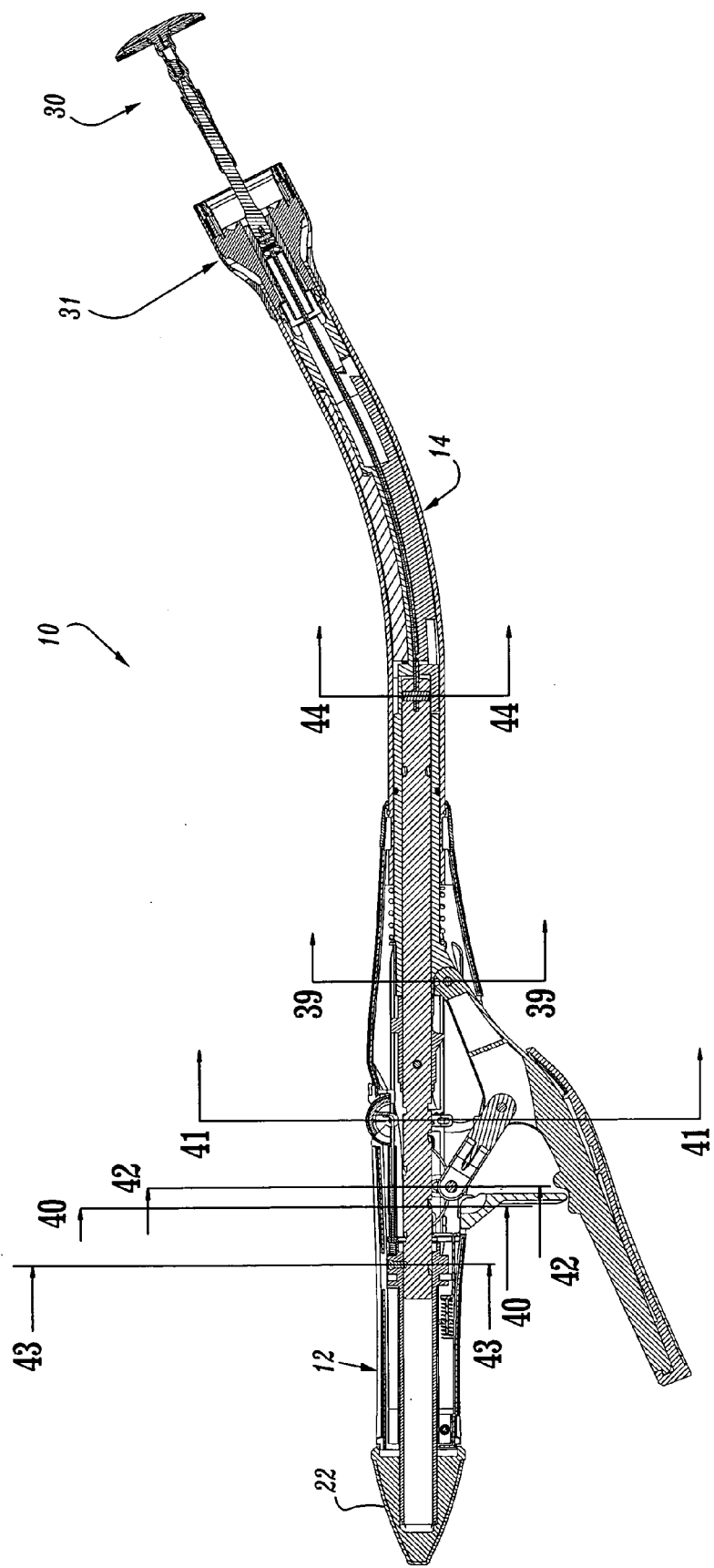
FIG. 38 is a side cross-sectional view of the surgical stapling device shown in FIG. 31 with the anvil assembly attached thereto.
Figure 45:
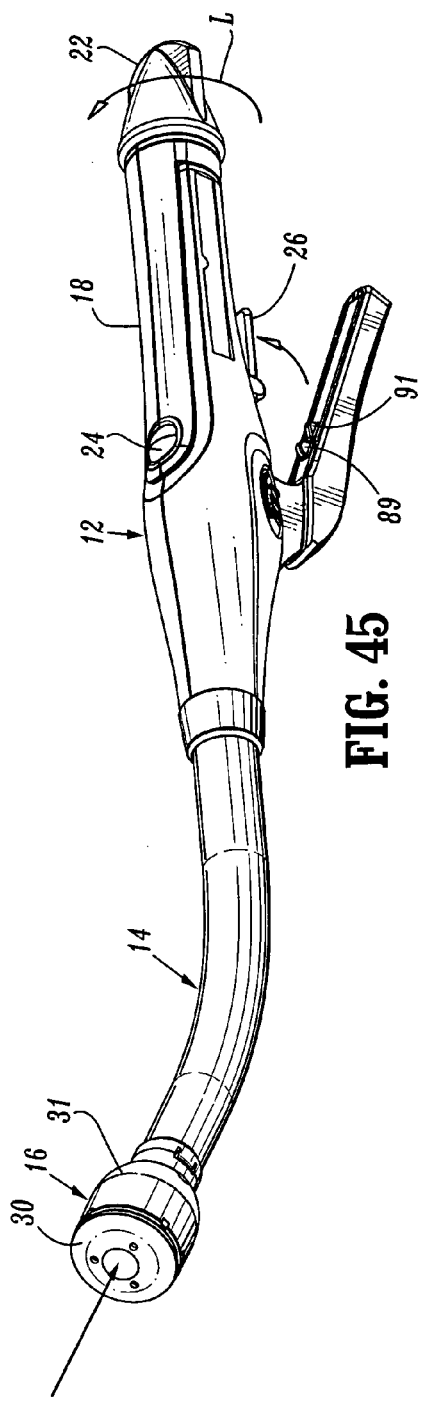
FIG. 45 is a side perspective view of the surgical stapling device shown in FIG. 38 with the anvil assembly in an approximated position.
Figure 46:
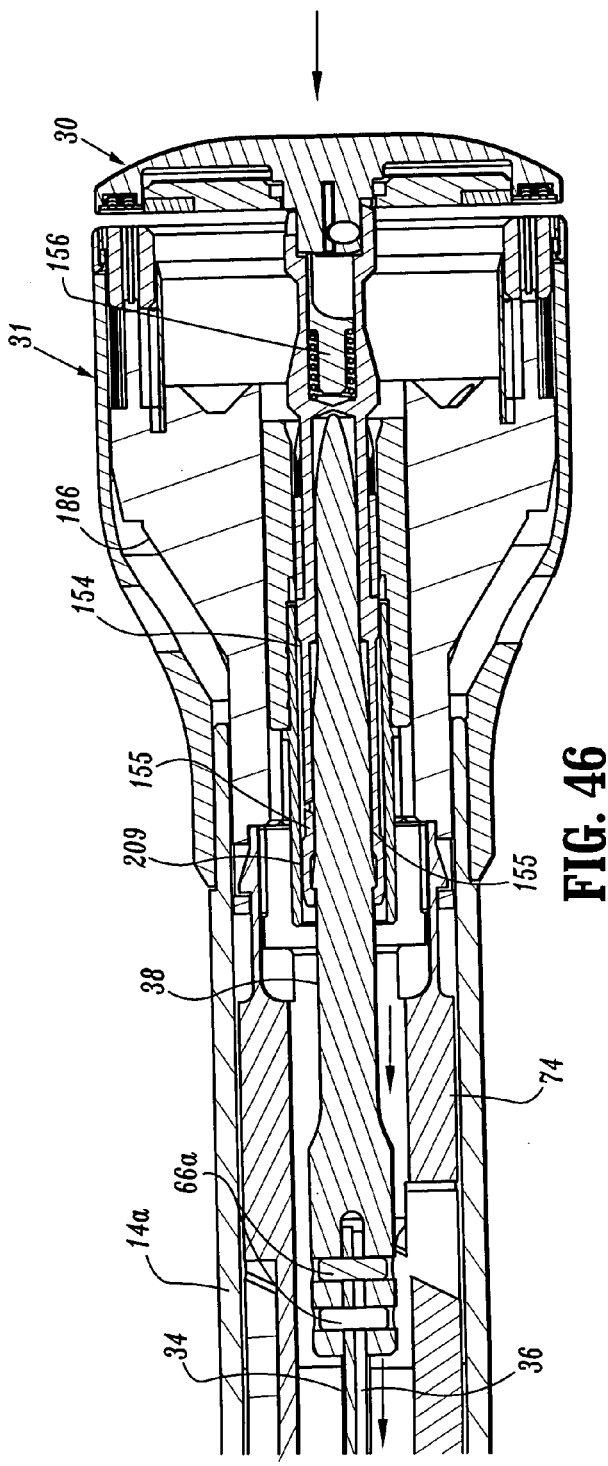
FIG. 46 is a side cross-sectional view of the distal end of the surgical stapling device shown in FIG. 45.

FIGS. 36–44 illustrate surgical stapling device 10 with anvil assembly 30 attached to anvil retainer 38 and the anvil assembly 30 in the unapproximated or open position. Referring to FIGS. 37 and 38, during attachment of anvil assembly 30 to anvil retainer 38, anvil retainer 38 is positioned within bore 170 of center rod 154 of anvil assembly 30. Flexible arms 155 deflect outwardly to accommodate center rod 154. Center rod 154 is advanced onto anvil retainer 38 in the direction indicated by arrow "K" in FIG. 37 until internal shoulder 155b of flexible arms 155 passes over annular protrusion 177 formed on anvil retainer 38. At this point, resilient legs 155 releasably engage the anvil retainer. The position of the remaining components of stapling device are unaffected by attachment of anvil assembly 30 to anvil retainer 38 and remain as described above and shown in FIGS. 31–35.

FIGS. 45–50 illustrate surgical stapling device 10 during movement of anvil assembly 30 and cartridge assembly 31 to the approximated or closed position. As discussed above, anvil assembly 30 is moved to the approximated or closed position by rotating rotation knob 22 in the direction indicated by arrow "L" in FIG. 45. Rotation of knob 22 causes cylindrical sleeve 33 to rotate to move pin 52 along helical channel 50 of screw 32. Movement of pin 52 (FIG. 48) along helical channel 50 causes screw 32 to translate within sleeve 33. The distal end of screw 32 is connected to screw extensions 34 and 36 which are fastened at their distal ends to anvil retainer 38. As such, retraction of screw 32 within sleeve 33 is translated into proximal movement of anvil retainer 38 and anvil assembly 30. It is noted that when anvil assembly 30 is approximated, flexible legs 155 of center rod 154 are drawn into bushing 209 to lock legs 155 onto anvil retainer 38. (See FIG. 46).

As discussed above, screw stop 306 (FIG. 47) is axially fixed to screw 32 by set screw 312. Thus, as screw 32 is retracted within sleeve 33, screw stop 306 is moved from a distal position within stationary handle 18 to a proximal position. As screw stop 306 moves from the distal position to the proximal position, first engagement member 522 formed on screw stop 306 abuts proximal end 506a of slot 506 of slide plate 500 and moves slide plate 500 proximally against the bias of spring 512. As slide plate 500 moves proximally, lip 508 of slide member 500 engages projections 518 & 520 of indicator 24 to pivot indicator 24 in a counter-clockwise direction as viewed in FIG. 48.

Figure 47:
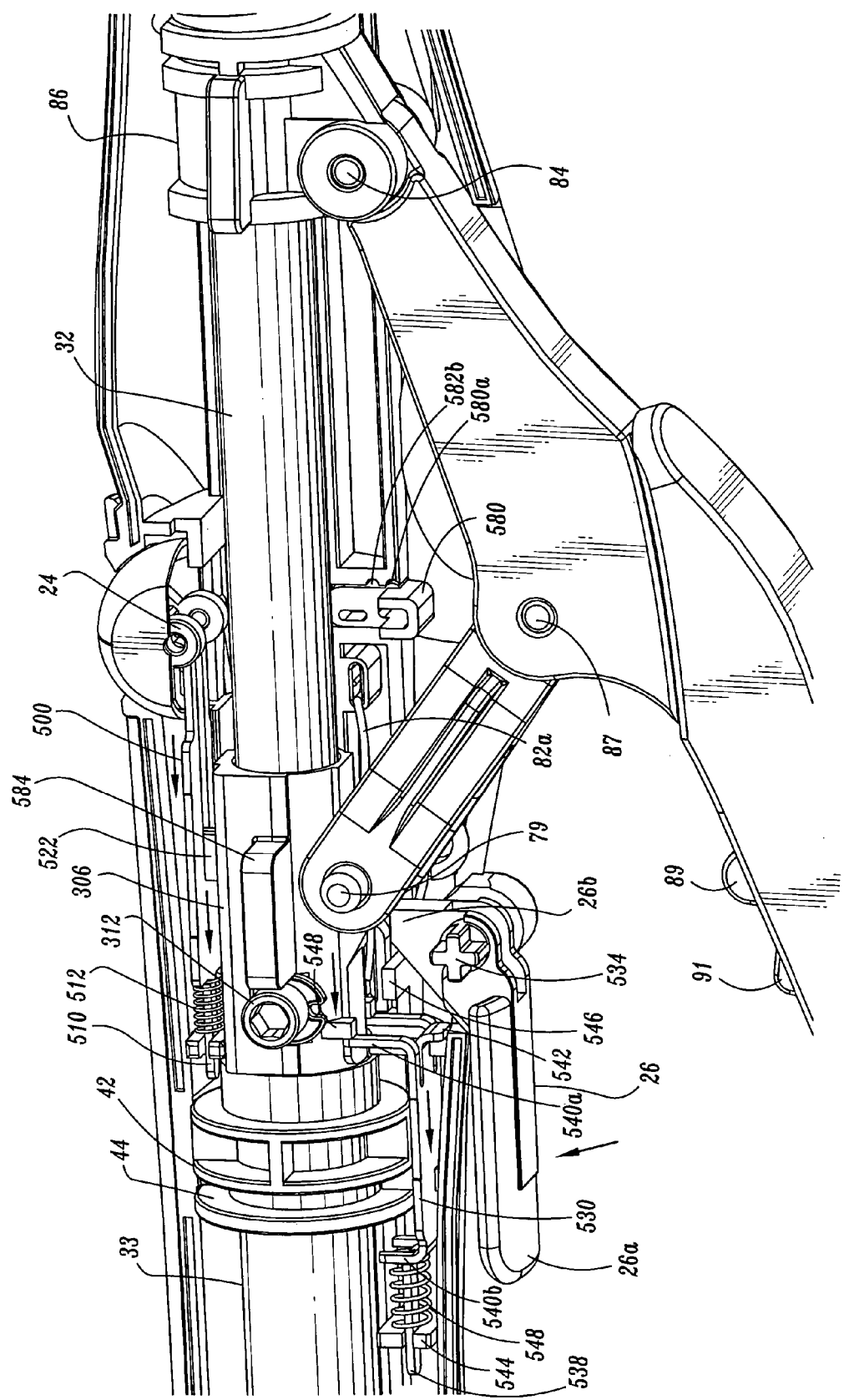
FIG. 47 is a side enlarged view of the handle assembly of the surgical stapling device shown in FIG. 45 with a handle section removed.
Figure 50:
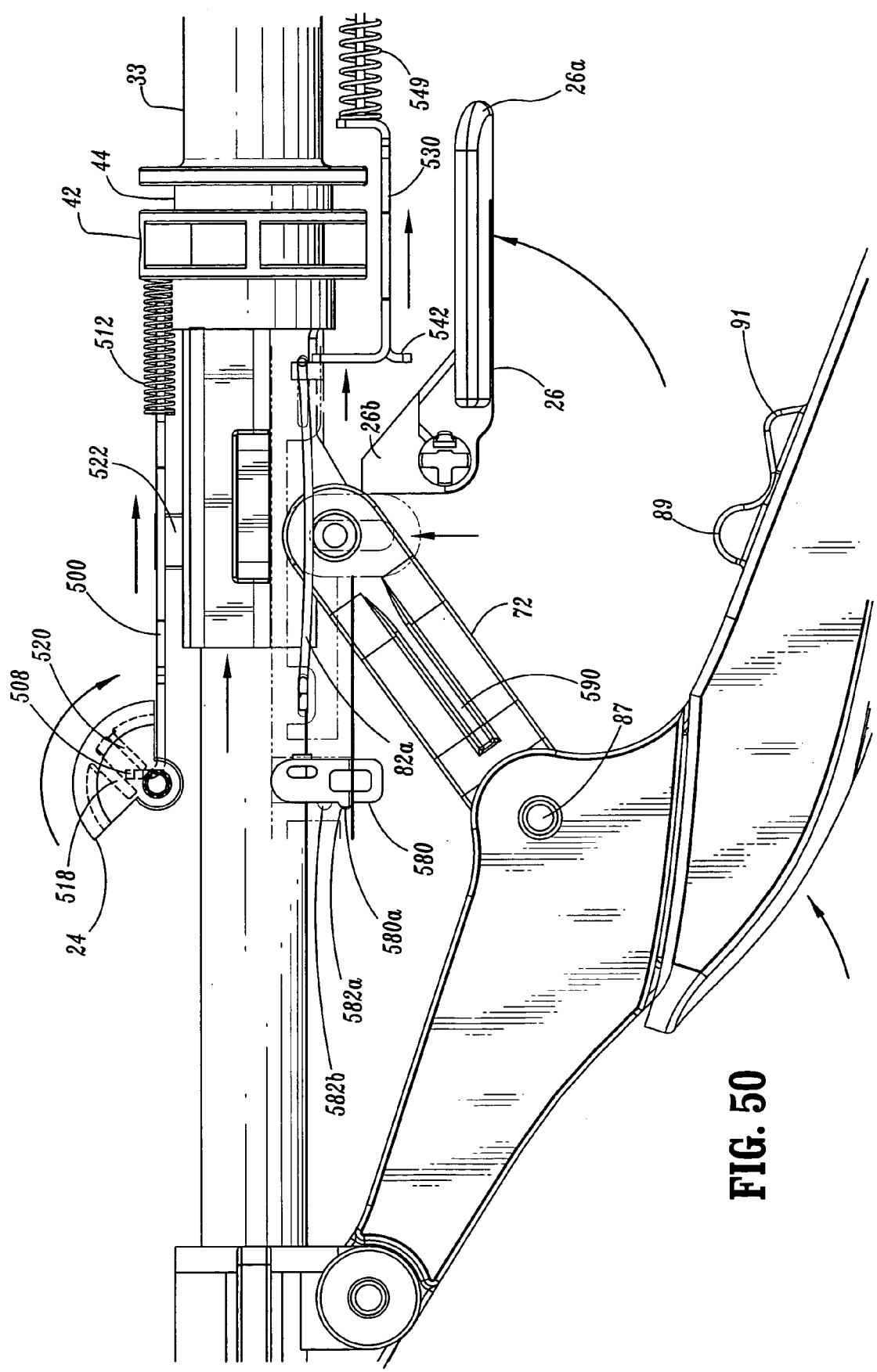
FIG. 50 is a side view of a portion of the handle assembly of the surgical stapler shown in FIG. 45 with the handle sections removed.
Figure 53:
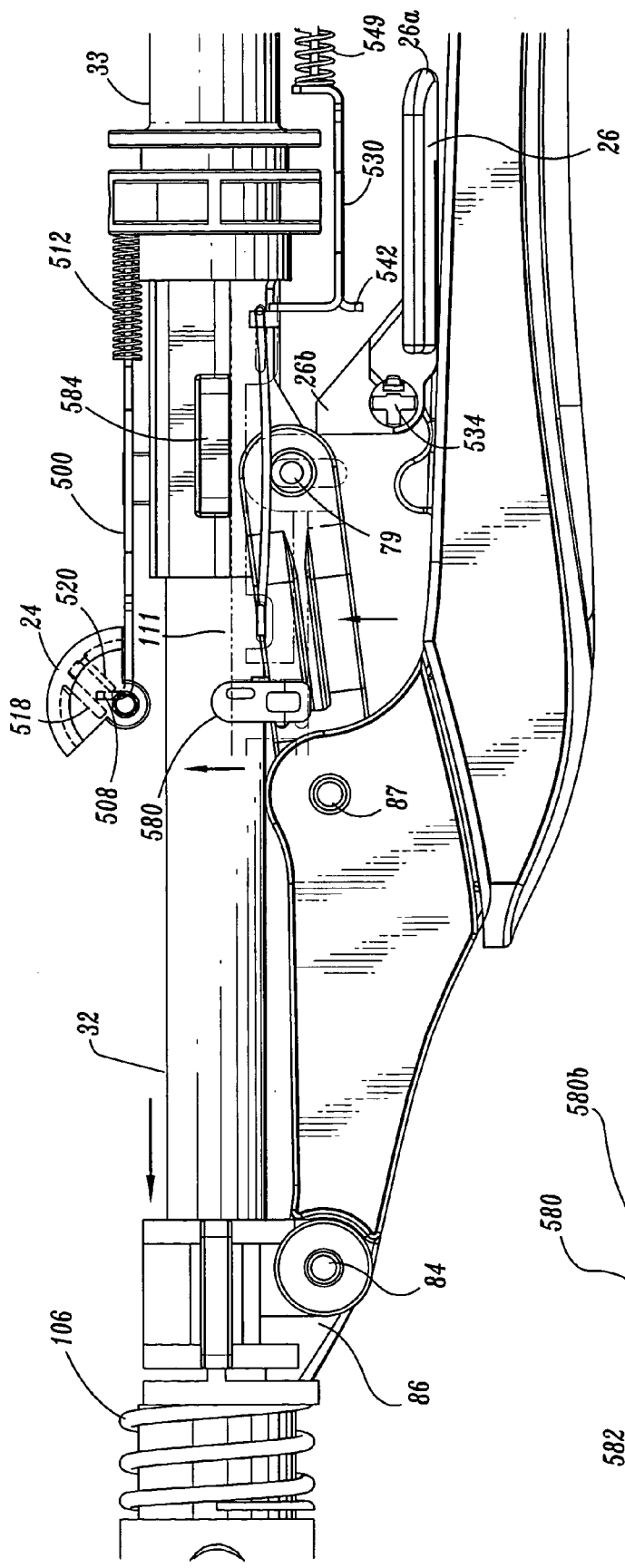
FIG. 53 is a side view of the handle assembly shown in FIG. 51 with the handle sections removed.
Figure 58:
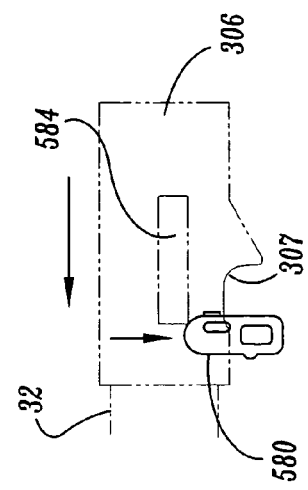
FIG. 58 is an enlarged view of the abutment member of the tactile indicator mechanism of the handle assembly shown in FIG. 53 (during unapproximation of the anvil and cartridge assemblies) with the wing of the screw stop, shown in phantom, in engagement with the abutment member.
Figure 54:
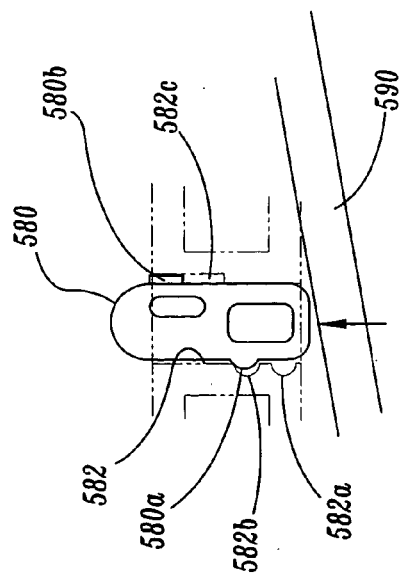
FIG. 54 is an enlarged view of the firing link extension engaging the abutment member of the tactile indicator mechanism of the handle assembly shown in FIG. 53.

Screw stop 306 also includes a second engagement member 548 (FIG. 47). As screw stop 306 is moved from the distal position to the proximal position during approximation of anvil assembly 30, second engagement member 548 engages distal legs 540a of lockout member 530 to move lockout member 530 proximally to a position in which lip portion 542 is spaced proximally of extension 26b of trigger lock 26. In this position, trigger lock 26 can be pivoted to an unlocked position to permit firing of stapling device 10.

Movement of screw stop 306 to its proximal-most position within stationary handle 18 positions abutment surface 307 (FIG. 48) of screw stop 306 in position to engage pivot member 79 of firing link 72. Abutment surface 307 comprises a substantially concave surface which is positioned to partially capture and act as a backstop for pivot 79 during firing of the stapling device.

FIGS. 51–56 illustrate surgical stapling device 10 during the firing stroke of firing trigger 20. As trigger 20 is compressed towards stationary handle 18 (as shown by the arrow in FIG. 51), pivot member 79 engages abutment surface 307 on screw stop 306 and firing trigger 20 is pushed distally. As discussed above, the distal end of firing trigger 22 is connected through coupling member 86 to the proximal end of pusher link 74. Accordingly, as firing trigger 20 is moved distally, pusher link 74 is moved distally to effect advancement of pusher back 186 within shell assembly 31. Fingers 190 of pusher back 186 engage and eject staples 230 from staple guide 192 (FIG. 52).

Figure 55:
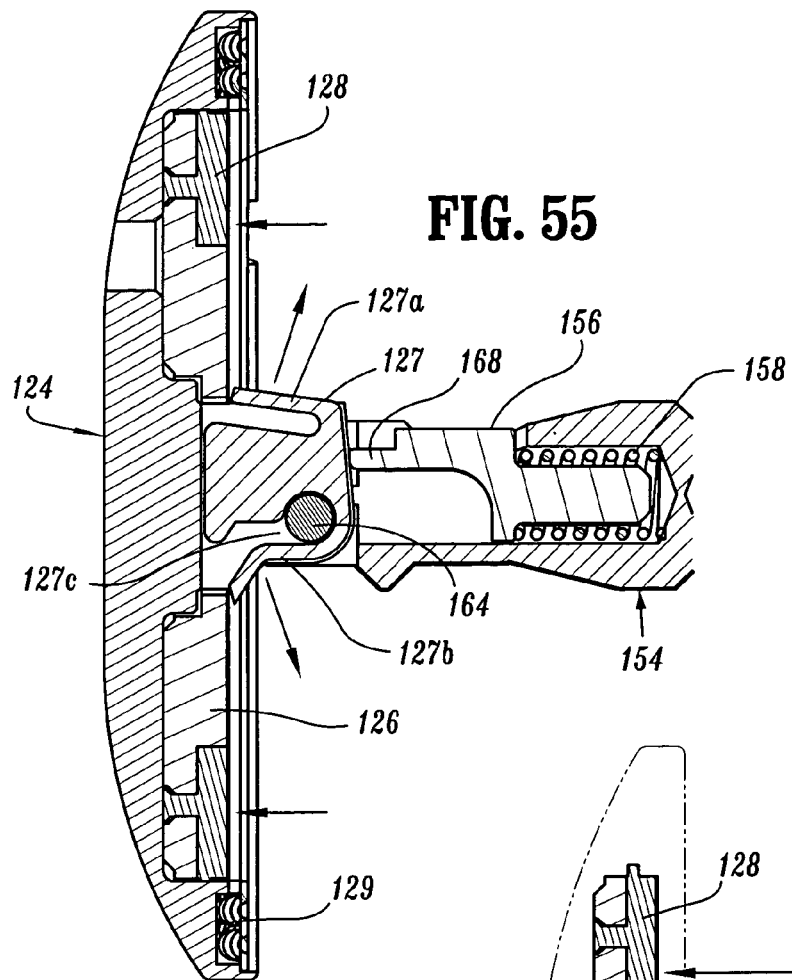
FIG. 55 is a side cross-sectional view of the distal portion of the anvil assembly of the surgical stapling device shown in FIG. 52.
Figure 56:
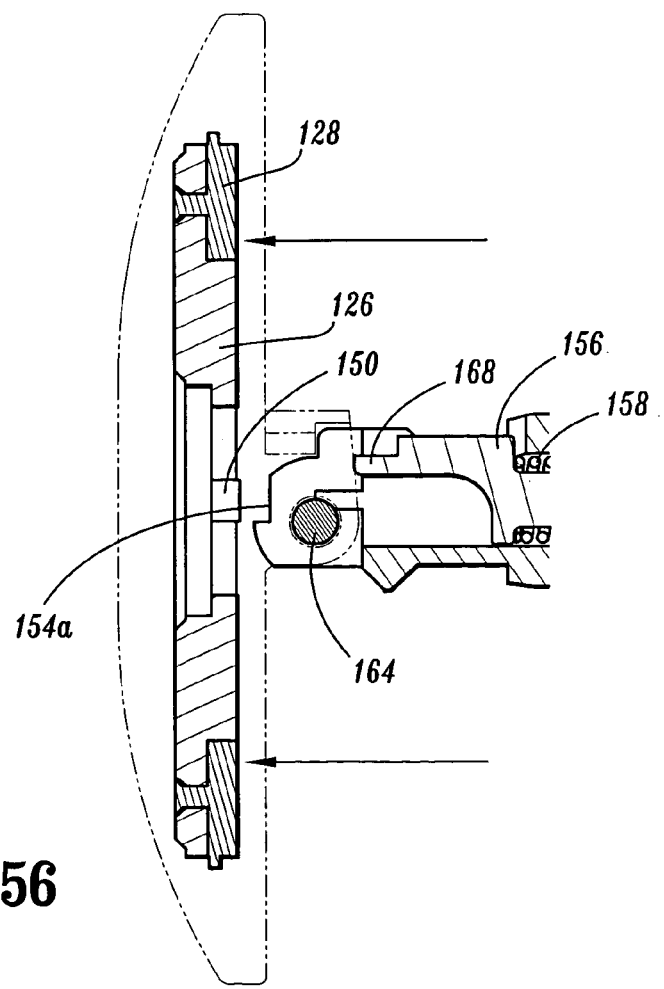
FIG. 56 is a side cross-sectional view of the distal portion of the anvil assembly shown in FIG. 55 with a portion of the anvil head assembly in phantom.

Cylindrical knife 188 is moved concurrently with pusher back 186 such that knife 188 moves into engagement with cutting ring 128 and backup plate 126. As discussed above, cutting ring 128 may be formed from polyethylene and backup plate 126 may be formed from a metal. When knife 188 engages cutting ring 128, it cuts into cutting ring 128 and pushes backup plate 126 deeper into anvil head 124 to move tabs 150 from engagement with top surface 154a of center rod 154 (FIG. 56). Anvil head 124 is now free to pivot about member 164 and is urged to do so by plunger 156. It is noted that because the anvil assembly is in juxtaposed alignment with shell assembly 31, the anvil head 14 will not pivot fully until the anvil and shell assemblies have been unapproximated a distance sufficient to allow the anvil head to fully pivot. When backup plate 126 moves into anvil head 124, flexible arms 127a and 127b of retainer clip 127 spring outwardly to a position in front of backup plate 126 blocking movement of backup plate 126 out of anvil head 124 (FIG. 55). As discussed above, arms 127a and 127b prevent backup plate 126 from sticking to knife 188 when anvil assembly 30 is returned to the unapproximated position.

Referring to FIGS. 57–60, during unapproximation of stapling device 10 after device 10 has been fired, wing 584 of screw stop 306 engages tactile indicator 580 (FIG. 58) at the point of unapproximation at which anvil assembly 124 is able to pivot to its tilted reduced profile position. Contact between wing 584 and tactile indicator 580 provides a tactile and/or audible indication that anvil head 124 has tilted. If additional force is provided to approximation knob 22, wing 584 of screw stop 306 will force tactile indicator to the retracted position to allow stapling device 10 to move to the fully open position. In this position, flexible arms 155 are positioned distally of bushing 209 and anvil assembly 30 can be disengaged from anvil retainer 28.

FIGS. 62–91 illustrate another embodiment of the presently disclosed surgical stapling device shown generally as 600. Stapling device 600 is configured and dimensioned to be particularly suitable for use in surgical procedures for removing internal hemorrhoids from a patient. Briefly, surgical stapling device 600 includes a proximal handle assembly 601, a central body portion 603 and a distal head portion 605. The handle assembly 601 is substantially identical to handle assembly 12 of surgical stapling device 10 and will not be discussed in further detail herein.

Figure 65:
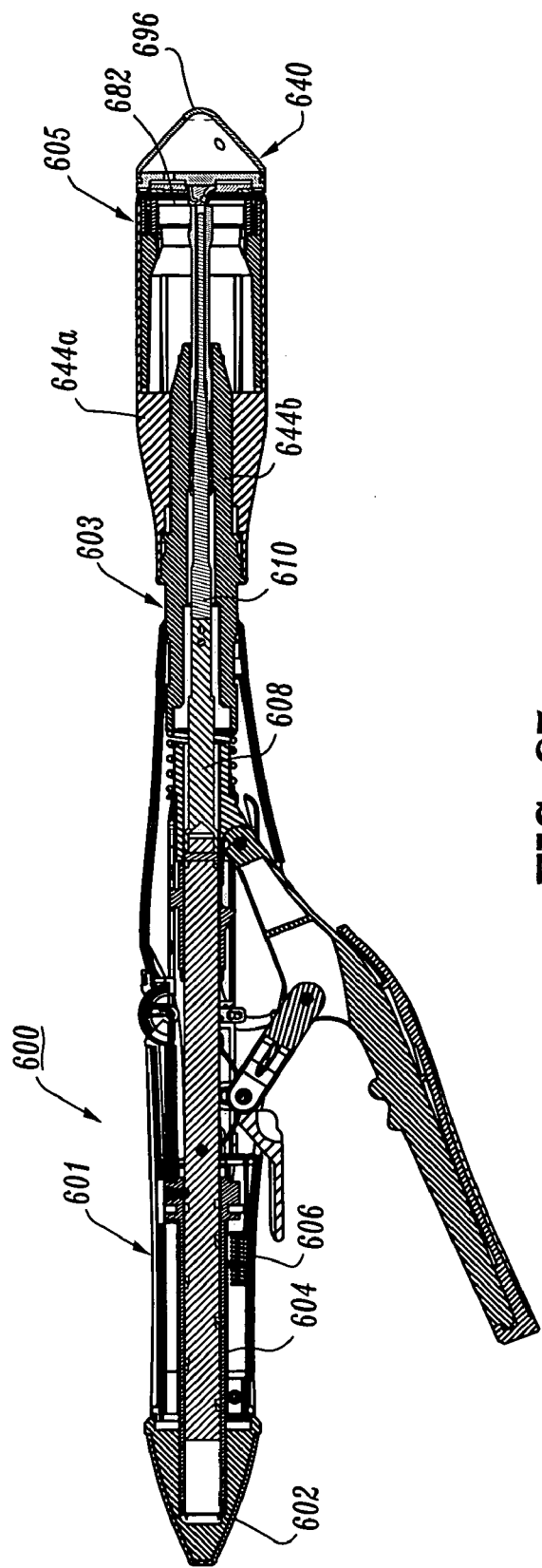
FIG. 65 is a side cross-sectional view of the surgical stapling device shown in FIG. 63 with the anvil assembly in the approximated position.
Figure 67:
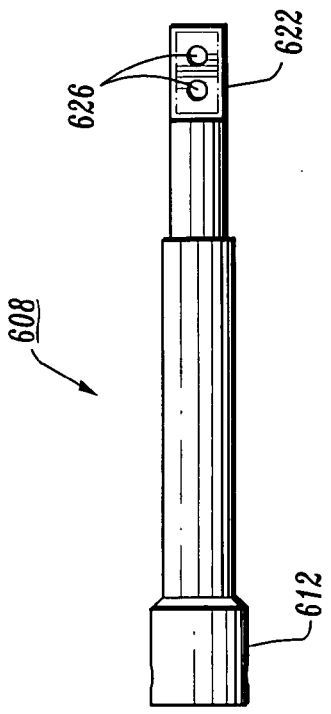
FIG. 67 is a side view of the retainer extension shown in FIG. 66.
Figure 66:
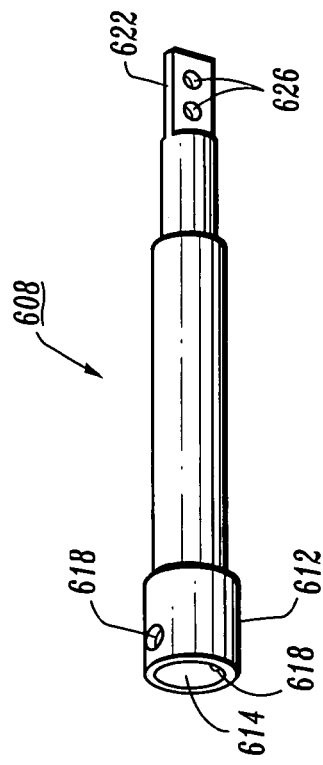
FIG. 66 is a side perspective view from the proximal end of the retainer extension of the surgical stapling device shown in FIG. 65.
Figure 68:
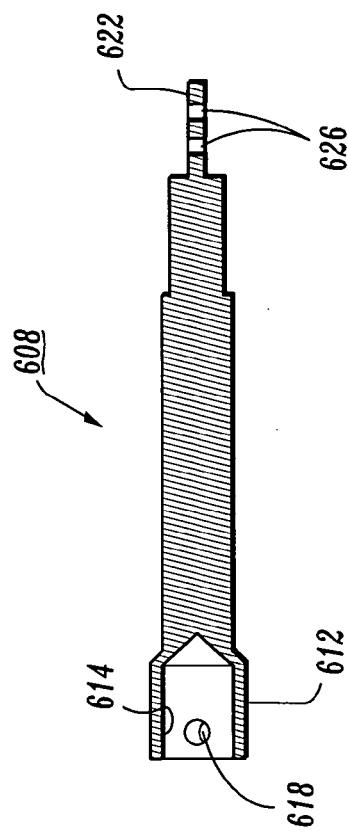
FIG. 68 is a top cross-sectional view of the retainer extension shown in FIG. 67.

Referring to FIGS. 62–71, the approximation mechanism of surgical stapling device 600 includes an approximation knob 602, a rotatable sleeve 604, a drive screw 606, a retainer extension 608, and an anvil retainer 610. Approximation knob 602, rotatable sleeve 604 and drive screw 606 are substantially identical to the like named components described above with respect to surgical stapling device 10 and will not be described in further detail herein. Referring to FIGS. 66–68, retainer extension 608 includes a proximal end 612 defining a bore 614 dimensioned to receive the distal end of drive screw 606. A pair of transverse openings 618 extend through sidewalls of the proximal end of retainer extension 608 to facilitate attachment of retainer extension 608 to the distal end of drive screw 606 with a pin or screw 620 (FIG. 62). Alternately, other known attachment devices may be used, e.g., welding, brazing, screw threads, etc. The distal end of retainer extension 608 includes a flat finger 622 configured to be received within a slot 624 (FIG. 69) formed in the proximal end of anvil retainer 610. Openings 626 and 626a in retainer extension 608 and anvil retainer 610 (FIG. 70), respectively, are dimensioned to receive pins or screws 628 (FIG. 62) to secure anvil retainer 610 to the distal end of retainer extension 608. Alternately, other attachment configurations and techniques are contemplated.

Figure 69:
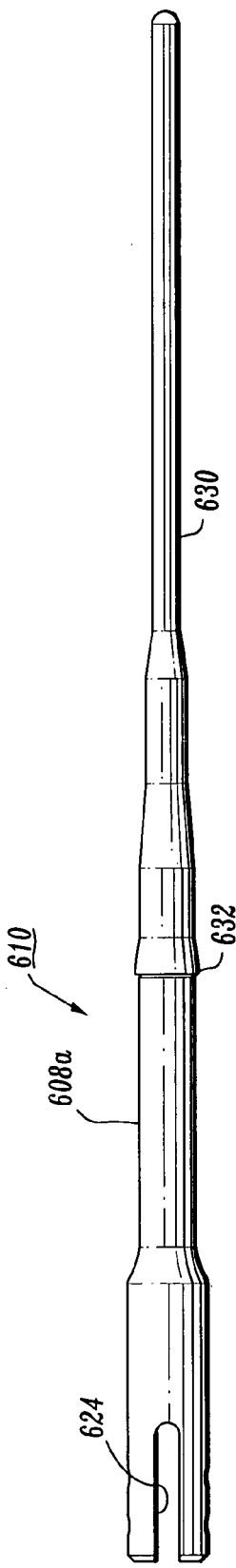
FIG. 69 is a top view of the anvil retainer of the surgical stapling device shown in FIG. 65.
Figure 70:
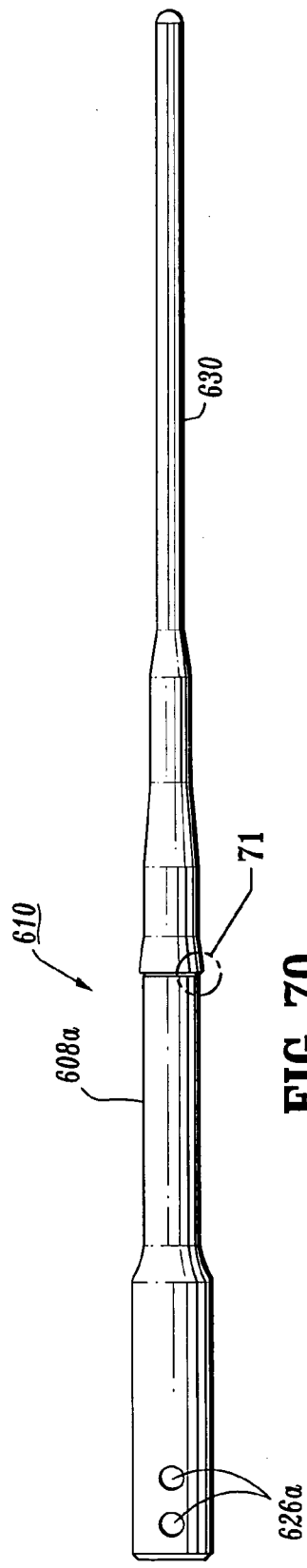
FIG. 70 is a side view of the anvil retainer shown in FIG. 69.
Figure 71:
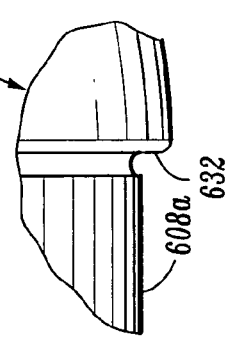
FIG. 71 is an enlarged view of the indicated area of detail shown in FIG. 70.
Figure 72:
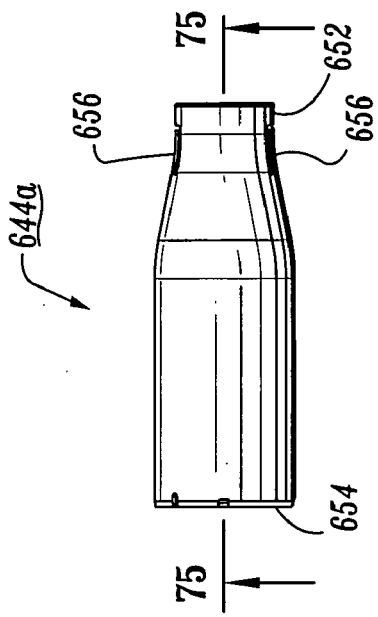
FIG. 72 is a side view of the outer housing portion of the shell assembly of the surgical stapling device shown in FIG. 65.
Figure 74:
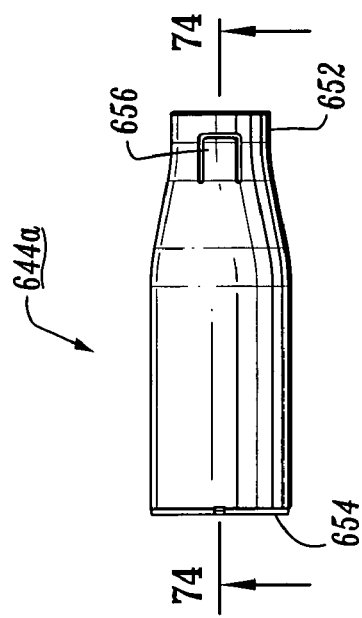
FIG. 74 is a cross-sectional view taken along section lines 74—74 of FIG. 72.
Figure 73:
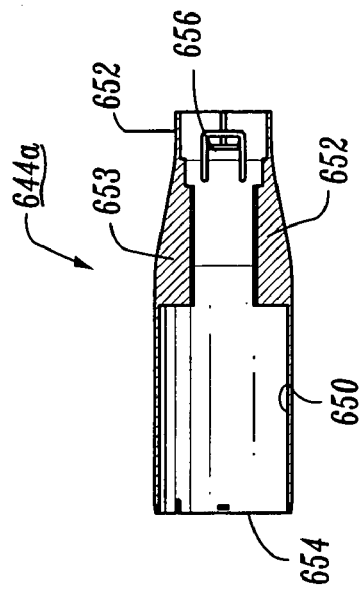
FIG. 73 is a top view of the outer housing portion of the shell assembly shown in FIG. 72.
Figure 75:
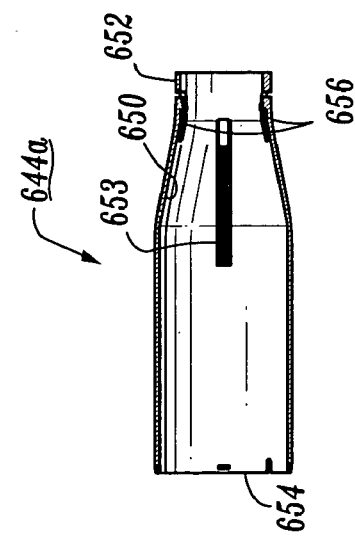
FIG. 75 is a cross-sectional view taken along section lines 75—75 of FIG. 73.
Figure 81:
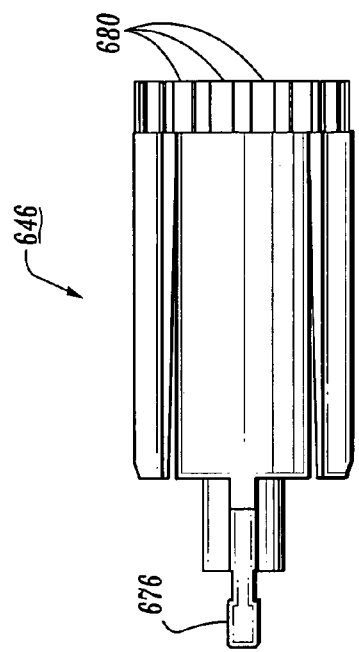
FIG. 81 is a top view of the pusher shown in FIG. 80.
Figure 80:
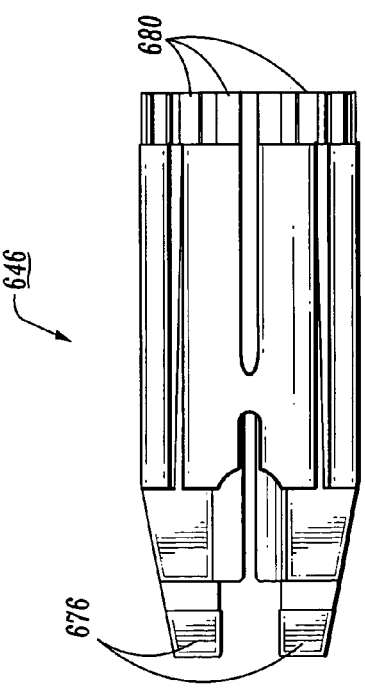
FIG. 80 is a side view of the pusher of the surgical stapling device shown in FIG. 65.
Figure 83:
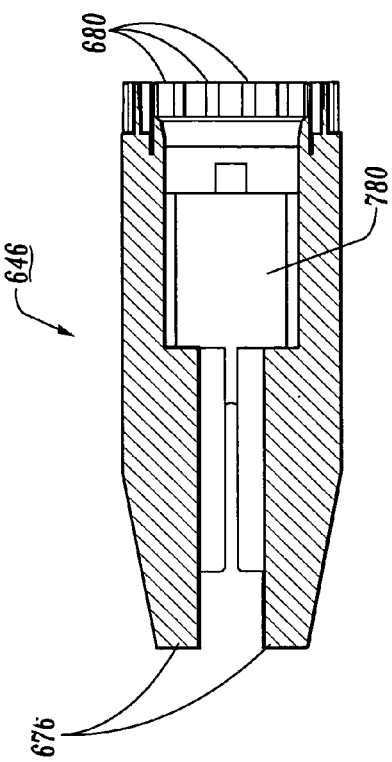
FIG. 83 is a top cross-sectional view of the pusher shown in FIG. 82.
Figure 82:
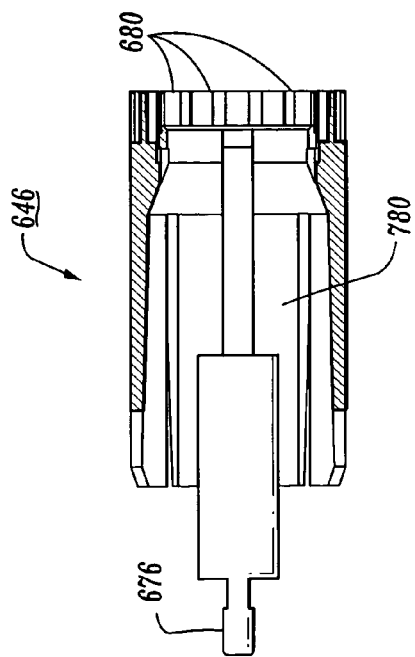
FIG. 82 is a side cross-sectional view of the pusher shown in FIG. 81.
Figure 88:
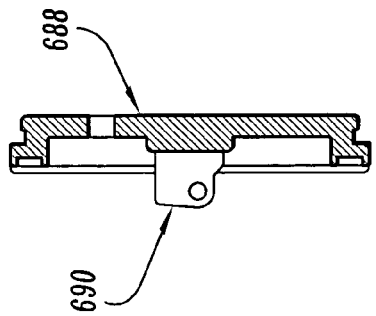
FIG. 88 is a side cross-sectional view of the anvil head of the anvil assembly shown in FIG. 85.
Figure 89:
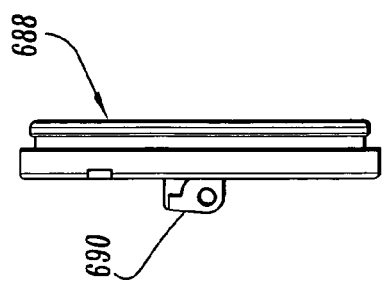
FIG. 89 is a side view of the anvil head shown in FIG. 88.
Figure 84:
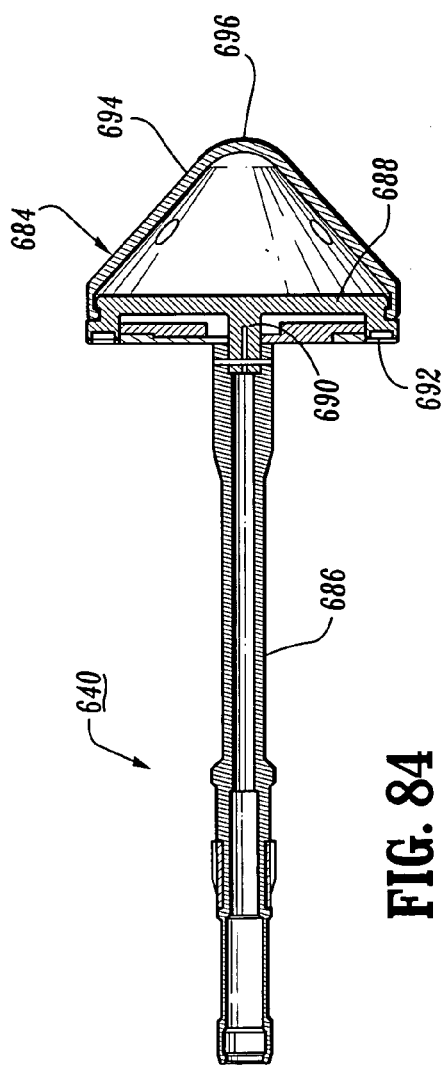
FIG. 84 is a side cross-sectional view of the anvil assembly of the surgical stapling device shown in FIG. 65.
Figure 85:
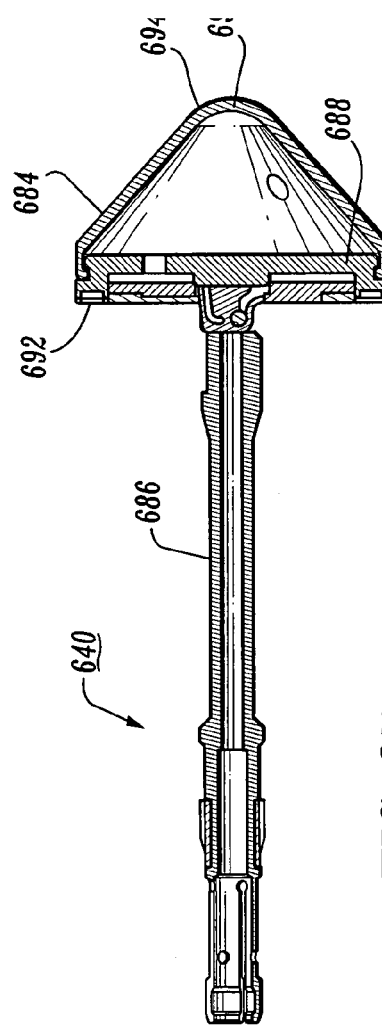
FIG. 85 is a top cross-sectional view of the anvil assembly of the surgical stapling device shown in FIG. 84.

Referring also to FIGS. 69–71, anvil retainer 610 includes an elongated reduced diameter distal extension 630 and a central annular shoulder 632. In one embodiment, annular shoulder 632 defines an angle of about ninety-degrees with respect to the outer axial surface 610a of anvil retainer 610 (FIG. 71). As will be discussed in further detail below, the sharp angle of shoulder 632 securely fastens an anvil assembly onto anvil retainer 610. As discussed above with respect to stapling device 10, when approximation knob 602 (FIG. 62) is manually rotated, rotatable sleeve 604 is rotated about the proximal end of screw 606 to advance or retract screw 606 within handle assembly 601. Since the proximal end 612 of retainer extension 608 is fastened to the distal end of screw 606 and the proximal end of anvil retainer 610 is fastened to the distal end of retainer extension 608, retainer extension 608 and anvil retainer 610 will move axially within central body portion 603 when drive screw 606 moves axially within handle assembly 601. As will be discussed in further detail below, an anvil assembly 640 (FIG. 64) is secured to anvil retainer 610. Accordingly, when approximation knob 602 is manually rotated, anvil assembly 640 will move axially with anvil retainer 610 in relation to a shell assembly 642 between spaced and approximated positions.

As illustrated in FIGS. 62–64, distal head portion 605 (FIG. 63) includes anvil assembly 640 and shell assembly 642. Shell assembly 642 includes a housing 644, a pusher 646, a cylindrical knife 645 and a staple guide 648. Referring also to FIGS. 72–79, housing 644 includes an outer housing portion 644a and an inner guide portion 644b. Outer housing portion 644a (FIGS. 72–75) defines an outwardly diverging throughbore 650 and includes a small diameter proximal end 652 and a large diameter distal end 654. Distal end 652 includes a pair of diametrically opposed spring tabs 656 for releasably engaging inner guide portion 644b in a manner to be discussed below. Throughbore 650 is dimensioned to slidably receive pusher 646 (FIG. 62). Because of the configuration of throughbore 650 and pusher 646, pusher 646 is slidable in throughbore 650 only in a distal direction. A pair of stabilizing ribs 653 (FIG. 75) extend inwardly from an inner wall defining throughbore 650. Stabilizing ribs 653 engage ribs 654 (FIG. 76) formed on sidewalls of inner guide portion 644b to secure inner guide portion 644b within outer housing portion 644a.

Inner guide portion 644b (FIGS. 76–79) includes a cylindrical proximal end 658, a cylindrical central portion 660 and an inner distal portion 662. Proximal end 658 includes a pair of openings 664 for engaging spring tabs (not shown) formed on handle assembly 612 for securing shell assembly 642 onto handle assembly 612. Ribs 654 are formed on inner distal portion 662 of inner guide portion 644b. A pair of annular ribs 666 are formed in spaced relation on central portion 660. Spring tabs 656 of outer housing portion 644a (FIGS. 72–75) are positioned to snap fit into the space between ribs 666 to secure inner guide portion 644b to outer housing portion 644a. Inner distal portion 662 defines a cylindrical bore 668 for slidably receiving retainer extension 608 and anvil retainer 610 (FIG. 62). Cylindrical bore 668 includes an annular array of ribs and grooves 676 for accurately circumferentially and axially aligning anvil assembly 640 and shell assembly 642 during approximation thereof. The proximal end of distal portion 662 extends proximally within central portion 660 to define therewith a pair of channels 670 (FIG. 78). A proximal portion of channels 670 is dimensioned to slidably receive drive arms of a pusher link (not shown). The pusher link employed in this embodiment is similar to pusher link 74 discussed above with respect to stapling device 10 and will not be discussed in further detail herein.

Referring to FIGS. 62 and 80–83, pusher 646 is slidably positioned within shell assembly housing 644. Pusher 646 includes a pair of proximal extensions 676 which extends through the distal end of channels 670 (FIG. 78) formed in inner guide portion 644b. The distal end of pusher 646 includes a multiplicity of distally extending fingers 680 which are slidably received within slots formed in staple guide 648 (FIG. 62). Staple guide 648 is fixedly retained in the distal end of outer housing portion 644a. Staples (not shown) are housed within the staple guide slots (not shown). Movement of pusher 646 distally within outer housing portion 644a ejects staples from the slots of staple guide 648. A cylindrical knife 645 (FIGS. 62 and 63) is secured or frictionally retained within a central throughbore of pusher 646. The distal end of knife 645 includes an annular cutting edge 682. The distal portion of pusher 646 defines an internal chamber 780 for receiving excised tissue.

Figure 92:
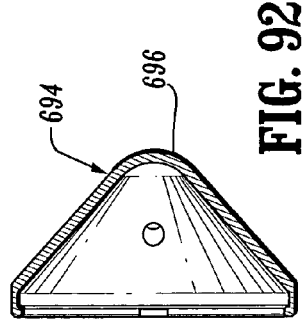
FIG. 92 is a side cross-sectional view of the anvil cover shown in FIG. 91.
Figure 91:
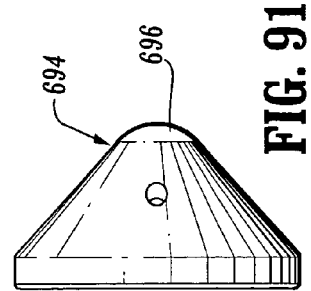
FIG. 91 is a side view of the anvil cover of the anvil assembly shown in FIG. 84.

Referring to FIGS. 84–89, anvil assembly 640 includes an anvil head assembly 684 and an anvil center rod 686. Anvil head assembly 684 includes an anvil head 688, an anvil post 690, an anvil 692 and an anvil cover 694. Anvil cover 694 (FIGS. 91 and 92) is substantially conical and includes a rounded distal portion 696 to facilitate smooth entry of anvil assembly 640 into a body lumen or orifice, e.g., anus. Anvil 692 is secured to anvil head 688 and includes a plurality of staple deforming pockets (not shown), as discussed above, for receiving and deforming staples. Anvil head assembly 684 is secured to the distal end of anvil center rod 686. Although anvil head assembly 684 may be pivotally secured to anvil center rod 686, as discussed above, in one embodiment, anvil head assembly 684 is fixedly secured to anvil center rod 686.

Figure 86:
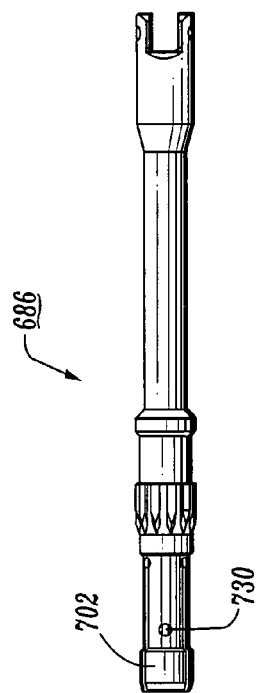
FIG. 86 is a top view of the anvil center rod of the anvil assembly shown in FIG. 85.
Figure 87:
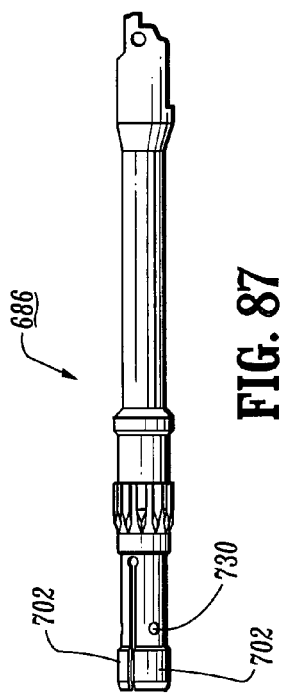
FIG. 87 is a side view of the anvil center rod of the anvil assembly shown in FIG. 85.
Figure 90:
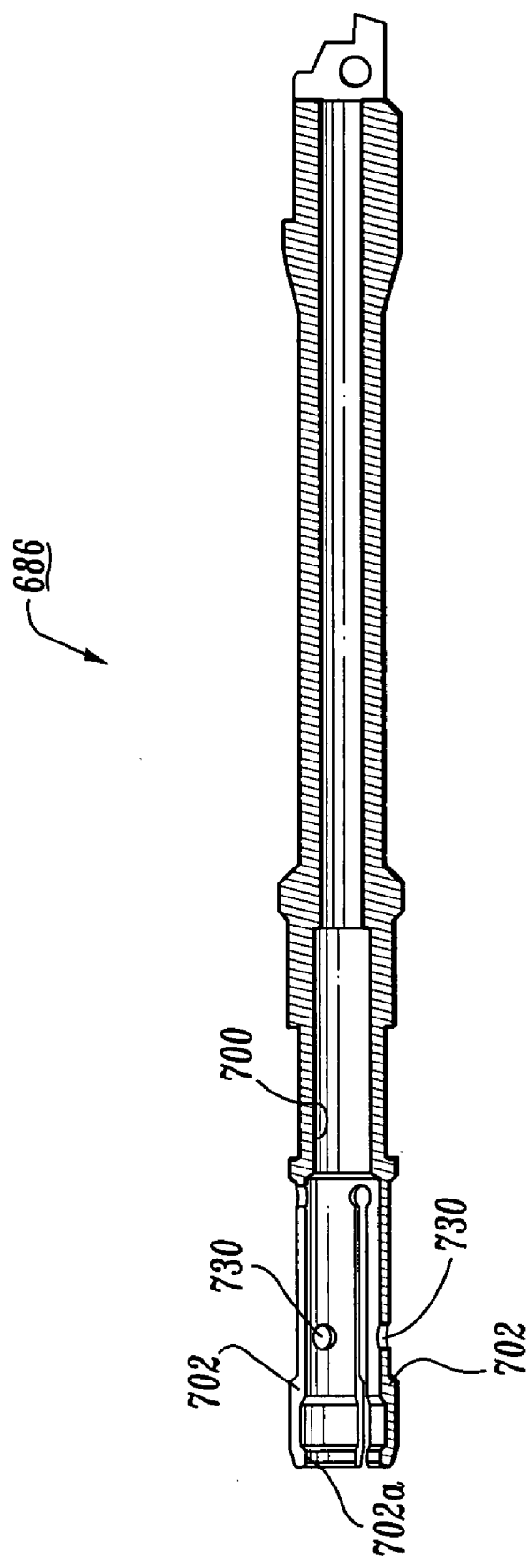
FIG. 90 is a side cross-sectional view of the anvil center rod shown in FIG. 87.
Figure 97:
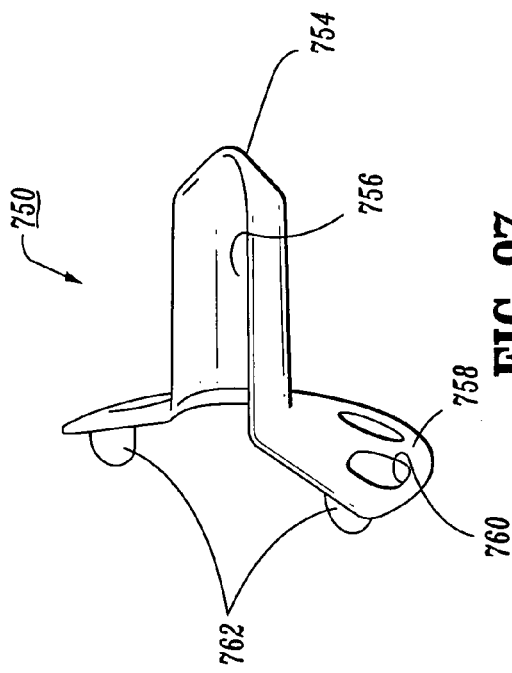
FIG. 97 is a side perspective view from above of the speculum shown in FIG. 96.
Figure 99:
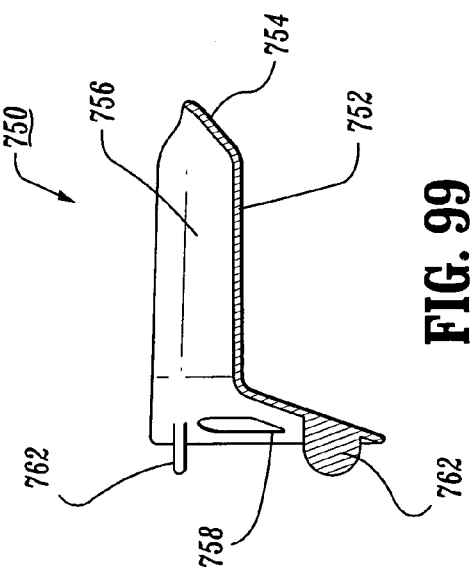
FIG. 99 is a side cross-sectional view of the speculum shown in FIG. 97.
Figure 96:
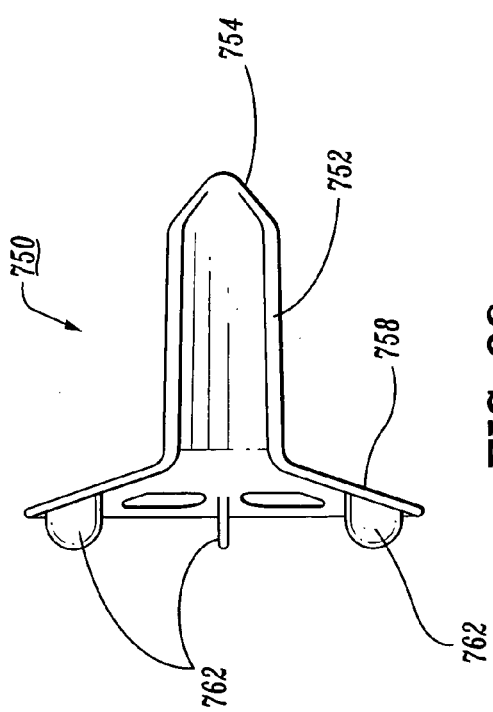
FIG. 96 is a top view of a speculum suitable for use with the presently disclosed surgical stapling device.
Figure 98:
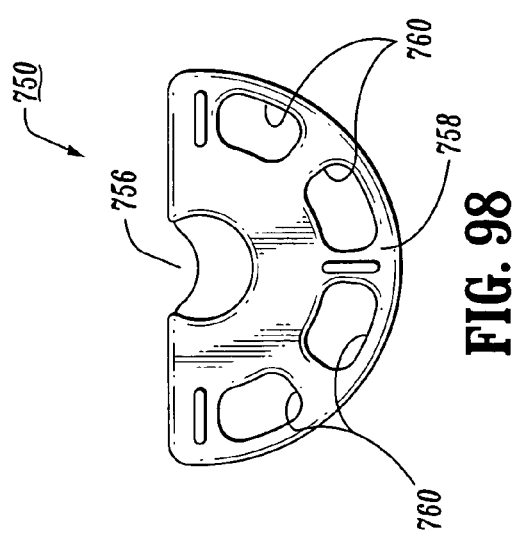
FIG. 98 is a rear view of the speculum shown in FIG. 96.

As illustrated in FIGS. 86 and 87 and 90, anvil center rod 686 defines a central bore 700 which is partially defined by a plurality of flexile arms 702. Central bore 700 extends substantially along the longitudinal length of center rod 686. The distal end of each flexible arm 702 includes a radial projection 702a. Central bore 700 is dimensioned to slidably receive anvil retainer 610 (FIG. 62) including distal extension 630 such that radial projections 702a snap over and engage annular shoulder 632 (FIGS. 70 and 71) of anvil retainer 610 to secure anvil assembly 640 to anvil retainer 610. Radial projection 702a (FIG. 90) defines a perpendicular surface which abuts shoulder 632 to securely fasten anvil assembly 640 to anvil retainer 610 and substantially prevent inadvertent disengagement of anvil assembly 640 from anvil retainer 610. When anvil assembly 640 is secured to anvil retainer 610, distal extension 630 of anvil retainer 610 extends through central bore 700 along a substantial portion of the length of anvil center rod 686. In one embodiment, distal extension 630 extends through central bore 700 substantially the entire length of anvil center rod 686.

In use, when approximation knob 602 (FIG. 63) is manually rotated to move screw 606 proximally, anvil retainer 610 and anvil assembly 640 are withdrawn into shell assembly 642 to move anvil head assembly 684 into approximation with shell assembly 642 (FIG. 65). When flexible arms 702 are drawn into cylindrical bore 668 of inner guide portion 644b, arms 702 are prevented from flexing outwardly to lock anvil assembly 640 to anvil retainer 610.

As discussed above, stapling device 600 is particularly suitable for use in surgical procedures for removing internal hemorrhoids from a patient. During such a procedure, anvil assembly 640 (FIG. 64) is inserted into the anus and rectum of the patient independently of stapling device 600. Referring to FIGS. 93–95, an insertion handle 720 may be used to facilitate insertion of anvil assembly 640 into the anus and rectum. In one embodiment, handle 720 includes a gripping knob 722, a rigid shaft 725 extending distally from knob 722 and an attachment portion 724. Attachment portion 724 includes a detent 726 and a protrusion 728. Attachment portion 725 of shaft 724 is dimensioned to be slidably received within anvil center rod central bore 700. Detent 726 is positioned to be received within one of a plurality of suture holes 730 (FIG. 87) formed in the distal end of anvil center rod 686 to releaseably lock handle 720 to anvil center rod 686. Protrusion 728 is positioned to be slidably received between and engaged by flexible arms 702 to properly align handle 720 with anvil center rod 686. A stop member 728a may also be provided on the attachment portion to limit the insertion depth of shaft 724 into central bore 700. To remove handle 720 from anvil center rod 686, a force sufficient to flex flexible arms 702 outwardly must be applied to handle 720 to release detent 726 from suture hole 730. In one embodiment, after anvil assembly 640 has been properly positioned in the anus and rectum, a purse string suture is placed into each of the internal hemorrhoids. Thereafter, the purse string is cinched about the anvil center rod 686 to draw the internal hemorrhoids inwardly about the anvil center rod 686.

Referring to FIGS. 96–99, in an alternate embodiment, the purse string suture may be placed into the internal hemorrhoids prior to insertion of the anvil assembly into the anus and rectum. Using either embodiment, an anoscope or speculum 750, may be provided to place the purse string into the internal hemorrhoids. Speculum 750 may include a semi-cylindrical body 752 having a tapered or blunt tip 754. Body 752 defines a channel or recess 756. The proximal end of body 752 has a semi-annular flange 758 including a plurality of openings 760 and a pair of protruding finger tabs 762. Fingers tabs 762 and openings 760 allow for easier gripping and manipulation of the speculum during use. It is also envisioned that speculum 750 may be formed from a clear plastic material to enhance visualization. Further, the speculum 750 may include gradation markings (not shown) along the surface of the speculum 750 to assist the surgeon with knowledge of depth of placement of the hemorrhoids.

In use, blunt tip 754 of speculum 750 is inserted into the anus to a position in which first internal hemorrhoids hang into channel 756. A purse string suture is placed into a first portion of internal hemorrhoids. Speculum 750 is then rotated using finger tabs 762 and openings 760 until a second portion of internal hemorrhoids hang into channel 756. A purse string suture is placed into the second internal hemorrhoids. This process is repeated until a purse string suture has been placed into each of the internal hemorrhoids about the annulus of the anus.

When a purse string suture has been placed into each of the internal hemorrhoids, speculum 750 is removed from the anus and the anvil assembly 640 is inserted into the anus and rectum. Thereafter, the purse string sutures are cinched to draw the internal hemorrhoids in about the anvil center rod 686. Attachment structure such as openings, grooves, hooks, ridges or ribs, may be provided on anvil center rod 686 to secure the purse string suture and, thus, the internal hemorrhoids to the anvil center rod 686. It is also envisioned that the attachment structure may be in the form of an axially adjustable member, e.g., slidable hook, which may be adjusted to change the position of the purse string suture on anvil center rod 686 and within shell assembly 642. Likewise, gradations can be placed on the center rod 686 to indicate depth of insertion of the center rod 686 or length of the suture or of sutured hemorrhoids.

After the internal hemorrhoids have been cinched about anvil center rod 686, center rod 686 is attached to anvil retainer 610 in the manner discussed above. Distal extension 630 and anvil center rod 686 should be of a length to allow telescoping of extension 630 within anvil center rod 686 before visibility of the surgical site is obstructed by shell assembly 642 of device 600. In one embodiment, the combined length of anvil center rod 686 and retainer extension 630 is at least 4.5 inches (114.3) or of a length to achieve the above objective. By providing an extension on anvil retainer 610 and/or providing an elongated anvil center rod 686, visibility at the surgical site is greatly improved. Improved visibility not only simplifies attachment of anvil assembly 640 to anvil center rod 686 but improves visibility during approximation of anvil to ensure that the hemorrhoidal tissue is properly positioned about the anvil shaft.

After the anvil assembly has been attached to the anvil center rod 686, knob 602 can be manually rotated to approximate the anvil and shell assemblies and draw the internal hemorrhoids into an inner chamber 780 (FIG. 62)

defined within pusher 646 and within annular knife 682 of shell assembly 642. Firing trigger 790 (FIG. 62) can now be actuated in the manner discussed above with respect to stapling device 10 to staple, sever and allow removal of the internal hemorrhoids. Thereafter, stapling device 600 is removed from the anus with the excised internal hemorrhoids contained within inner chamber 780 of shell assembly 642.

It is envisioned that instrument accessories may be used to assist in performing particular steps of the above described procedures. For example, an anal dialator may be inserted into the anus prior to performing the above-described method steps to provide easier access to the surgical site. An obturator may be used to assist in placement of the dialator. Also, an expandable introducer may be provided to reduce the trauma that results from insertion of the stapling device into the anus. Further, any combination of the components discussed above including the stapling device, anvil assembly, insertion handle, speculum anal dialator, and/or an obturator may be included in a kit to perform a hemorrhoidal treatment procedure.

It is noted that by providing a surgical stapler having a removable anvil assembly, visibility at the surgical site is greatly improved. This is especially important during placement of the purse string suture and cinching of the purse string suture about the anvil center rod.

It will be understood that various modifications may be made to the embodiments disclosed herein. Therefore, the above description should not be construed as limiting, but merely as exemplifications of disclosed embodiments. Those skilled in the art will envision other modifications within the scope and spirit of the claims appended hereto.

What is claimed is:

1. A surgical stapling device comprising:
   a handle assembly;
   a body portion extending distally from the handle assembly;
   a head portion including an anvil assembly and a shell assembly, the anvil assembly including an anvil head and an anvil center rod having a proximal end and a distal end and defining a longitudinal bore, the anvil head being supported on the distal end of the anvil center rod, the shell assembly supporting a plurality of staples, the anvil assembly being movable in relation to the shell assembly between spaced and approximated positions; and
   an approximation mechanism including an anvil retainer for supporting the anvil assembly, the anvil retainer including an annular shoulder configured to engage the anvil center rod to fasten the anvil center rod to the anvil retainer, the anvil retainer further including an elongated distal extension positioned distally of the annular shoulder and dimensioned to be telescopingly received in the longitudinal bore of the anvil center rod, wherein the distal extension has a distal end positioned substantially adjacent the distal end of the anvil center rod when the anvil center rod is engaged to the anvil retainer.

2. A surgical stapling device according to claim 1, wherein the longitudinal bore extends along substantially the entire length of the anvil center rod, the elongated distal extension of the anvil retainer extending substantially the length of the longitudinal bore.

3. A surgical stapling device according to claim 1, wherein the anvil assembly is removably secured to the anvil retainer.

4. A surgical stapling device according to claim 3, wherein the anvil center rod includes a plurality of flexible arms which partially define the longitudinal bore, at least one of the flexible arms including a radial projection, the radial projection of the at least one flexible arm being engageable with the anvil retainer annular shoulder to releasably secure the anvil assembly to the anvil retainer.

5. A surgical stapling device according to claim 1, wherein the elongated distal extension of the anvil retainer has a smaller diameter than the proximal portion of the anvil retainer.

6. A surgical stapling device according the claim 1, wherein the approximation mechanism includes a rotatable approximation knob supported on the handle assembly, a screw operably associated with the approximation knob, and a retainer extension member secured to the screw, the anvil retainer being secured to the distal end of the retainer extension member.

7. A surgical stapling device according to claim 1, wherein the elongated distal extension is of a length to allow telescoping of the elongated distal extension with the anvil center rod without obstructing visibility of a surgical site.

* * * * *